(12) United States Patent
Sasaki

(10) Patent No.: US 8,512,531 B2
(45) Date of Patent: Aug. 20, 2013

(54) GAS CONCENTRATION DETECTION APPARATUS

(75) Inventor: Takanori Sasaki, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 252 days.

(21) Appl. No.: 12/744,543

(22) PCT Filed: Feb. 10, 2009

(86) PCT No.: PCT/JP2009/052593
§ 371 (c)(1),
(2), (4) Date: May 25, 2010

(87) PCT Pub. No.: WO2009/102072
PCT Pub. Date: Aug. 20, 2009

(65) Prior Publication Data
US 2011/0016949 A1    Jan. 27, 2011

(30) Foreign Application Priority Data

Feb. 14, 2008 (JP) ................. 2008-033351
Mar. 21, 2008 (JP) ................. 2008-074458

(51) Int. Cl.
*G01N 27/419* (2006.01)
(52) U.S. Cl.
USPC .......................... 204/401; 73/23.31
(58) Field of Classification Search
USPC ............. 204/401; 73/23.31, 23.32, 114.72, 73/114.73
See application file for complete search history.

(56) References Cited

U.S. PATENT DOCUMENTS

| | | | |
|---|---|---|---|
| 2004/0238378 A1 | 12/2004 | Kumazawa et al. | |
| 2007/0119709 A1 | 5/2007 | Oya et al. | |

FOREIGN PATENT DOCUMENTS

| | | |
|---|---|---|
| DE | 100 49 685 A1 | 4/2002 |
| DE | 103 00 939 A1 | 7/2004 |
| EP | 1 480 039 A1 | 11/2004 |
| JP | A-11-237363 | 8/1999 |
| JP | A-2002-116180 | 4/2002 |
| JP | A-2003-050227 | 2/2003 |
| JP | A-2003-166967 | 6/2003 |
| JP | A-2003-270194 | 9/2003 |
| JP | A-2004-177179 | 6/2004 |
| WO | WO 2008/004917 A1 | 1/2008 |

OTHER PUBLICATIONS

International Search Report issued on May 18, 2009 in International Application No. PCT/JP2009/052593.
Written Opinion of the International Searching Authority issued on May 18, 2009 in International Application No. PCT/JP2009/052593.

*Primary Examiner* — Lisa Caputo
*Assistant Examiner* — Punam Roy
(74) *Attorney, Agent, or Firm* — Oliff & Berridge, PLC

(57) ABSTRACT

The present invention relates to a gas concentration detection apparatus for detecting the concentration of a specific gas component in an exhaust gas emitted from an engine, and forms a deterioration judgment about the gas concentration detection apparatus accurately and immediately. After excess oxygen is discharged by an oxygen pump cell 2, a NOx concentration detection apparatus, judges whether a NOx sensor 1 is activated. If the NOx sensor 1 is not activated yet, an output increase rate Vu(t) of the NOx sensor cell output N during an increase process of the NOx sensor cell output N is acquired. The present invention judges whether the output increase rate Vu(t) is lower than a predetermined reference value Vth1. If the obtained judgment result indicates that Vu(t)<Vth1, the NOx sensor cell 4 is deteriorated.

19 Claims, 27 Drawing Sheets

GAS CONCENTRATION DETECTION APPARATUS

TECHNICAL FIELD

The present invention relates to a gas concentration detection apparatus, and more particularly to deterioration judgment about a gas concentration detection apparatus that detects the concentration of a specific gas component in an exhaust gas emitted from an engine.

BACKGROUND ART

A conventionally proposed apparatus disclosed, for instance, in JP-A-2003-166967 exercises heater energization control so that the element resistance of a pump cell agrees with a target element resistance. When the element resistance of a sensor cell is outside a predefined range during heater energization control, this apparatus concludes that a sensor is deteriorated.
Patent Document 1:
  JP-A-2003-166967
Patent Document 2:
  JP-A-11-237363
Patent Document 3:
  JP-A-2003-270194
Patent Document 4:
  JP-A-2002-116180
Patent Document 5:
  JP-A-2003-50227
Patent Document 6:
  JP-A-2004-177179

DISCLOSURE OF INVENTION

Problem to be Solved by the Invention

However, the element resistance (impedance), the power supplied to a heater, and the heater resistance, for example, vary from one sensor unit to another due to individual sensor differences. Therefore, if these values are used to form a deterioration judgment about the sensor, the accuracy of deterioration judgment may decrease due to individual sensor differences.

Further, when heater energization control is exercised to activate the sensor, it is necessary to raise the element temperature excessively and maintain it in consideration of individual sensor differences. Therefore, a deterioration judgment about the sensor may not be formed early. In addition, when an attempt is made to raise the element temperature excessively, the impedance varies. Consequently, the accuracy of deterioration judgment may decrease.

The present invention has been made to solve the above problem. An object of the present invention is to provide a gas concentration detection apparatus that is capable of forming a deterioration judgment about the gas concentration detection apparatus accurately and immediately.

Means for Solving the Problem

First aspect of the present invention is a gas concentration detection apparatus comprising:
a gas sensor which includes oxygen concentration control means for changing the concentration of oxygen in a measurement target gas and a gas concentration detection cell for detecting the concentration of a specific gas component in the gas whose oxygen concentration is changed by the oxygen concentration control means; and
deterioration judgment means which forms a deterioration judgment about the gas sensor in accordance with a cell output from the gas concentration detection cell.

Second aspect of the present invention is the gas concentration detection apparatus according to the first aspect, wherein the oxygen concentration control means includes excess oxygen removal means for removing excess oxygen from the measurement target gas; and wherein the deterioration judgment means forms a deterioration judgment about the gas sensor during the warm-up of the gas sensor and the execution of the excess oxygen removal means in accordance with the cell output obtained before an inflection point appears in the cell output of the gas concentration detection cell.

Third aspect of the present invention is the gas concentration detection apparatus according to the second aspect, wherein the deterioration judgment means includes increase rate correlation value acquisition means for acquiring a correlation value of the rate at which the cell output increases during a cell output increase process (hereinafter referred to as the increase rate correlation value), and forms a deterioration judgment about the gas concentration detection cell in accordance with a comparison between the increase rate correlation value and a predetermined reference value.

Fourth aspect of the present invention is the gas concentration detection apparatus according to the third aspect, wherein the increase rate correlation value acquisition means includes increase rate acquisition means for acquiring an increase rate of the cell output; and wherein the deterioration judgment means forms a deterioration judgment about the gas concentration detection cell when the increase rate is lower than a predetermined reference value.

Fifth aspect of the present invention is the gas concentration detection apparatus according to any one of the second to the fourth aspects, wherein the excess oxygen removal means includes an oxygen pump cell and discharges excess oxygen in the measurement target gas upon voltage application to the oxygen pump cell; and wherein the deterioration judgment means includes decrease rate correlation value acquisition means for acquiring a correlation value of the rate at which the cell output decreases during a cell output decrease process (hereinafter referred to as the decrease rate correlation value), and forms a deterioration judgment about the oxygen pump cell in accordance with a comparison between the decrease rate correlation value and a predetermined reference value.

Sixth aspect of the present invention is the gas concentration detection apparatus according to the fifth aspect, wherein the decrease rate correlation value acquisition means includes decrease rate acquisition means for acquiring a decrease rate of the cell output; and wherein the deterioration judgment means forms a deterioration judgment about the oxygen pump cell when the decrease rate is lower than a predetermined reference value.

Seventh aspect of the present invention is the gas concentration detection apparatus according to the fifth aspect, wherein the decrease rate correlation value acquisition means includes integrated value acquisition means for acquiring an integrated value of the cell output that is reached during the interval between the instant at which the gas sensor begins to warm up and the instant at which an inflection point appears; and wherein the deterioration judgment means forms a deterioration judgment about the oxygen pump cell when the integrated value is greater than a predetermined reference value.

Eighth aspect of the present invention is the gas concentration detection apparatus according to any one of the second to the seventh aspects, further comprising:

inflection point cell output acquisition means for acquiring a cell output at the inflection point (hereinafter referred to as the inflection point cell output); and storage means for storing a learned value concerning the inflection point cell output;

wherein the deterioration judgment means forms a deterioration judgment about the gas sensor in accordance with a comparison between the inflection point cell output and the learned value.

Ninth aspect of the present invention is the gas concentration detection apparatus according to the eighth aspect, wherein, when the cell output is smaller than the learned value and the deviation between the learned value and the cell output is greater than a predetermined reference value, the deterioration judgment means concludes that the gas sensor is deteriorated.

Tenth aspect of the present invention is the gas concentration detection apparatus according to the eighth aspect, wherein, when the cell output is greater than the learned value and the absolute value of the deviation between the learned value and the cell output is greater than a predetermined reference value, the deterioration judgment means concludes that the gas sensor is deteriorated.

Eleventh aspect of the present invention is the gas concentration detection apparatus according to the eighth aspect, wherein the deterioration judgment means includes temporary deterioration judgment means, which forms a recoverable temporary deterioration judgment about the gas sensor in accordance with a comparison between the cell output and the learned value.

Twelfth aspect of the present invention is the gas concentration detection apparatus according to the eleventh aspect, wherein, when the absolute value of the deviation between the learned value and the cell output is smaller than a predetermined reference value, the temporary deterioration judgment means concludes that the gas sensor is temporarily deteriorated.

Thirteenth aspect of the present invention is the gas concentration detection apparatus according to the eleventh or the twelfth aspect, further comprising:

deterioration recovery process execution means, which performs a deterioration recovery process on the gas sensor when the gas sensor is judged to be temporarily deteriorated.

Fourteenth aspect of the present invention is the gas concentration detection apparatus according to any one of the eighth to the thirteenth aspects, wherein the storage means stores the cell output as an updated learned value when the cell output is smaller than the learned value and the deviation between the learned value and the cell output is smaller than a predetermined reference value.

Fifteenth aspect of the present invention is the gas concentration detection apparatus according to the first aspect, wherein the oxygen concentration control means includes oxygen concentration increase means for increasing the concentration of oxygen in the measurement target gas; inflection point location means which, while the oxygen concentration is decreased after being increased from a predetermined value by the oxygen concentration increase means, locates an inflection point appearing in the cell output as an active site of the gas sensor; and inflection point learned value storage means for storing an inflection point learned value that is the information about the inflection point located by the inflection point location means; and wherein the deterioration judgment means forms a deterioration judgment about the gas sensor in accordance with the inflection point learned value stored by the inflection point learned value storage means.

Sixteenth aspect of the present invention is the gas concentration detection apparatus according to the fifteenth aspect, further comprising:

NOx concentration estimation means for estimating a NOx concentration in the measurement target gas; and correction means for correcting the cell output by using the NOx concentration estimated by the NOx concentration estimation means;

wherein, while the oxygen concentration is decreased after being increased from a predetermined value by the oxygen concentration increase means, the inflection point location means identifies an inflection point in the cell output corrected by the correction means as an active site of the gas sensor.

Seventeenth aspect of the present invention is the gas concentration detection apparatus according to the fifteenth aspect, wherein the oxygen concentration increase means includes an oxygen pump cell for discharging excess oxygen in the measurement target gas and heater control means for controlling the power supply to a heater for warming up the oxygen pump cell, and supplies a smaller amount of power to the heater than normal during an internal combustion engine fuel cut.

Eighteenth aspect of the present invention is the gas concentration detection apparatus according to the fifteenth aspect, wherein the oxygen concentration increase means includes an oxygen pump cell for discharging excess oxygen in the measurement target gas upon voltage application and oxygen pump cell control means for controlling the power supply to the oxygen pump cell, and supplies a smaller amount of power to the oxygen pump cell than normal during an internal combustion engine fuel cut.

Nineteenth aspect of the present invention is the gas concentration detection apparatus according to the fifteenth aspect, further comprising:

NOx concentration control means for controlling the concentration of NOx in the measurement target gas;

wherein the inflection point location means locates the inflection point while the NOx concentration control means is executed.

Twentieth aspect of the present invention is the gas concentration detection apparatus according to any one of the fifteenth to the nineteenth aspects, wherein the inflection point learned value storage means stores, as a map, the cell output prevailing when the inflection point is located, a physical property value correlated to an element temperature, and the time required for locating the inflection point.

Advantages of the Invention

According to the first aspect of the present invention, a deterioration judgment about the gas sensor is formed in accordance with the cell output of the gas concentration detection cell. Therefore, the present invention makes it possible to form a deterioration judgment without being affected by individual gas sensor differences.

The time at which an inflection point appears in the cell output of the gas concentration detection cell is the time at which the excess oxygen remaining in the measurement target gas is removed by the excess oxygen removal means to the extent that the cell output of the gas concentration detection cell remains unaffected. In other words, an activity judgment about the gas sensor can be formed when the inflection point appears in the cell output. The second aspect of the present invention forms a deterioration judgment about the gas sensor in accordance with the cell output generated before the inflection point appears in the cell output. According to the present invention, therefore, a deterioration judgment can be formed before the gas sensor becomes active. This makes it possible to effectively avoid a situation where the sensor output of a deteriorated gas sensor is used for various control operations.

When the temperature of the gas concentration detection cell rises as the warm-up of the gas sensor progresses, a cell output is obtained because the oxygen remaining in the measurement target gas is decomposed by the gas concentration detection cell. The cell output increases with an increase in the activity of the gas concentration detection cell. When the gas concentration detection cell deteriorates in the resulting state, the oxygen decomposition capability of the gas concentration detection cell decreases. This lowers the increase rate of the cell output. According to the third aspect of the present invention, a deterioration judgment about the gas concentration detection cell is formed by comparing the correlation value of the output increase rate and the predetermined reference value during a cell output increase process. Consequently, the present invention makes it possible to form a deterioration judgment about the gas concentration detection cell with high accuracy before an inflection point appears in the cell output, that is, before the gas sensor becomes active.

According to the fourth aspect of the present invention, the cell output increase rate of the gas concentration detection cell is acquired during a cell output increase process. When the increase rate is lower than the predetermined reference value, it is judged that the gas concentration detection cell is deteriorated. When the cell output increase rate is low, it can be judged that the oxygen decomposition capability of the gas concentration detection cell is decreased. Therefore, the present invention makes it possible to form a deterioration judgment about the gas concentration detection cell early and accurately in accordance with the cell output increase rate.

When the activity of the oxygen pump cell increases as the warm-up of the gas sensor progresses, the oxygen pump cell discharges the excess oxygen more and more vigorously. Therefore, the cell output, which has once increased, decreases with a decrease in the amount of excess oxygen in the measurement target gas. The fifth aspect of the present invention forms a deterioration judgment about the oxygen pump cell in accordance with a comparison between the correlation value of the cell output decrease rate and the predetermined reference value. In other words, when the oxygen pump cell deteriorates, the oxygen decomposition capability, that is, the excess oxygen discharge capacity, decreases. Consequently, the gas concentration detection cell detects high-concentration oxygen at all times. This lowers the cell output decrease rate. Thus, the present invention makes it possible to form a deterioration judgment about the oxygen pump cell early and accurately before inflection point appearance in the cell output, that is, before gas sensor activation, in accordance with the comparison between the correlation value of the cell output decrease rate and the predetermined reference value.

When the oxygen pump cell deteriorates, the oxygen decomposition capability, that is, the excess oxygen discharge capacity, decreases. Thus, the gas concentration detection cell detects high-concentration oxygen at all times, thereby decreasing the cell output decrease rate. The sixth aspect of the present invention acquires the cell output decrease rate of the gas concentration detection cell after the start of gas sensor warm-up. When the decrease rate is lower than the predetermined reference value, the sixth aspect of the present invention concludes that the oxygen pump cell is deteriorated. Consequently, the present invention makes it possible to form a deterioration judgment about the oxygen pump cell early and accurately in accordance with the cell output decrease rate.

When the oxygen pump cell deteriorates, the oxygen decomposition capability, that is, the excess oxygen discharge capacity, decreases. Thus, the gas concentration detection cell detects high-concentration oxygen at all times, thereby increasing the integrated value of the cell output. The seventh aspect of the present invention acquires the integrated value of the cell output that is reached during the interval between the instant at which gas sensor warm-up starts and the instant at which an inflection point appears. When the integrated value is greater than the predetermined reference value, the seventh aspect of the present invention concludes that the oxygen pump cell is deteriorated. Consequently, the present invention makes it possible to form a deterioration judgment about the oxygen pump cell early and accurately in accordance with the integrated value of the cell output.

The time at which an inflection point appears in the cell output of the gas concentration detection cell is the time at which the excess oxygen remaining in the measurement target gas is removed by the excess oxygen removal means to the extent that the cell output of the gas concentration detection cell remains unaffected. In other words, the inflection point cell output is free from sensor output error that may be caused by the remaining excess oxygen. The learned value concerning the inflection point cell output is a value that is obtained, for instance, after the learning of individual sensor differences in the inflection point cell output. The eighth aspect of the present invention forms a deterioration judgment about the gas sensor in accordance with a comparison between the inflection point cell output and the learned value. Consequently, the present invention makes it possible to form a deterioration judgment while the influence of the remaining excess oxygen is reduced to eliminate, for instance, the influence of individual sensor differences.

When the inflection point cell output is smaller than the learned value and the deviation between the learned value and the inflection point cell output is greater than the predetermined reference value, the ninth aspect of the present invention concludes that the gas sensor is deteriorated. When the inflection point cell output is considerably smaller than the learned value, it can be concluded that the gas sensor is deteriorated or otherwise abnormal. Therefore, the present invention makes it possible to form a deterioration judgment about the gas sensor early and accurately.

When the inflection point cell output is greater than the learned value and the absolute value of the deviation between the learned value and the inflection point cell output is greater than the predetermined reference value, the tenth aspect of the present invention concludes that the gas sensor is deteriorated. When the inflection point cell output is considerably greater than the learned value, it can be concluded that the gas sensor is deteriorated or otherwise abnormal. Therefore, the present invention makes it possible to form a deterioration judgment about the gas sensor early and accurately.

Gas sensor deterioration can be classified into unrecoverable permanent deterioration and recoverable temporary deterioration depending on the degree of electrode oxidation. The eleventh aspect of the present invention forms a recoverable temporary deterioration judgment about the gas sensor in accordance with a comparison between the inflection point cell output and the learned value. There is a correlation between electrode oxidation and inflection point cell output. Therefore, the present invention can judge the degree of electrode oxidation by comparing the inflection point cell output and learned value. This makes it possible to form a recoverable temporary deterioration judgment about the gas sensor with high accuracy.

The higher the degree of oxidation of a gas sensor cell electrode, the more likely reduction reaction occurs at the electrode, and thus the greater the cell output. When the absolute value of the deviation between the learned value and the inflection point cell output is smaller than the predetermined reference value, the twelfth aspect of the present invention judges that the gas sensor is temporarily deteriorated. When the gas sensor is judged to be deteriorated but its cell output is not considerably increased, it can be concluded that the deterioration is recoverable because the degree of electrode oxidation is low. Therefore, the present invention makes it possible to conclude that the gas sensor whose inflection point cell output is close to the learned value is temporarily deteriorated.

When the gas sensor is judged to be temporarily deteriorated, the thirteenth aspect of the present invention performs a deterioration recovery process on the gas sensor. Therefore, the present invention forms a gas sensor deterioration judgment while distinguishing between permanent deterioration and recoverable deterioration, and performs a recovery process only when the gas sensor is temporarily deteriorated. This makes it possible to effectively avoid the execution of an unnecessary recovery process and recover the original performance of the gas sensor.

When the cell output is smaller than the learned value and the deviation between the learned value and the cell output is smaller than the predetermined reference value, the fourteenth aspect of the present invention stores the cell output as an updated learned value. Therefore, the present invention makes it possible to effectively acquire an output deviation due, for instance, to individual gas sensor differences as a learned value.

During an oxygen concentration decrease process that is performed after the oxygen concentration is made higher than the predetermined value by the oxygen concentration increase means, the fifteenth aspect of the present Invention identifies an inflection point appearing in the cell output of the gas concentration detection cell as an activation point. Unlike a common sensor activity (full activity) judgment, according to the fifteenth aspect of the present invention, the gas concentration detection cell is judged to be active when the gas concentration detection cell begins to detect the concentration of a specific gas component without being affected by the remaining oxygen. This makes it possible to form an accurate activity judgment about the gas concentration detection cell. Further, the fifteenth aspect of the present invention stores the inflection point learned value that is the information about the inflection point. The inflection point learned value can be used to reduce activity judgment variations due to the operating status of an internal combustion engine. Therefore, the present invention makes it possible to improve the accuracy of deterioration judgment by forming a deterioration judgment in accordance with the inflection point learned value.

The sixteenth aspect of the present invention corrects the cell output of the gas concentration detection cell by using an estimated NOx concentration value, and locates an inflection point in accordance with the corrected cell output. Therefore, the present invention makes it possible to locate an inflection point accurately without being affected by NOx concentration changes. Further, the information about the located inflection point is stored as an inflection point learned value. Consequently, the present invention makes it possible to effectively improve the accuracy of deterioration judgment by forming a deterioration judgment in accordance with the inflection point learned value.

According to the seventeenth aspect of the present invention, the oxygen concentration of the gas concentration detection cell can be increased by making the amount of power applied to the heater during a fuel cut smaller than during a normal operation. This makes it possible to locate an inflection point during a fuel cut as well and ensure sufficient learning frequency.

According to the eighteenth aspect of the present invention, the oxygen concentration of the gas concentration detection cell can be increased by making the amount of power applied to the oxygen pump cell during a fuel cut smaller than during a normal operation. This makes it possible to locate an inflection point during a fuel cut as well and ensure sufficient learning frequency.

The nineteenth aspect of the present invention locates an inflection point while the concentration of NOx in the measurement target gas is controlled. Therefore, the present invention makes it possible to locate an inflection point accurately without being affected by NOx concentration changes.

The twentieth aspect of the present invention uses a map to store the gas concentration detection cell output prevailing when an inflection point is located, a physical property value correlated to the element temperature, and the time required for inflection point location. The individual sensor differences in the physical property value are minimized when an inflection point is located. Therefore, using the map as a learned value makes it possible to reduce activity judgment variations due to the operating status of an internal combustion engine.

BEST MODE FOR CARRYING OUT THE INVENTION

Figure 1:
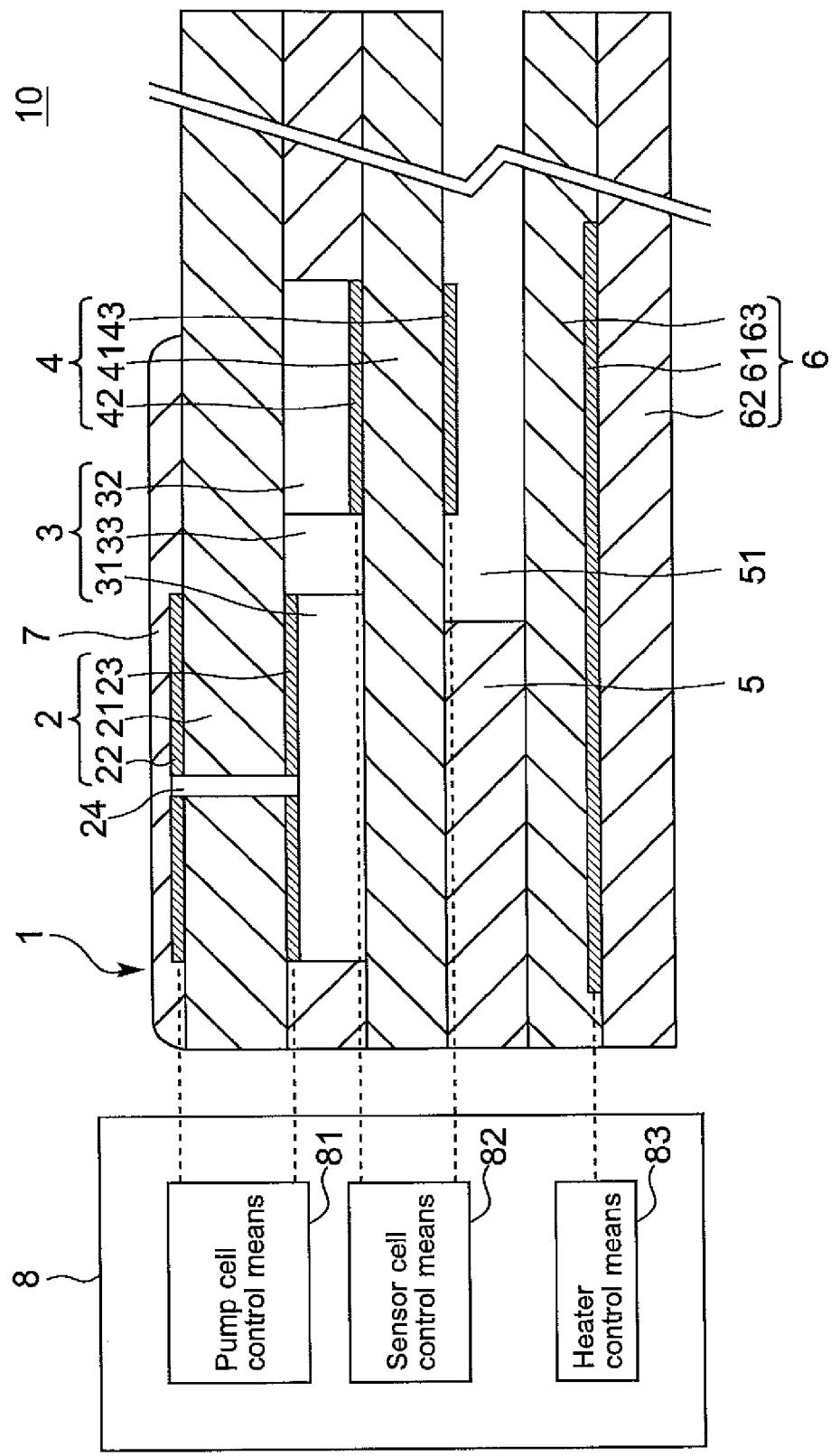
FIG. 1 is a diagram illustrating the configuration of a gas concentration detection apparatus 10 according to a first embodiment of the present invention.

Embodiments of the present invention will now be described with reference to the accompanying drawings. Like elements in the drawings are designated by the same reference numerals and will not be redundantly described. It should be understood that the present invention is not limited to the embodiments described below.

First Embodiment

Configuration of First Embodiment

First of all, the configuration of a gas concentration detection apparatus according to a first embodiment of the present invention will be described with reference to FIG. 1. FIG. 1 is a diagram illustrating the configuration of the gas concentration detection apparatus 10 according to the first embodiment. The gas concentration detection apparatus 10 shown in FIG. 1 is a NOx concentration detection apparatus that detects the concentration of a nitrogen oxide (NOx) in an exhaust gas emitted, for instance, from an internal combustion engine (hereinafter referred to as the engine).

The gas concentration detection apparatus 10 includes a NOx sensor 1. The NOx sensor 1 is formed by sequentially stacking a spacer 3, a NOx sensor cell 4, another spacer 5, and a heater 6 under an oxygen pump cell 2.

The oxygen pump cell 2 is capable of removing excess oxygen from a measurement target gas, and includes a solid electrolyte body 21, a first pump electrode 22, and a second pump electrode 23. The solid electrolyte body 21 is sandwiched between the first pump electrode 22 and the second pump electrode 23. The solid electrolyte body 21, which is an element, is oxygen ion conductive. It is shaped like a sheet that is made, for instance, of $ZrO_2$, $HfO_2$, $ThO_2$, and $BiO_2$. The first pump electrode 22 and the second pump electrode 23, which sandwich the solid electrolyte body 21, can be formed, for instance, by a screen printing method.

The first pump electrode 22, which is formed on the front surface of the solid electrolyte body 21, is exposed to a space where the exhaust gas, which is the measurement target gas, exists, that is, exposed to a space within an exhaust path of the engine. For example, a porous cermet electrode containing Pt or other noble metal may be used as the first pump electrode 22.

On the other hand, the second pump electrode 23, which is formed on the back surface of the solid electrolyte body 21 to face the first pump electrode 22, is exposed to a later-described first internal space 31. An electrode inert to a gas containing NOx, such as a porous cermet electrode containing a Pt—Au alloy and zirconia, alumina, or other ceramic material, may be used as the second pump electrode 23.

A pinhole 24 is formed in the oxygen pump cell 2 as an introduction hole that penetrates the solid electrolyte body 21, the first pump electrode 22, and the second pump electrode 23. The diameter of the pinhole 24 is designed so that the exhaust gas to be introduced into the later-described first internal space 31 through the pinhole 24 diffuses at a predetermined rate. Through the pinhole 24 and a later-described porous protective layer 7, the first internal space 31 communicates with a space where the measurement target gas exists.

The porous protective layer 7 is formed on the side toward the first pump electrode 22 of the solid electrolyte body 21 so as to cover the surface of the first pump electrode 22, including the pinhole 24, and its surrounding area. The porous protective layer 7 may be made, for instance, of porous alumina. The porous protective layer 7 makes it possible to not only prevent the first pump electrode 22 from being poisoned, but also prevent the pinhole 24 from being clogged, for instance, by soot contained in the exhaust gas.

The aforementioned first internal space 31 and a second internal space 32 are formed in the spacer 3. The spacer 3 may be made, for instance, of alumina. The two internal spaces 31, 32 communicate with each other through a communication hole 33. The first internal space 31, the second internal space 32, and the communication hole 33 can be formed by making a through hole in the spacer 3.

The NOx sensor cell 4 detects a NOx concentration from the amount of oxygen derived from the reductive decomposition of NOx. The NOx sensor cell 4 includes a solid electrolyte body 41, a first detection electrode 42, and a second detection electrode 43. The solid electrolyte body 41 is sandwiched between the first detection electrode 42 and the second detection electrode 43. The first detection electrode 42 and the second detection electrode 43 can be formed, for instance, by a screen printing method.

The first detection electrode 42, which is formed on the front surface of the solid electrolyte body 41, is exposed to the second internal space 32. For example, a porous cermet electrode containing a Pt—Au alloy and zirconia, alumina, or other ceramic material may be used as the first detection electrode 42.

On the other hand, the second detection electrode 43, which is formed on the back surface of the solid electrolyte body 41 to face the first detection electrode 42, is exposed to a space within an atmosphere duct 51, which is formed in the spacer 5. Atmospheric air is introduced into the atmosphere duct 51. For example, a porous cermet electrode containing Pt or other noble metal may be used as the second detection electrode 43. The atmosphere duct 51 can be formed by making a notch in the spacer 5.

The heater 6 includes sheet-shaped insulation layers 62, 63 and a heater electrode 61, which is buried between the insulation layers 62, 63. The insulation layers 62, 63 are formed, for instance, by a ceramic material such as alumina. The heater electrode 61 is formed, for instance, by a cermet that is made of Pt and alumina or other ceramic material.

The gas concentration detection apparatus 10 according to the first embodiment includes an ECU (Electronic Control Unit) 8, which serves as a control device. The ECU 8 includes pump cell control means 81, sensor cell control means 82, and heater control means 83. The ECU 8 may be provided in addition to an engine control ECU or provided as a part of the engine control ECU.

The pump cell control means 81 is connected to the first pump electrode 22 and the second pump electrode 23, which are included in the oxygen pump cell 2. The pump cell control means 81 applies a voltage between the first pump electrode 22 and the second pump electrode 23, and detects the value of a current flowing in the oxygen pump cell 2 as an "oxygen pump cell output."

The sensor cell control means 82 is connected to the first detection electrode 42 and the second detection electrode 43, which are included in the NOx sensor cell 4. The sensor cell control means 82 applies a voltage between the first detection electrode 42 and the second detection electrode 43 and detects the value of a current flowing in the NOx sensor cell 4 as a "NOx sensor cell output."

The heater control means 83 is connected to the heater electrode 61. The heater control means 83 supplies electrical power to the heater electrode 61.

[Operation of First Embodiment]
(Principles of NOx Concentration Detection)

The principles of NOx concentration detection by the gas concentration detection apparatus 10 will now be described with reference to FIG. 1. Exhaust gas, which is a measurement target gas flowing in the exhaust path of the engine, exists in a space around the porous protective layer 7. The exhaust gas includes, for instance, $O_2$, NOx, $CO_2$, and $H_2O$. The exhaust gas is introduced into the first internal space 31 through the porous protective layer 7 and pinhole 24. The amount of exhaust gas to be introduced into the first internal space 31 is determined by the diffusion resistance of the porous protective layer 7 and pinhole 24.

Before NOx concentration detection, the heater control means 83 first supplies electrical power to the heater electrode 61 to heat the solid electrolyte bodies 21, 41 to their activity temperature. The oxygen pump cell 2 then becomes active so that the pump cell control means 81 applies a voltage between the first pump electrode 22 and the second pump electrode 23. On the second pump electrode 23, which is exposed to the first internal space 31, remaining oxygen and oxygen contained in the exhaust gas are then reduced to oxygen ions $O^{2-}$. The oxygen ions $O^{2-}$ are then pumped out toward the first pump electrode 22 through the solid electrolyte body 21. In this instance, the pump cell control means 81 detects the value of a current flowing in the oxygen pump cell 2 as the oxygen pump cell output. When excess oxygen is discharged by the oxygen pump cell 2, the concentration of oxygen in the exhaust gas decreases to the extent that NOx concentration detection by the NOx sensor cell 4 remains unaffected. Maximizing the voltage applied between the first pump electrode 22 and the second pump electrode 23 makes the pumping operation for oxygen ions $O^{2-}$ more vigorous to increase the amount of oxygen to be discharged.

The exhaust gas from which excess oxygen is removed to decrease the oxygen concentration is introduced into the second internal space 32 through the communication hole 33. When the NOx sensor cell 4 becomes active so that the sensor cell control means 82 applies a voltage between the first detection electrode 42 and the second detection electrode 43, NOx, which is a specific component of the exhaust gas, is decomposed on the first detection electrode 42 to generate oxygen ions $O^{2-}$. More specifically, NOx is first decomposed to NO (converted to a single gas component) and then further decomposed to oxygen ions $O^{2-}$. The oxygen ions $O^{2-}$ pass through the solid electrolyte body 41 and are discharged from the second detection electrode 43 to the atmosphere duct 51. In this instance, the sensor cell control means 82 detects a current flowing in the NOx sensor cell 4 as the NOx sensor cell output, that is, the NOx concentration output for the measurement target gas.

(NOx Sensor Activity Judgment Operation)

An activity judgment operation concerning the NOx sensor 1 will now be described with reference to FIGS. 2 and 3. To achieve the abovementioned NOx concentration detection with high accuracy, it is necessary that the NOx sensor 1 be in its active state. The "active state" according to the present invention is a state where the detection of a NOx sensor output unaffected by the remaining oxygen is initiated, that is, the NOx sensor cell output can be used for various control operations without being affected by the remaining oxygen (the same holds true for later-described embodiments). Therefore, when an activity judgment about the NOx sensor 1 can be formed early, the NOx sensor cell output can be immediately used for various control operations to reduce emissions.

To obtain normal characteristics from the NOx sensor 1 or other similar NOx sensor having an element made of a solid electrolyte body, it is necessary to energize a heater to raise the element temperature to a predefined activity temperature. It is known that an activity judgment about a gas concentration sensor is formed in accordance, for instance, with element impedance, power supplied to the heater, or heater resistance. However, the element impedance and the power supplied to the heater, for example, vary from one sensor unit to another. It is therefore difficult to accurately and immediately grasp the sensor's active state in accordance with the above parameters.

In view of the above circumstances, the first embodiment forms an activity judgment about the NOx sensor 1 early and accurately in the manner described below. FIG. 2 is a diagram illustrating how the oxygen pump cell output and NOx sensor cell output change during NOx sensor warm-up. In FIG. 2, a broken line Lp indicates changes in the oxygen pump cell output whereas a solid line Ls indicates changes in the NOx sensor cell output.

Figure 2:
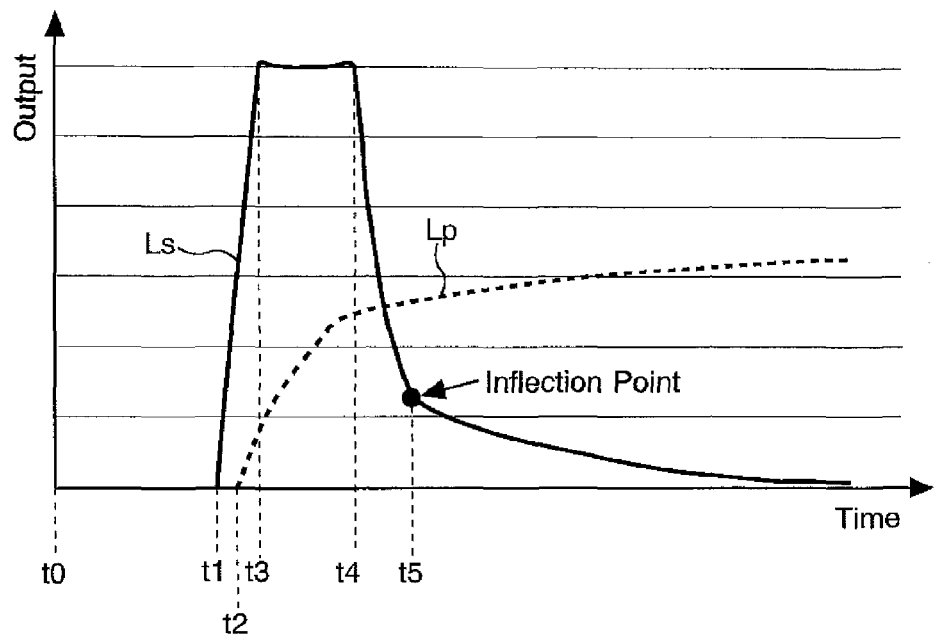
FIG. 2 is a diagram illustrating changes in an oxygen pump cell output and a NOx sensor cell output during NOx sensor warm-up.

At time t0, the NOx sensor 1 begins to warm up at engine start as shown in FIG. 2. More specifically, the heater control means 83 begins to apply electrical power to the heater electrode 61. As a result of such power application, the temperatures of the oxygen pump cell 2 and NOx sensor cell 4, namely, the temperatures of the solid electrolyte bodies 21, 41 gradually rise. At time t0, oxygen contained in atmospheric air remains in the first internal space 31, which is near the oxygen pump cell 2, and in the second internal space 32, which is near the NOx sensor cell 4.

Subsequently, when the solid electrolyte body 41 of the NOx sensor cell 4 reaches a predetermined temperature at time t1, a NOx sensor cell output is obtained. After time t1, the NOx sensor cell output increases with an increase in the activity of the NOx sensor cell 4 (solid electrolyte body 41). This is because the oxygen remaining in the second internal space 32 is decomposed at the first detection electrode 42 and not because the NOx introduced into the second internal space 32, which is near the NOx sensor cell 4, is decomposed at the first detection electrode 42. Then, at time t3, the NOx sensor cell output reaches an upper limit value, that is, the upper limit value of oxygen concentration that can be detected by the NOx sensor cell 4.

Meanwhile, when the solid electrolyte body 21 of the oxygen pump cell 2 reaches a predetermined temperature at time t2, which is subsequent to time t1, an oxygen pump cell output is obtained. After time t2, the discharge amount of oxygen remaining in the first internal space 31, which is near the oxygen pump cell 2, increases with an increase in the activity of the oxygen pump cell 2 (solid electrolyte body 21). Therefore, the oxygen pump cell output increases with time.

The amount of oxygen discharged from the first internal space 31 increases with an increase in the activity of the oxygen pump cell 2. Further, the amount of exhaust gas introduced into the first internal space 31 increases with an increase in the activity of the oxygen pump cell 2. This lowers the concentration of oxygen remaining in the first internal space 31 and decreases the amount of oxygen supplied from the first internal space 31 to the second internal space 32. Therefore, the concentration of oxygen remaining in the second internal space 32 gradually decreases with an increase in the activity of the oxygen pump cell 2. As a result, the NOx sensor cell output decreases after time t4.

Subsequently, at time t5 at which the oxygen remaining in the second internal space 32 is substantially removed, an inflection point appears in the NOx sensor output to represent a point at which a curve indicative of the NOx sensor cell output greatly changes. More specifically, the NOx sensor cell output generated before the appearance of the inflection point mainly uses the oxygen remaining in the second internal space 32 to perform an oxygen ion pumping operation. Therefore, the curve indicative of the NOx sensor cell output prevailing during such a period is predominantly affected by the concentration of oxygen in the second internal space 32, that is, the activity of the oxygen pump cell 2.

On the other hand, the NOx sensor cell output generated after the appearance of the inflection point mainly uses the NOx in the second internal space 32 to perform an oxygen ion pumping operation because the remaining oxygen is decreased. Therefore, the curve indicative of the NOx sensor cell output prevailing during such a period is predominantly affected by the concentration of NOx in the second internal space 32, that is, the activity of the NOx sensor cell 4. Consequently, at time t5 at which the inflection point appears, it is possible to recognize that the oxygen remaining in the first and second internal spaces 31, 32 before the warm-up of the NOx sensor 1 is substantially removed. Thus, after time t5 at which the inflection point appears, the NOx sensor cell 4 can accurately detect the NOx concentration without being affected by the remaining oxygen.

Consequently, the first embodiment forms an activity judgment about the NOx sensor 1 at time t5 at which an inflection point appears in the NOx sensor cell output. This makes it possible to form an activity judgment about the NOx sensor 1 when the NOx sensor cell 4 begins to detect the NOx concentration without being affected by the remaining oxygen. Therefore, the demand for early activation of the NOx sensor 1 can be satisfied to the utmost extent.

An operation performed to locate the above-described inflection point will now be described with reference to FIG. 3. FIG. 3 is a diagram illustrating a method of locating the inflection point in the NOx sensor cell output. As shown in the figure, the first step is to acquire the NOx sensor cell output N at predetermined time intervals and calculate a NOx sensor cell output change amount $\Delta N$ upon each NOx sensor cell output acquisition. The amount of change $\Delta N(t)$ at time t can be calculated from Equation (1) below. When the calculated change amount $\Delta N(t)$ is smaller than a predetermined reference value $\Delta Nth$ during a process in which the NOx sensor cell output N decreases, the NOx sensor cell output $N(t)$ prevailing at time t is identified as an inflection point.

$$\Delta N(t)=|N(t)-N(t-1)| \tag{1}$$

Figure 3:
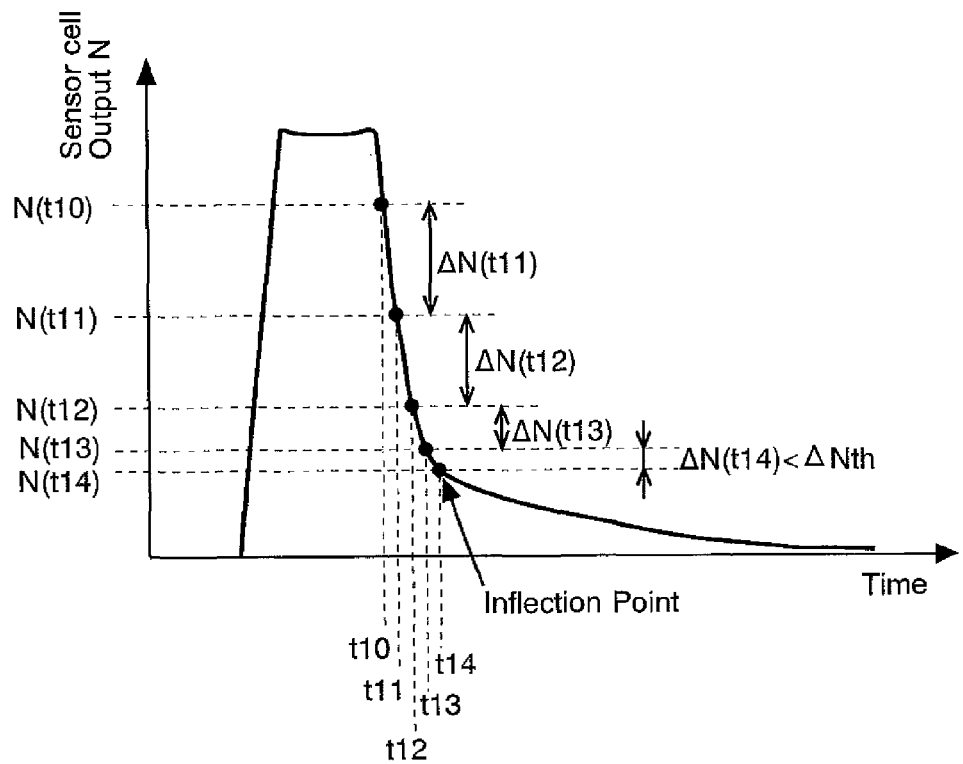
FIG. 3 is a diagram illustrating a method of locating an inflection point in the NOx sensor cell output.

The example shown in FIG. 3 indicates that the NOx sensor cell output N decreases during the period between time t10 and time t14. In other words, $N(t)-N(t-1)$ in Equation (1) above is negative at time t11, time t12, time t13, and time t14. The change amounts $\Delta N(t11)$ to $\Delta N(t13)$ are not smaller than the predetermined reference value $\Delta Nth$. However, the change amount $\Delta N(t14)$ is smaller than the reference value $\Delta Nth$. Therefore, the NOx sensor cell output $N(t14)$ prevailing at time t14 is identified as an inflection point. Thus, an activity judgment about the NOx sensor 1 is formed at time t14 at which the inflection point appears in the NOx sensor cell output.

A method of locating the inflection point is not limited to the above-described one. For example, the NOx sensor cell output N prevailing when the NOx sensor cell output N stops decreasing and starts increasing may alternatively be identified as an inflection point. The reason is that an increase in the concentration of NOx in the exhaust gas means that such an increase is detected by the NOx sensor cell 4. Further, when the NOx sensor cell output N is smaller than the reference value Nth, the NOx sensor cell output N may be identified as an inflection point even in a situation where the amount of change $\Delta N$ in the NOx sensor cell output N is greater than the reference value $\Delta Nth$. The reason is that it means that the remaining oxygen is removed before the NOx sensor 1 is completely warmed up.

[Characteristic Operation of First Embodiment]

Figure 4:
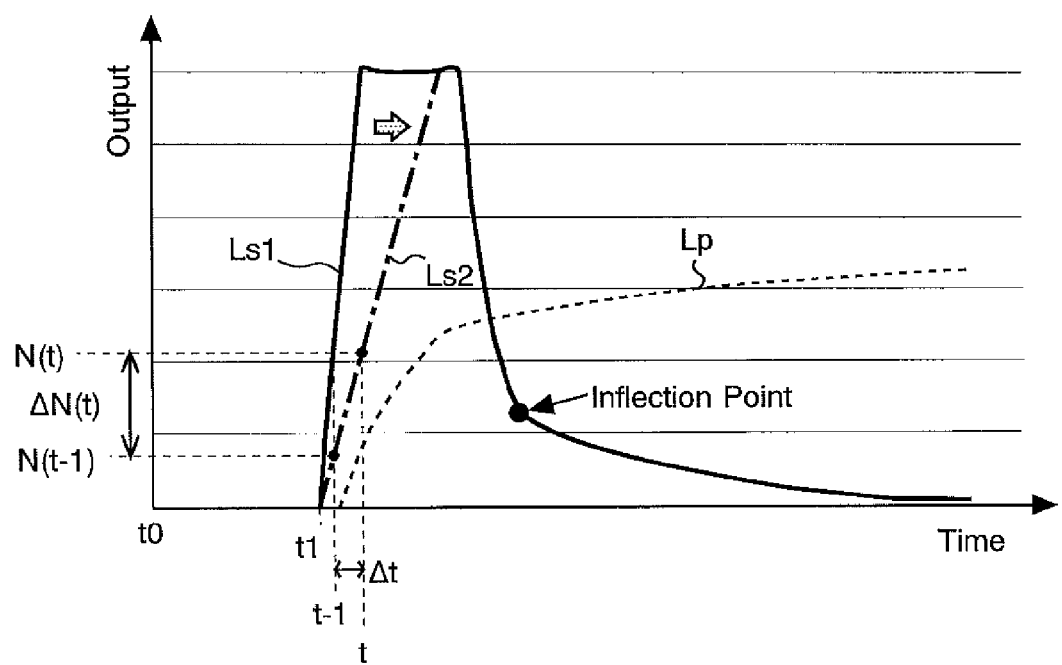
FIG. 4 is a diagram illustrating how the NOx sensor cell output N changes when a NOx sensor cell 4 deteriorates.

A characteristic operation of the present embodiment will now be described with reference to FIG. 4. As mentioned earlier, it is possible to recognize at the time of inflection point appearance that the oxygen remaining in the first and second internal spaces 31, 32 before the warm-up of the NOx sensor 1 is substantially removed. After the appearance of the inflection point, therefore, the NOx sensor cell 4 can detect the NOx concentration without being affected by the remaining oxygen.

When the NOx sensor cell 4 in the NOx sensor 1 deteriorates, the NOx sensor cell output N prevailing before the inflection point changes. FIG. 4 is a diagram illustrating how the NOx sensor cell output N changes in the event of NOx sensor cell 4 deterioration. In FIG. 4, a broken line Lp indicates changes in the oxygen pump cell output; a solid line Ls1 indicates output changes in a normal NOx sensor cell 4; and a one-dot chain line Ls2 indicates output changes in a deteriorated NOx sensor cell 4.

When, at time t0, the NOx sensor 1 begins to warm up at engine start as indicated by the solid line Ls1 in the figure, the temperature of the solid electrolyte body 41 in the NOx sensor cell 4 gradually rises. Then, after time t1, the NOx sensor cell output increases with an increase in the activity of the NOx sensor cell 4 (solid electrolyte body 41). The reason is that the excess oxygen remaining in the second internal space 32 is decomposed at the first detection electrode as described earlier.

In the NOx sensor 1 whose NOx sensor cell 4 is deteriorated, the oxygen decomposition capability of the NOx sensor cell 4 is reduced. Therefore, a deteriorated NOx sensor 1 exhibits a lower increase rate of the NOx sensor cell output N than a normal NOx sensor 1 as indicated by the one-dot chain line Ls2 in the figure.

Consequently, the present embodiment forms a deterioration judgment about the NOx sensor 1 in accordance with the above-described output tendency. More specifically, the NOx sensor cell output $N(t)$ is first acquired at predetermined time intervals $\Delta t$ during an increase in the NOx sensor cell output N as shown in the figure. The amount of change $\Delta N(t)$ in the NOx sensor cell output is then computed from Equation (1) upon each NOx sensor cell output acquisition. Next, the output increase rate $Vu(t)$ of the NOx sensor cell output N is computed by substituting the change amount $\Delta N(t)$, which is determined upon each NOx sensor cell output acquisition, into Equation (2) below. When the computed output increase rate $Vu(t)$ is smaller than a predetermined reference value $Vth1$, the NOx sensor cell 4 in the NOx sensor 1 is checked for deterioration.

$$Vu(t)=\Delta N(t)/\Delta t \qquad (2)$$

As described above, the gas concentration detection apparatus according to the first embodiment forms a deterioration judgment about the NOx sensor cell 4 during a process for locating an inflection point that appears in the NOx sensor cell output N. This makes it possible to accurately check for deterioration of the NOx sensor 1 before it becomes active.

[Details of Process Performed by First Embodiment]

Figure 5:
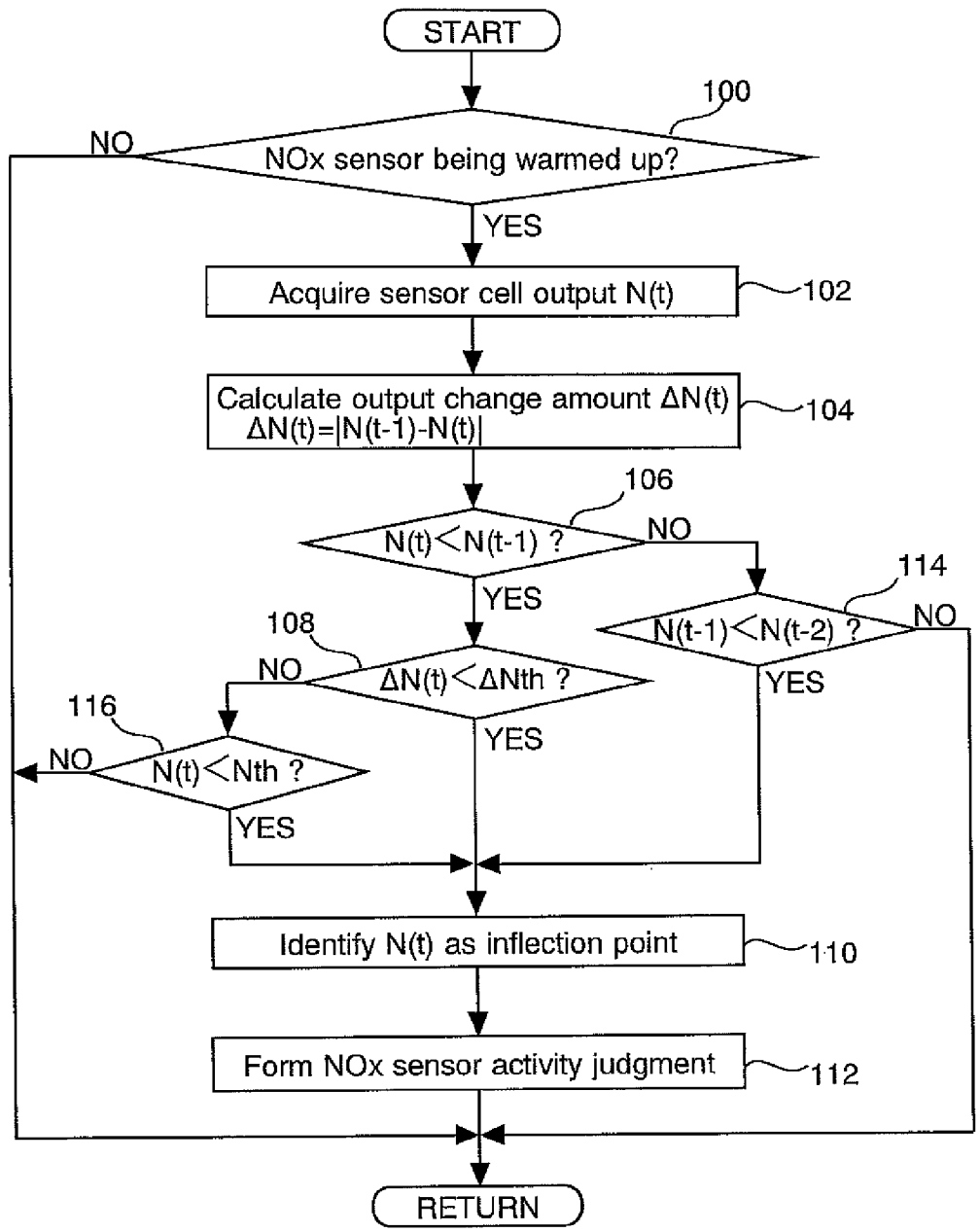
FIG. 5 is a flowchart illustrating a routine that an ECU 8 executes in accordance with the first embodiment of the present invention.

A process performed by the first embodiment will now be described in detail with reference to FIGS. 5 and 6. FIG. 5 is a flowchart illustrating a routine that the ECU 8 executes to form an activity judgment about the NOx sensor 1 in accordance with the first embodiment. The routine starts at predetermined intervals. The predetermined intervals correspond, for instance, to the interval between time t10 and time t11 and the interval between time t11 and time t12, which are shown in FIG. 3.

First of all, the routine shown in FIG. 5 performs step 100 to judge whether the NOx sensor 1 is warming up. More specifically, step 100 is performed to judge whether the engine is starting to warm up the NOx sensor 1 or whether recovery is being made from a prolonged fuel cut. If the judgment result obtained in step 100 does not indicate that the NOx sensor 1 is warming up, the routine comes to an immediate end because it concludes that the NOx sensor cell output shown in FIG. 2 cannot be obtained.

If, on the other hand, the judgment result obtained in step 100 indicates that the NOx sensor 1 is warming up, the routine proceeds to the next step (step 102) and acquires a NOx sensor cell output $N(t)$. Next, the routine performs step 104 to calculate a change amount $\Delta N(t)$. More specifically, step 104 is performed to compute the change amount $\Delta N(t)$ by substituting the NOx sensor cell output $N(t)$ obtained in step 102 and $N(t-1)$ into Equation (1) above.

Next, the routine performs step 106 to judge whether the NOx sensor cell output $N(t)$ is smaller than $N(t-1)$. More specifically, step 106 is performed to compare the NOx sensor cell output $N(t)$, which is obtained in step 102, against $N(t-1)$. If the judgment result obtained in step 106 indicates that $N(t)<N(t-1)$, the routine concludes that an output decrease process is being performed to decrease the NOx sensor cell output $N(t)$, proceeds to the next step (step 108), and judges whether the change amount $\Delta N(t)$ is smaller than the reference value $\Delta Nth$. If the judgment result obtained in step 108 indicates that the change amount $\Delta N(t)$ is smaller than the reference value $\Delta Nth$, the routine proceeds to the next step (step 110) and identifies the NOx sensor cell output $N(t)$ as an inflection point. In the example shown in FIG. 3, the NOx sensor cell output $N(t14)$ prevailing at time t14 is identified as an inflection point because the change amount $\Delta N(t14)$ is smaller than the reference value $\Delta Nth$. The routine then performs step 112 to conclude that the activity time of the NOx sensor cell 4 is represented by the time at which the inflection point is encountered. Upon completion of step 112, the routine terminates.

If, on the other hand, the judgment result obtained in step 106 does not indicate that $N(t)<N(t-1)$, the routine concludes that the NOx sensor cell output $N(t)$ is increased, proceeds to the next step (step 114), and judges whether the NOx sensor cell output $N(t-1)$ determined by the last routine is smaller than $N(t-2)$. More specifically, step 114 is performed to compare the NOx sensor cell output $N(t-1)$ determined by the last routine against the NOx sensor cell output $N(t-2)$ determined by the second last routine. If the comparison does not indicate that $N(t-1)<N(t-2)$, the NOx sensor cell output N is rising toward the upper limit value. Therefore, the routine concludes that an inflection point is still not encountered, and then comes to an immediate end.

If, on the other hand, the judgment result obtained in step 114 indicates that $N(t-1)<N(t-2)$, the routine concludes that the NOx sensor cell output $N(t-2)$ determined by the second last routine is greater than the change amount $\Delta(t-1)$ determined by the last routine. In this instance, the current routine judges that an increase in the concentration of NOx in the exhaust gas is currently detected, proceeds to step 110, and identifies the NOx sensor cell output $N(t)$ as an inflection point.

If the judgment result obtained in step 108 does not indicate that the change amount $\Delta N(t)$ is smaller than the reference value $\Delta Nth$, the routine proceeds to the next step (step 116) and judges whether the NOx sensor cell output $N(t)$ is smaller than the reference value $\Delta Nth$. If the obtained judgment result does not indicate that the NOx sensor cell output $N(t)$ is smaller than the reference value $\Delta Nth$, the routine comes to an immediate end because it concludes that an inflection point has still not appeared in the NOx sensor cell output N.

If, on the other hand, the judgment result obtained in step 116 indicates that the NOx sensor cell output $N(t)$ is smaller than the reference value $\Delta Nth$, the routine proceeds to step 110 and identifies the NOx sensor cell output $N(t)$ as an inflection point.

Figure 6:
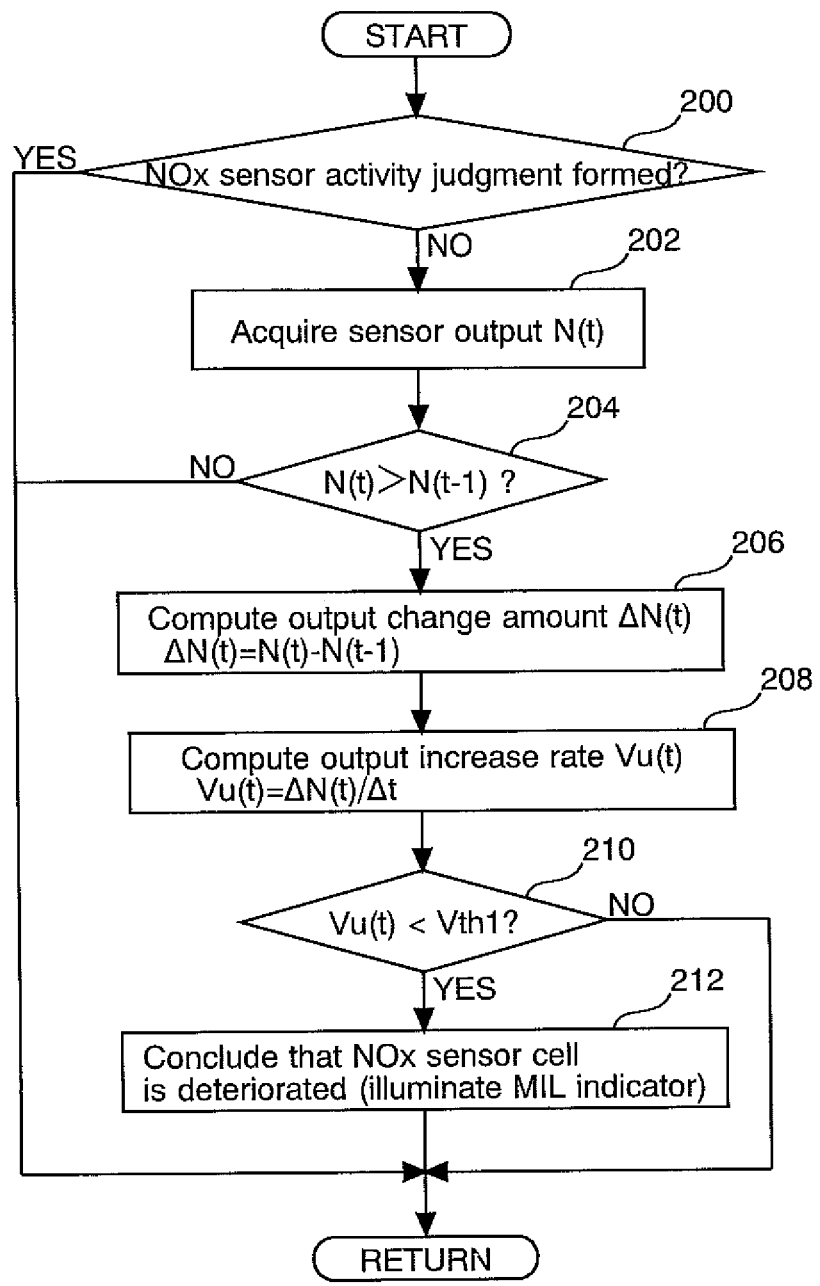
FIG. 6 is a flowchart illustrating a routine that the ECU 8 executes in accordance with the first embodiment of the present invention.

FIG. 6 is a flowchart illustrating a routine that the ECU 8 executes in accordance with the first embodiment to form a deterioration judgment about the NOx sensor 1, or more specifically, a deterioration judgment about the NOx sensor cell 4. This routine starts at predetermined intervals together with the routine shown in FIG. 5. First of all, the routine shown in FIG. 6 performs step 200 to perform an activity judgment process on the NOx sensor 1. More specifically, step 200 is performed to judge whether an activity judgment is formed by the routine shown in FIG. 5, which is executed together with the currently executed routine, that is, whether an activity judgment about the NOx sensor 1 is formed in step 112. If the obtained judgment result indicates that an activity judgment about the NOx sensor 1 is formed, the routine comes to an immediate end.

If, on the other hand, the judgment result obtained in step 200 does not indicate that an activity judgment about the NOx sensor 1 is formed, the routine concludes that the NOx sensor 1 is still not activated, proceeds to the next step (step 202), and acquires the NOx sensor cell output N(t). More specifically, the process performed in step 202 is the same as the process performed in step 102 of the routine shown in FIG. 5.

Next, the routine performs step 204 to judge whether the NOx sensor cell output N is increasing. More specifically, step 204 is performed to judge whether the NOx sensor cell output N(t) acquired in step 202 above is greater than N(t−1), which is acquired in step 202 of the last routine. If the obtained judgment result does not indicate that N(t)>N(t−1), the routine concludes that the NOx sensor cell output N is decreased, and then comes to an immediate end.

If, on the other hand, the judgment result obtained in step 204 indicates that N(t)>N(t−1), the routine concludes that the NOx sensor cell output N is increased, proceeds to the next step (step 206), and acquires the change amount ΔN(t). More specifically, the process performed in step 206 is the same as the process performed in step 104 of the routine shown in FIG. 5.

Next, the routine performs step 208 to compute the output increase rate Vu(t). More specifically, the output increase rate Vu(t) is computed in step 208 by substituting the change amount ΔN(t) computed in step 206 into Equation (2) above.

Next, the routine performs step 210 to judge whether the output increase rate Vu(t) is lower than a predetermined reference value Vth1. The reference value Vth1 is predetermined, for instance, by an experiment and used as a threshold value for forming a deterioration judgment about the NOx sensor cell 4. If the judgment result obtained in step 210 does not indicate that Vu(t)<Vth1, the routine concludes that the NOx sensor cell 4 is not deteriorated, and then comes to an immediate end.

If, on the other hand, the judgment result obtained in step 210 indicates that Vu(t)<Vth1, the routine concludes that the NOx sensor cell 4 is deteriorated, proceeds to the next step (step 212), and forms a deterioration judgment about the NOx sensor cell 4. More specifically, the routine performs a process in step 212 to illuminate an MIL indicator on the gas concentration detection apparatus for the purpose of announcing that the NOx sensor cell 4 is deteriorated.

As described above, the first embodiment forms a deterioration judgment about the NOx sensor cell 4 during a process that is performed to locate an inflection point in the NOx sensor cell output N. It means that a deterioration judgment is formed before the NOx sensor 1 becomes active. This makes it possible to effectively avoid a situation where the output of a deteriorated NOx sensor is used for various control operations.

The first embodiment, which has been described above, forms a deterioration judgment about the NOx sensor cell 4 in accordance with a comparison between the output increase rate Vu(t) and the predetermined reference value Vth1. However, the value for forming a deterioration judgment about the NOx sensor cell 4 is not limited to the output increase rate Vu(t). For example, the output change amount may be used for deterioration judgment as far as it correlates with the increase rate of the NOx sensor cell output N. Another alternative value for deterioration judgment would be, for instance, the output prevailing after the elapse of a predetermined time period since the start of power application to the heater 6 or the time required for obtaining a predefined output.

Further, the first embodiment, which has been described above, forms a deterioration judgment about the NOx sensor cell 4 in accordance with a comparison between the output increase rate Vu(t) and the predetermined reference value Vth1. However, the output increase rate Vu(t) may be corrected to further improve the accuracy of deterioration judgment about the NOx sensor cell 4. The output increase rate Vu(t) is affected by the concentration of oxygen remaining in the first and second internal spaces 31, 32. More specifically, the longer the soak time for the NOx sensor 1, that is, the higher the concentration of oxygen in the above-mentioned spaces, the higher the output increase rate Vu(t). Therefore, the influence of the difference in the concentration of remaining oxygen can be corrected to improve the accuracy of deterioration judgment. The above correction may be made by correcting the output increase rate Vu(t) or the reference value Vth1 in accordance with the concentration of remaining oxygen.

In the first embodiment, which has been described above, the NOx sensor 1 corresponds to the "gas sensor" according to the first aspect of the present invention; the oxygen pump cell 2 corresponds to the "oxygen concentration control means" according to the first aspect of the present invention; the NOx sensor cell 4 corresponds to the "gas concentration detection cell" according to the first aspect of the present invention; and the NOx sensor cell output corresponds to the "cell output" according to the first aspect of the present invention. The "deterioration judgment means" according to the first aspect of the present invention is implemented when the ECU 8 performs step 210.

Further, in the first embodiment, which has been described above, the NOx sensor 1 corresponds to the "gas sensor" according to the second aspect of the present invention; the oxygen pump cell 2 corresponds to the "excess oxygen removal means" according to the second aspect of the present invention; the NOx sensor cell 4 corresponds to the "gas concentration detection cell" according to the second aspect of the present invention; and the NOx sensor cell output corresponds to the "cell output" according to the second aspect of the present invention. The "deterioration judgment means" according to the second aspect of the present invention is implemented when the ECU 8 performs step 210.

Furthermore, in the first embodiment, which has been described above, the output increase rate Vu(t) corresponds to the "increase rate correlation value" according to the third aspect of the present invention. The "increase rate correlation value acquisition means" according to the third aspect of the present invention is implemented when the ECU 8 performs step 208.

Moreover, in the first embodiment, which has been described above, the output increase rate Vu(t) corresponds to the "increase rate" according to the fourth aspect of the present invention. The "increase rate acquisition means"

according to the fourth aspect of the present invention is implemented when the ECU 8 performs step 208.

Second Embodiment

Features of Second Embodiment

Figure 7:
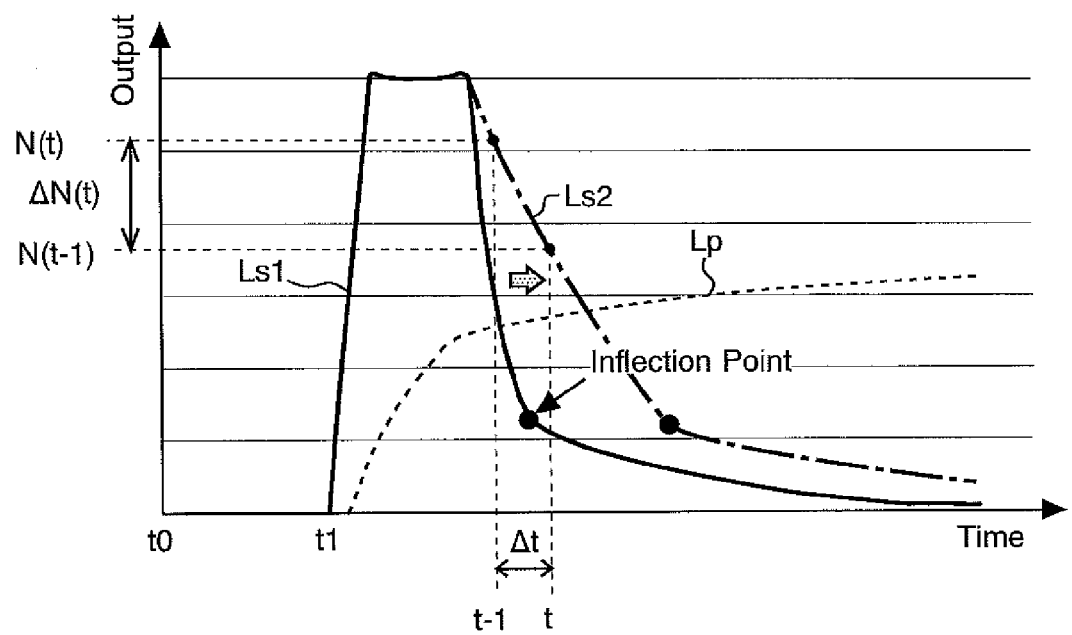
FIG. 7 is a diagram illustrating how the NOx sensor cell output N changes when an oxygen pump cell 2 deteriorates.
Figure 8:
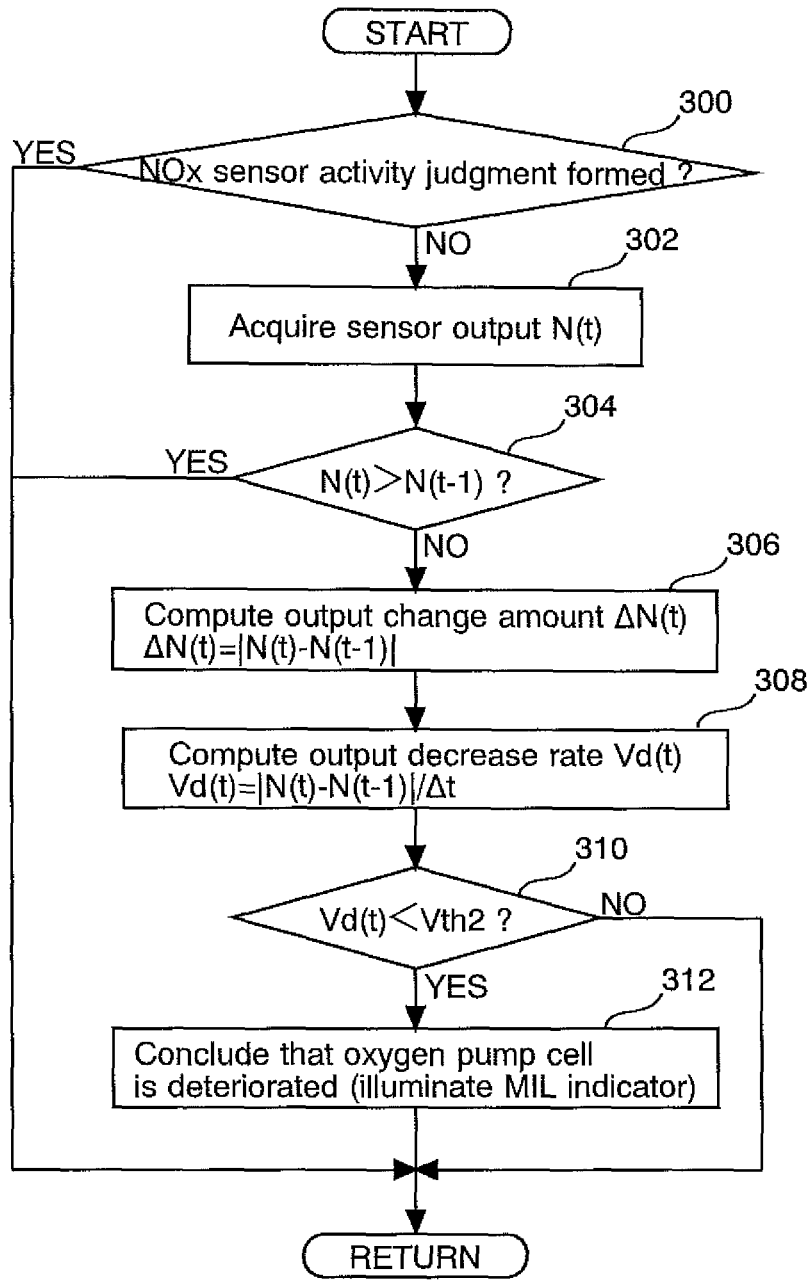
FIG. 8 is a flowchart illustrating a routine that the ECU 8 executes in accordance with a second embodiment of the present invention.

A second embodiment of the present invention will now be described with reference to FIGS. 7 and 8. A system according to the second embodiment is implemented when the hardware configuration shown in FIG. 1 is employed to let the ECU 8 execute a later-described routine shown in FIG. 8.

As described earlier, at the time at which an inflection point appears, it is possible to grasp that the oxygen remaining in the first and second internal spaces 31, 32 before the warm-up of the NOx sensor 1 is substantially removed. Therefore, after the time of inflection point appearance, the NOx sensor cell 4 can detect the NOx concentration without being affected by the remaining oxygen.

When the oxygen pump cell 2 in the NOx sensor 1 deteriorates, the NOx sensor cell output N before the inflection point changes. FIG. 7 is a diagram illustrating how the NOx sensor cell output N changes when the oxygen pump cell 2 is deteriorated. In FIG. 7, a broken line Lp indicates changes in the oxygen pump cell output; a solid line Ls1 indicates output changes in the NOx sensor cell 4 that occur when the oxygen pump cell 2 is normal; and a one-dot chain line Ls2 indicates output changes in the NOx sensor cell 4 that occur when the oxygen pump cell 2 is deteriorated.

As indicated by the solid line Ls1 in the figure, when, at time t0, the NOx sensor 1 begins to warm up at engine start, the temperature of the solid electrolyte body 41 in the NOx sensor cell 4 gradually rises. Then, after time t1, the NOx sensor cell output N increases with an increase in the activity of the NOx sensor cell 4 (solid electrolyte body 41). The reason is that the excess oxygen remaining in the second internal space 32 decomposes at the first detection electrode 42 as described earlier.

Subsequently, when the activity of the oxygen pump cell 2 increases, the excess oxygen remaining in the first and second internal spaces 31, 32 begins to decompose at the second pump electrode 23 in the oxygen pump cell 2. Thus, the amount of excess oxygen remaining in the first and second internal spaces 31, 32 decreases. Consequently, the NOx sensor cell output N begins to decrease.

If, in this instance, the oxygen pump cell 2 deteriorates, the oxygen decomposition capability of the oxygen pump cell 2 decreases. Therefore, the NOx sensor 1 having a deteriorated oxygen pump cell 2 exhibits a smaller value than the NOx sensor 1 having a normal decrease rate of the NOx sensor cell output N, as indicated by the one-dot chain line Ls2 in the figure.

Consequently, the present embodiment forms a deterioration judgment about the NOx sensor 1 in accordance with the above-described output tendency. More specifically, the NOx sensor cell output N(t) is first acquired at predetermined time intervals Δt during an decrease in the NOx sensor cell output N as shown in the figure. The amount of change ΔN(t) in the NOx sensor cell output is then computed from Equation (1) above upon each NOx sensor cell output acquisition. Next, the output decrease rate Vd(t) of the NOx sensor cell output N is computed by substituting the change amount ΔN(t), which is determined upon each NOx sensor cell output acquisition, into Equation (3) below. When the computed output decrease rate Vd(t) is smaller than a predetermined reference value Vth2, the oxygen pump cell 2 in the NOx sensor 1 is checked for deterioration.

$$Vd(t) = \Delta N(t)/\Delta t \tag{3}$$

As described above, the gas concentration detection apparatus according to the second embodiment forms a deterioration judgment about the oxygen pump cell 2 during a process for locating an inflection point that appears in the NOx sensor cell output N. This makes it possible to accurately check for deterioration of the NOx sensor 1 before it becomes active.

[Details of Process Performed by Second Embodiment]

A process performed by the second embodiment will now be described in detail with reference to FIG. 8. FIG. 8 is a flowchart illustrating a routine that the ECU 8 executes to form a deterioration judgment about the NOx sensor 1, or more specifically, a deterioration judgment about the oxygen pump cell 2, in accordance with the second embodiment. The routine starts at predetermined intervals together with the routine shown in FIG. 5. First of all, the routine shown in FIG. 8 performs step 300 to perform an activity judgment process on the NOx sensor 1. More specifically, the process performed in step 300 is the same as the process performed in step 200. If the judgment result obtained in step 300 indicates that an activity judgment about the NOx sensor 1 is formed, the routine comes to an immediate end.

If, on the other hand, the judgment result obtained in step 300 does not indicate that an activity judgment about the NOx sensor 1 is formed, the routine concludes that the NOx sensor 1 is still not activated, proceeds to the next step (step 302), and acquires the NOx sensor cell output N(t). More specifically, the process performed in step 302 is the same as the process performed in step 202.

Next, the routine performs step 304 to judge whether the NOx sensor cell output N is decreasing. More specifically, the process performed in step 304 is the same as the process performed in step 204. If the judgment result obtained in step 304 indicates that N(t)>N(t−1), the routine concludes that the NOx sensor cell output N is increased, and then comes to an immediate end.

If, on the other hand, the judgment result obtained in step 304 does not indicate that N(t)>N(t−1), the routine concludes that the NOx sensor cell output N is decreased, proceeds to the next step (step 306), and acquires the change amount ΔN(t). More specifically, the process performed in step 306 is the same as the process performed in step 206.

Next, the routine performs step 308 to compute the output decrease rate Vd(t). More specifically, the output decrease rate Vd(t) is computed in step 308 by substituting the change amount ΔN(t) computed in step 306 into Equation (3) above.

Next, the routine performs step 310 to judge whether the output decrease rate Vd(t) is lower than a predetermined reference value Vth2. The reference value Vth2 is predetermined, for instance, by an experiment and used as a threshold value for forming a deterioration judgment about the oxygen pump cell 2. If the judgment result obtained in step 310 does not indicate that Vd(t)<Vth2, the routine concludes that the oxygen pump cell 2 is not deteriorated, and then comes to an immediate end.

If, on the other hand, the judgment result obtained in step 310 indicates that Vu(t)<Vth2, the routine concludes that the oxygen pump cell 2 is deteriorated, proceeds to the next step (step 312), and forms a deterioration judgment about the oxygen pump cell 2. More specifically, the routine performs a process in step 312 to illuminate the MIL indicator on the gas concentration detection apparatus for the purpose of announcing that the oxygen pump cell 2 is deteriorated.

As described above, the second embodiment forms a deterioration judgment about the oxygen pump cell 2 during a process that is performed to locate an inflection point in the NOx sensor cell output N. It means that a deterioration judgment is formed before the NOx sensor 1 becomes active. This makes it possible to effectively avoid a situation where the output of a deteriorated NOx sensor is used for various control operations.

The second embodiment, which has been described above, forms a deterioration judgment about the oxygen pump cell 2 in accordance with a comparison between the output decrease rate Vd(t) and the predetermined reference value Vth2. However, the value for forming a deterioration judgment about the oxygen pump cell 2 is not limited to the output decrease rate Vd(t). For example, the output change amount may be used for deterioration judgment as far as it correlates with the decrease rate of the NOx sensor cell output N. Another alternative value for deterioration judgment would be, for instance, the output prevailing after the elapse of a predetermined time period since the start of power application to the heater 6 or the time required for obtaining a predefined output.

Further, the second embodiment, which has been described above, forms a deterioration judgment about the oxygen pump cell 2 in accordance with a comparison between the output decrease rate Vd(t) and the predetermined reference value Vth2. However, the output decrease rate Vd(t) may be corrected to further improve the accuracy of deterioration judgment about the oxygen pump cell 2. The output decrease rate Vd(t) is affected by the concentration of oxygen remaining in the first and second internal spaces 31, 32. More specifically, the longer the soak time for the NOx sensor 1, that is, the higher the concentration of oxygen in the above-mentioned spaces, the lower the output decrease rate Vd(t). Therefore, the influence of the difference in the concentration of remaining oxygen can be corrected to improve the accuracy of deterioration judgment. The above correction may be made by correcting the output decrease rate Vd(t) or the reference value Vth2 in accordance with the concentration of remaining oxygen.

Furthermore, the second embodiment, which has been described above, forms a deterioration judgment about the oxygen pump cell 2 in accordance with a comparison between the output decrease rate Vd(t) and the predetermined reference value Vth2. Alternatively, however, a deterioration judgment about the NOx sensor cell 4 may be formed in accordance with the first embodiment while at the same time a deterioration judgment about the oxygen pump cell 2 is formed in accordance with the second embodiment. More specifically, an alternative would be to form a deterioration judgment about the NOx sensor cell 4 during an increase in the NOx sensor cell output N, which precedes the appearance of an inflection point in the NOx sensor cell output N, and form a deterioration judgment about the oxygen pump cell 2 during a decrease in the NOx sensor cell output N. This makes it possible to form an accurate deterioration judgment about the NOx sensor 1 before an inflection point appears in the NOx sensor cell output N, that is, before an activity judgment about the NOx sensor 1 is formed.

In the second embodiment, which has been described above, the NOx sensor 1 corresponds to the "gas sensor" according to the first aspect of the present invention; the oxygen pump cell 2 corresponds to the "oxygen concentration control means" according to the first aspect of the present invention; the NOx sensor cell 4 corresponds to the "gas concentration detection cell" according to the first aspect of the present invention; and the NOx sensor cell output corresponds to the "cell output" according to the first aspect of the present invention. The "deterioration judgment means" according to the first aspect of the present invention is implemented when the ECU 8 performs step 310.

Further, in the second embodiment, which has been described above, the NOx sensor 1 corresponds to the "gas sensor" according to the second aspect of the present invention; the oxygen pump cell 2 corresponds to the "excess oxygen removal means" according to the second aspect of the present invention; the NOx sensor cell 4 corresponds to the "gas concentration detection cell" according to the second aspect of the present invention; and the NOx sensor cell output corresponds to the "cell output" according to the second aspect of the present invention. The "deterioration judgment means" according to the second aspect of the present invention is implemented when the ECU 8 performs step 310.

Furthermore, in the second embodiment, which has been described above, the output decrease rate Vd(t) corresponds to the "decrease rate correlation value" according to the fifth aspect of the present invention. The "decrease rate correlation value acquisition means" according to the fifth aspect of the present invention is implemented when the ECU 8 performs step 308.

Moreover, in the second embodiment, which has been described above, the output decrease rate Vd(t) corresponds to the "decrease rate" according to the sixth aspect of the present invention. The "decrease rate acquisition means" according to the sixth aspect of the present invention is implemented when the ECU 8 performs step 308.

Third Embodiment

Feature of Third Embodiment

Figure 9:
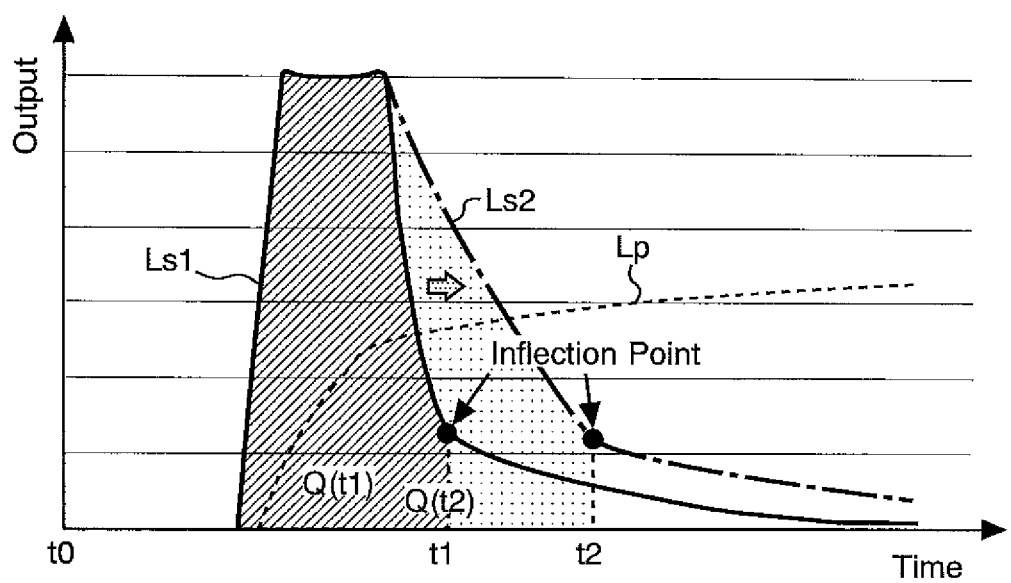
FIG. 9 is a diagram illustrating how the NOx sensor cell output N changes when the oxygen pump cell 2 deteriorates.
Figure 10:
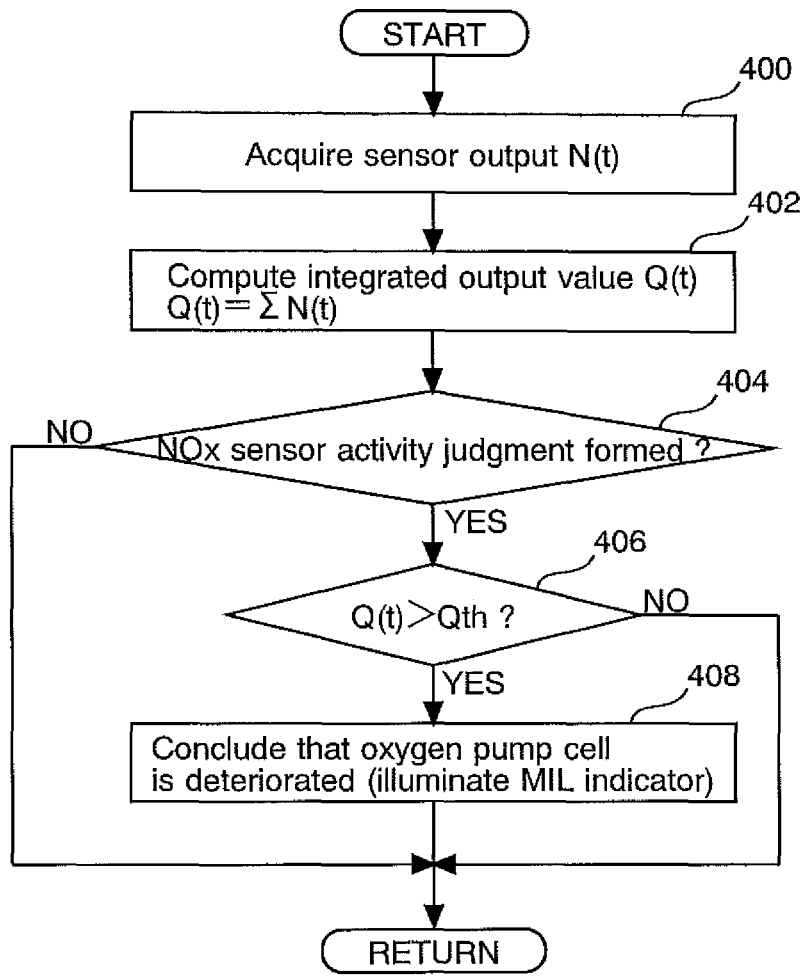
FIG. 10 is a flowchart illustrating a routine that the ECU 8 executes in accordance with a third embodiment of the present invention.

A third embodiment of the present invention will now be described with reference to FIGS. 9 and 10. A system according to the third embodiment is implemented when the hardware configuration shown in FIG. 1 is employed to let the ECU 8 execute a later-described routine shown in FIG. 10.

When the output decrease rate Vd(t) of the NOx sensor cell output N(t) is lower than the predetermined reference value Vth2 while a process is performed to locate an inflection point in the NOx sensor cell output N, the second embodiment concludes that the oxygen pump cell 2 is deteriorated.

When the oxygen pump cell 2 in the NOx sensor 1 deteriorates as described in conjunction with the second embodiment, the NOx sensor cell output N before the inflection point changes. FIG. 9 is a diagram illustrating how the NOx sensor cell output N changes when the oxygen pump cell 2 is deteriorated. In FIG. 9, a broken line Lp indicates changes in the oxygen pump cell output; a solid line Ls1 indicates output changes in the NOx sensor cell 4 that occur when the oxygen pump cell 2 is normal; and a one-dot chain line Ls2 indicates output changes in the NOx sensor cell 4 that occur when the oxygen pump cell 2 is deteriorated.

As indicated by the one-dot chain line Ls2 in the figure, when the oxygen pump cell 2 is deteriorated, the output decrease rate Vd(t) is lower than when the oxygen pump cell 2 is normal. Therefore, an integrated output value Q(t2) that is reached between time t0, at which the NOx sensor 1 begins to warm up, and time t2, at which an inflection point appears in the one-dot chain line Ls2, is greater than an integrated output value Q(t1) of a normal NOx sensor output, which is indicated by the solid line Ls1.

Consequently, the present embodiment forms a deterioration judgment about the NOx sensor 1 in accordance with the above-described output tendency. More specifically, Equation (4) below is used to compute an integrated output value Q(t) that is reached during the interval between the instant at which the NOx sensor 1 begins to warm up and the time t at which an inflection point appears. When the computed integrated output value Q(t) is greater than a predetermined reference value Qth, a deterioration judgment about the oxygen pump cell 2 in the NOx sensor 1 is formed.

$$Q(t)=\Sigma N(t) \quad (4)$$

As described above, the gas concentration detection apparatus according to the third embodiment forms a deterioration judgment about the oxygen pump cell 2 during a process for locating an inflection point that appears in the NOx sensor cell output N. This makes it possible to accurately check for deterioration of the NOx sensor 1 before it becomes active.

[Details of Process Performed by Third Embodiment]

A process performed by the third embodiment will now be described in detail with reference to FIG. 10. FIG. 8 is a flowchart illustrating a routine that the ECU 8 executes to form a deterioration judgment about the NOx sensor 1, or more specifically, a deterioration judgment about the oxygen pump cell 2, in accordance with the third embodiment. The routine starts at predetermined intervals together with the routine shown in FIG. 5. First of all, the routine shown in FIG. 10 performs step 400 to acquire the NOx sensor cell output N(t). More specifically, the process performed in step 400 is the same as the process performed in step 302.

Next, the routine performs step 402 to compute an integrated output value Q(t) of the NOx sensor cell output N. More specifically, the integrated output value reached by time t is computed by substituting the NOx sensor cell output N(t) acquired in step 400 into Equation (4) above.

Next, the routine performs step 404 to perform an activity judgment process on the NOx sensor 1. More specifically, the process performed in step 404 is the same as the process performed in step 300. If the judgment result obtained in step 404 does not indicate that an activity judgment about the NOx sensor 1 is formed, the routine concludes that the NOx sensor 1 is still not activated, and then comes to an immediate end.

If, on the other hand, the judgment result obtained in step 404 indicates that an activity judgment about the NOx sensor 1 is formed, the routine concludes that the integrated output value Q(t) computed in step 402 represents an integrated output value that is reached by the time an inflection point appears, proceeds to the next step (step 406), and judges whether the integrated output value Q(t) is greater than the reference value Qth. The reference value Qth is predetermined, for instance, by an experiment and used as a threshold value for forming a deterioration judgment about the oxygen pump cell 2. If the judgment result obtained in step 406 does not indicate that Q(t)>Qth, the routine concludes that the oxygen pump cell 2 is not deteriorated, and then comes to an immediate end.

If, on the other hand, the judgment result obtained in step 406 indicates that Q(t)>Qth, the routine concludes that the oxygen pump cell 2 is deteriorated, proceeds to the next step (step 408), and forms a deterioration judgment to indicate that the oxygen pump cell 2 is deteriorated. More specifically, the routine performs the same process as in step 312 to illuminate the MIL indicator on the gas concentration detection apparatus for the purpose of announcing that the oxygen pump cell 2 is deteriorated.

As described above, the third embodiment forms a deterioration judgment about the oxygen pump cell 2 during a process for locating an inflection point in the NOx sensor cell output N. Therefore, a deterioration judgment can be formed before the NOx sensor 1 becomes active. This makes it possible to effectively avoid a situation where the output of a deteriorated NOx sensor is used for various control operations.

The third embodiment, which has been described above, forms a deterioration judgment about the oxygen pump cell 2 in accordance with a comparison between the integrated output value Q(t) and the predetermined reference value Qth. Alternatively, however, the integrated output value Q(t) may be corrected to further improve the accuracy of deterioration judgment about the oxygen pump cell 2. The integrated output value Q(t) is affected by the concentration of oxygen remaining in the first and second internal spaces 31, 32. More specifically, the longer the soak time for the NOx sensor 1, that is, the higher the concentration of oxygen in the above-mentioned spaces, the greater the integrated output value Q(t). Therefore, the influence of the difference in the concentration of remaining oxygen can be corrected to improve the accuracy of deterioration judgment. The above correction may be made by correcting the integrated output value Q(t) or the reference value Qth in accordance with the concentration of remaining oxygen.

Further, the third embodiment, which has been described above, forms a deterioration judgment about the oxygen pump cell 2 in accordance with a comparison between the integrated output value Q(t) and the predetermined reference value Qth. Alternatively, however, a deterioration judgment about the NOx sensor cell 4 may be formed in accordance with the first embodiment while at the same time a deterioration judgment about the oxygen pump cell 2 is formed in accordance with the third embodiment. More specifically, an alternative would be to form a deterioration judgment about the NOx sensor cell 4 during an increase in the NOx sensor cell output N, which precedes the appearance of an inflection point in the NOx sensor cell output N, and form a deterioration judgment about the oxygen pump cell 2 in accordance with the integrated output value Q(t) that is reached by the time at which an inflection point appears in the NOx sensor cell output N. This makes it possible to form an accurate deterioration judgment about the NOx sensor 1 before an inflection point appears in the NOx sensor cell output N, that is, before an activity judgment about the NOx sensor 1 is formed.

In the third embodiment, which has been described above, the NOx sensor 1 corresponds to the "gas sensor" according to the first aspect of the present invention; the oxygen pump cell 2 corresponds to the "oxygen concentration control means" according to the first aspect of the present invention; the NOx sensor cell 4 corresponds to the "gas concentration detection cell" according to the first aspect of the present invention; and the NOx sensor cell output corresponds to the "cell output" according to the first aspect of the present invention. The "deterioration judgment means" according to the first aspect of the present invention is implemented when the ECU 8 performs step 410.

Further, in the third embodiment, which has been described above, the NOx sensor 1 corresponds to the "gas sensor" according to the second aspect of the present invention; the oxygen pump cell 2 corresponds to the "excess oxygen removal means" according to the second aspect of the present invention; the NOx sensor cell 4 corresponds to the "gas concentration detection cell" according to the second aspect of the present invention; and the NOx sensor cell output corresponds to the "cell output" according to the second aspect of the present invention. The "deterioration judgment means" according to the second aspect of the present invention is implemented when the ECU 8 performs step 410.

Furthermore, in the third embodiment, which has been described above, the integrated output value Q(t) corresponds to the "decrease rate correlation value" according to the fifth aspect of the present invention. The "decrease rate correlation value acquisition means" according to the fifth aspect of the present invention is implemented when the ECU 8 performs step 402.

Moreover, in the third embodiment, which has been described above, the integrated output value Q(t) corresponds to the "integrated value" according to the seventh aspect of the present invention. The "integrated value acquisition means" according to the seventh aspect of the present invention is implemented when the ECU 8 performs step 402.

Fourth Embodiment

Features of Fourth Embodiment

Figure 11:
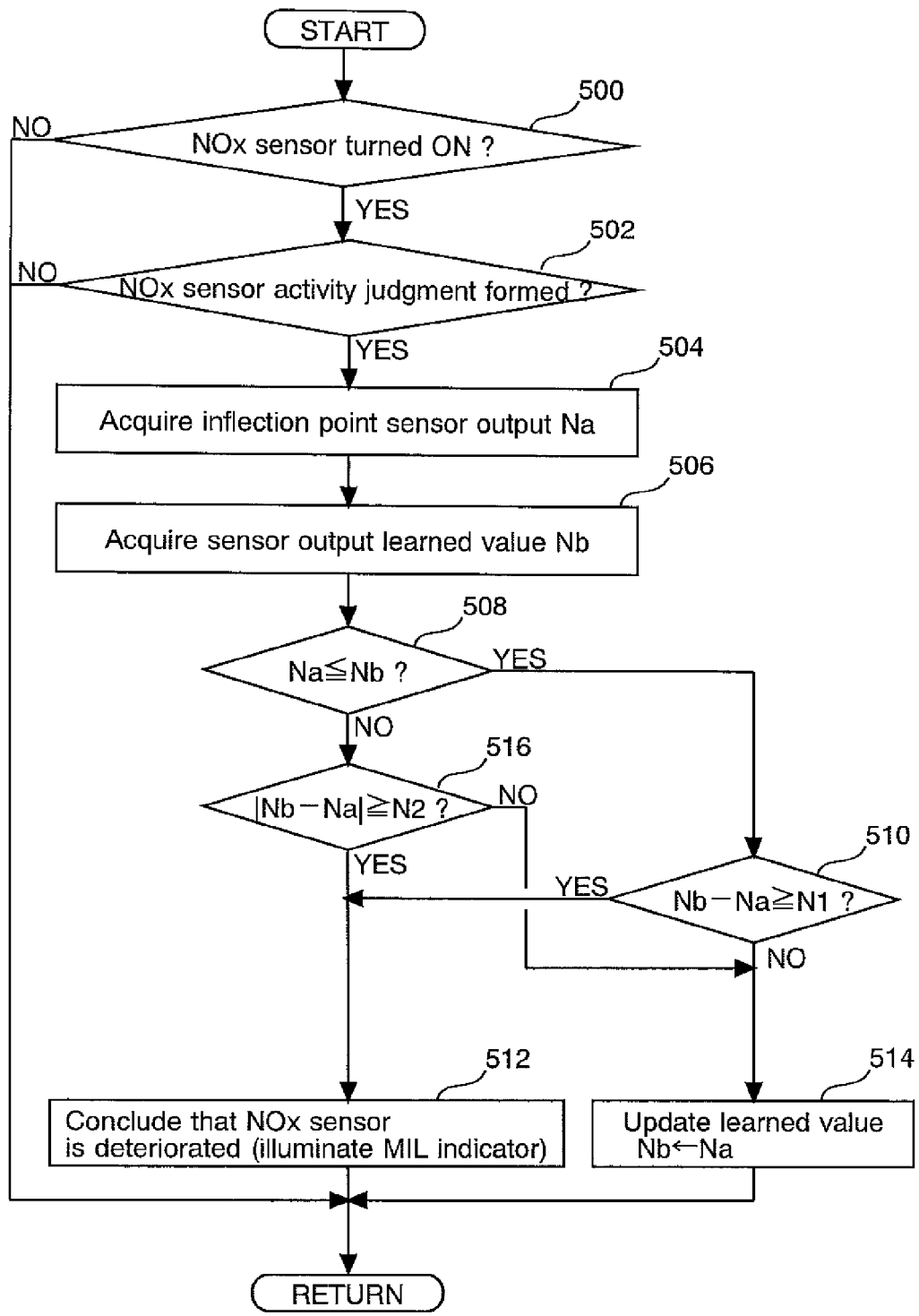
FIG. 11 is a flowchart illustrating a routine that the ECU 8 executes in accordance with a fourth embodiment of the present invention.

A fourth embodiment of the present invention will now be described with reference to FIG. 11. A system according to the fourth embodiment is implemented when the hardware configuration shown in FIG. 1 is employed to let the ECU 8 execute a later-described routine shown in FIG. 11.

The first to third embodiments, which have been described earlier, form a deterioration judgment about the NOx sensor 1 during a process for locating an inflection point in the NOx sensor cell output N. However, an error due, for instance, to individual sensor differences is superimposed on the NOx sensor cell output N. Therefore, when the employed configuration compares, for instance, the rate of increase or decrease in the NOx sensor cell output N before inflection point appearance against a predetermined reference value, it is probable that an inaccurate deterioration judgment may be formed about the NOx sensor 1 because of failure to correct an output error based on individual sensor differences.

In view of the above circumstances, the fourth embodiment forms a deterioration judgment about the NOx sensor 1 in consideration of the influence, for instance, of individual sensor differences by learning and using information about an inflection point. More specifically, the NOx decomposition capability decreases when the NOx sensor 1 deteriorates. Therefore, the NOx sensor cell output N of a deteriorated NOx sensor 1 is lower than when the NOx sensor 1 is normal. As such being the case, the fourth embodiment stores the last value of the NOx sensor cell output prevailing at an inflection point of the NOx sensor 1 as a learned value (hereinafter referred to as the "inflection point output learned value"). When the NOx sensor cell output prevailing at an inflection point (hereinafter referred to as the "inflection point output") is considerably smaller than the inflection point output learned value, the fourth embodiment judges that the NOx sensor 1 is deteriorated. This makes it possible to form an accurate deterioration judgment about the NOx sensor 1.

In a normal NOx sensor 1, the inflection point output is unlikely to be considerably greater than the inflection point output learned value. In such a case, too, it is possible to judge that the NOx sensor 1 is more or less deteriorated. When a deterioration judgment about the NOx sensor 1 is formed in accordance with a comparison between the inflection point output and the inflection point output learned value as described above, it is possible to form a deterioration judgment in consideration of the influence of individual sensor differences that is superimposed on the NOx sensor cell output. Further, as a deterioration judgment can be formed when the NOx sensor 1 becomes active, it is possible to effectively avoid a situation where the output of a deteriorated NOx sensor is used for various control operations.

[Details of Process Performed by Fourth Embodiment]

A process performed by the fourth embodiment will now be described in detail with reference to FIG. 11. FIG. 11 is a flowchart illustrating a routine that the ECU 8 executes to form a deterioration judgment about the NOx sensor 1 and update a learned value in accordance with the fourth embodiment. The routine starts at predetermined intervals together with the routine shown in FIG. 5. First of all, the routine shown in FIG. 11 performs step 500 to judge whether the NOx sensor 1 is energized. If the obtained judgment result does not indicate that the NOx sensor 1 is energized, the routine comes to an immediate end.

If, on the other hand, the judgment result obtained in step 500 indicates that the NOx sensor 1 is energized, the routine proceeds to the next step (step 502) and forms an activity judgment about the NOx sensor 1. More specifically, the process performed in step 502 is the same as the process performed in step 404. If the judgment result obtained in step 502 indicates that an inflection point has not appeared in the NOx sensor cell output of the NOx sensor 1, the routine concludes that the NOx sensor 1 is still not activated, and comes to an immediate end.

If, on the other hand, the judgment result obtained in step 502 indicates that the NOx sensor 1 is activated, the routine proceeds to the next step (step 504) and acquires the NOx sensor cell output at an inflection point (inflection point output) Na. The routine then performs step 506 to acquire a learned value of the NOx sensor cell output at the inflection point (inflection point output learned value) Nb. More specifically, the inflection point output learned value Nb updated in step 514, which will be described later, is acquired.

Next, the routine performs step 508 to compare the inflection point output Na against the inflection point output learned value Nb. More specifically, step 508 is performed to judge whether the inflection point output Na acquired in step 504 is not greater than the inflection point output learned value Nb acquired in step 506. If the obtained judgment result indicates that the inflection point output Na is not greater than the inflection point output learned value Nb, the routine concludes that the inflection point output Na tends to decrease, proceeds to the next step, and judges whether the deviation (Nb−Na) between the inflection point output learned value Nb and the inflection point output Na is not smaller than a predetermined value N1. The value N1 is predetermined, for instance, by an experiment and used as a threshold value for forming a deterioration judgment about the NOx sensor 1. If the obtained judgment result indicates that Nb−Na≧N1, the routine concludes that the amount of decrease in the inflection point output Na is not smaller than the predetermined value N1, proceeds to the next step (step 512), and concludes that the NOx sensor 1 is deteriorated. More specifically, step 512 is performed in the same manner as in step 410 to illuminate the MIL indicator on the gas concentration detection apparatus for the purpose of announcing that the NOx sensor 1 is deteriorated.

If, on the other hand, the judgment result obtained in step 510 does not indicate that Nb−Na≧N1, the routine concludes that the amount of decrease in the inflection point output Na is smaller than the predetermined value N1, that is, the NOx sensor 1 is not deteriorated, proceeds to the next step (step 514), and update the learned value. More specifically, the inflection point output Na acquired in step 504 is updated as a new inflection point output learned value Nb.

If the judgment result obtained in step 508 does not indicate that the inflection point output Na is equal to or smaller than the inflection point output learned value Nb (Na≦Nb), the routine concludes that the inflection point output Na tends to increase, proceeds to the next step (step 516), and judges whether the absolute value |Nb−Na| of the deviation between the inflection point output learned value Nb and the inflection point output Na is not smaller than a predetermined value N2.

The value N2 is predetermined, for instance, by an experiment and used as a threshold value for forming a deterioration judgment about the NOx sensor 1. If the obtained judgment result indicates that |Nb−Na|≧N2, the routine finds that the amount of increase in the inflection point output Na is not smaller than the predetermined value N2, proceeds to step 512, and concludes that the NOx sensor 1 is deteriorated.

If, on the other hand, the judgment result obtained in step 516 does not indicate that |Nb−Na|≧N2, the routine concludes that the amount of increase in the inflection point output Na is smaller than the predetermined value N2, that is, the NOx sensor 1 is not deteriorated, proceeds to step 514, and updates the learned value.

As described above, the fourth embodiment forms a deterioration judgment about the NOx sensor 1 in accordance with a comparison between the inflection point output Na and the inflection point output learned value Nb. Therefore, a deterioration judgment can be formed in consideration of the influence of individual sensor differences that is superimposed on the NOx sensor cell output. This makes it possible to effectively improve the accuracy of judgment. Further, as the fourth embodiment can form a deterioration judgment when the NOx sensor 1 becomes active, it is possible to effectively avoid a situation where the output of a deteriorated NOx sensor is used for various control operations.

The fourth embodiment, which has been described above, forms a deterioration judgment about the NOx sensor 1 in accordance with a comparison between the inflection point output Na and the inflection point output learned value Nb. Alternatively, however, a deterioration judgment about the NOx sensor 1 may be formed in accordance with the first to third embodiments while at the same time the deterioration judgment is formed in accordance with the fourth embodiment. More specifically, an alternative would be to form a deterioration judgment about the NOx sensor cell 4 during an increase in the NOx sensor cell output N, which precedes the execution of the process according to the present embodiment, that is, the appearance of an inflection point in the NOx sensor cell output N, form a deterioration judgment about the oxygen pump cell 2 during a decrease in the NOx sensor cell output N, and form a deterioration judgment about the oxygen pump cell 2 in accordance with the integrated output value Q(t) that is reached by the time the inflection point appears in the NOx sensor cell output N.

Further, the fourth embodiment, which has been described above, uses the inflection point output learned value Nb as a learned value concerning the information about an inflection point. However, the available learned value is not limited to the inflection point output learned value Nb. For example, the time required for inflection point location and an element temperature correlation value (impedance, heater resistance, or heater power) at the inflection point may alternatively be used as the learned value as far as it correlates with the NOx sensor cell output at the inflection point.

In the fourth embodiment, which has been described above, the NOx sensor 1 corresponds to the "gas sensor" according to the first aspect of the present invention; the oxygen pump cell 2 corresponds to the "oxygen concentration control means" according to the first aspect of the present invention; the NOx sensor cell 4 corresponds to the "gas concentration detection cell" according to the first aspect of the present invention; and the NOx sensor cell output corresponds to the "cell output" according to the first aspect of the present invention. The "deterioration judgment means" according to the first aspect of the present invention is implemented when the ECU 8 performs step 512.

In the fourth embodiment, which has been described above, the NOx sensor 1 corresponds to the "gas sensor" according to the second aspect of the present invention; the oxygen pump cell 2 corresponds to the "excess oxygen removal means" according to the second aspect of the present invention; the NOx sensor cell 4 corresponds to the "gas concentration detection cell" according to the second aspect of the present invention; and the NOx sensor cell output corresponds to the "cell output" according to the second aspect of the present invention. The "deterioration judgment means" according to the second aspect of the present invention is implemented when the ECU 8 performs step 512.

Further, in the fourth embodiment, which has been described above, the inflection point output learned value Nb corresponds to the "learned value" according to the eighth aspect of the present invention; and the inflection point output Na corresponds to the "inflection point cell output" according to the eighth aspect of the present invention. The "storage means" according to the eighth aspect of the present invention is implemented when the ECU 8 performs step 514; and the "inflection point cell output acquisition means" according to the eighth aspect of the present invention is implemented when the ECU 8 performs step 504.

Furthermore, in the fourth embodiment, which has been described above, the predetermined value N1 corresponds to the "predetermined reference value" according to the ninth aspect of the present invention; the predetermined value N2 corresponds to the "predetermined reference value" according to the tenth aspect of the present invention; and the predetermined value N1 corresponds to the "predetermined reference value" according to the fourteenth aspect of the present invention.

Fifth Embodiment

Features of the Fifth Embodiment

Figure 12:
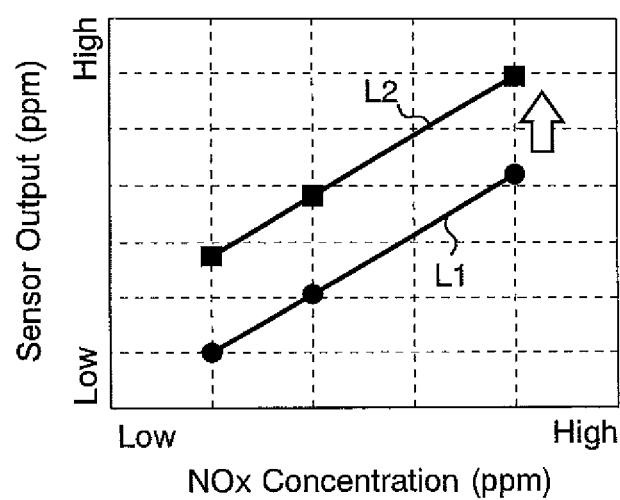
FIG. 12 is a diagram illustrating NOx sensor cell output changes with respect to NOx concentration.
Figure 13:
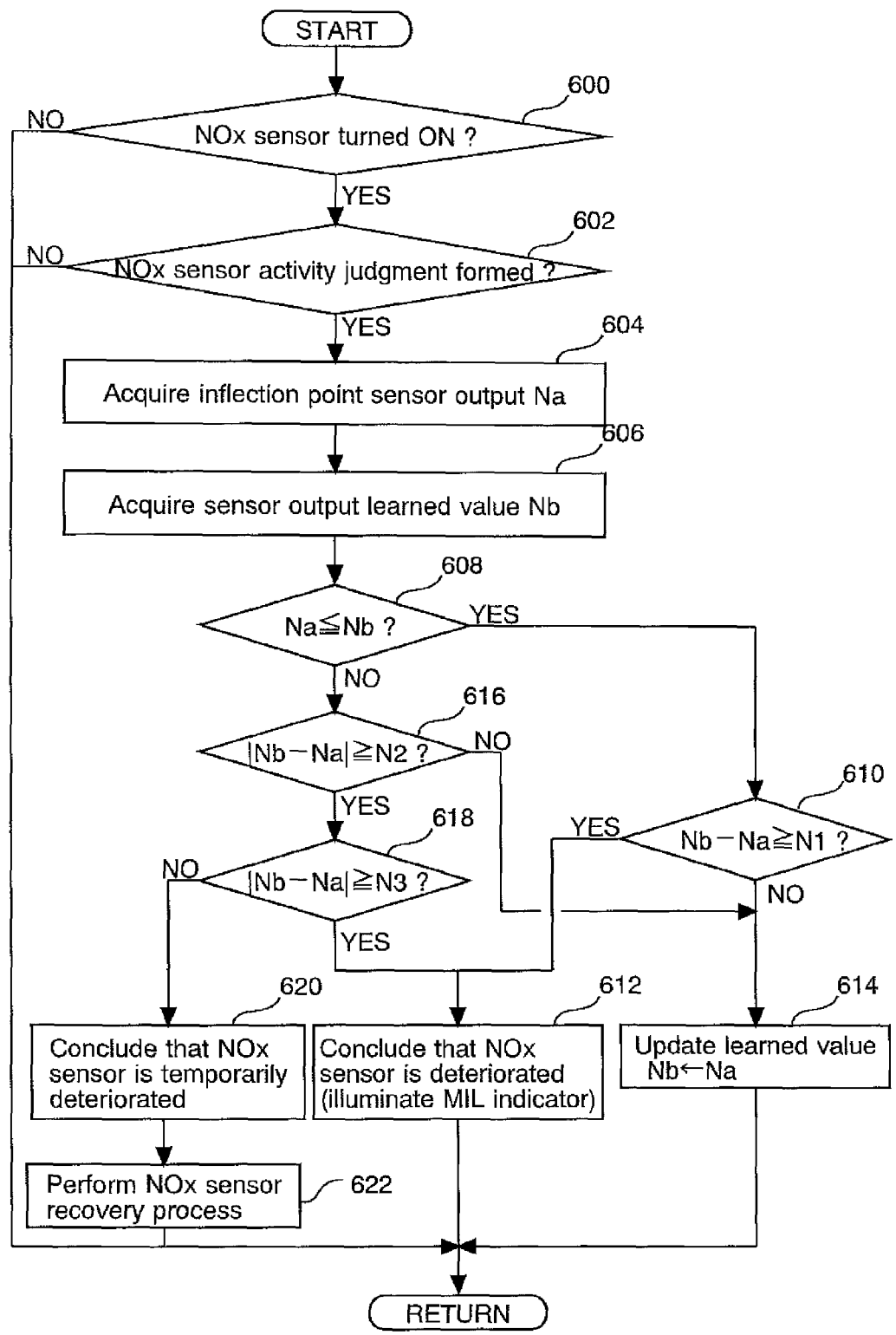
FIG. 13 is a flowchart illustrating a routine that the ECU 8 executes in accordance with a fifth embodiment of the present invention.

A fifth embodiment of the present invention will now be described with reference to FIGS. 12 and 13. A system according to the fifth embodiment is implemented when the hardware configuration shown in FIG. 1 is employed to let the ECU 8 execute a later-described routine shown in FIG. 13.

The fourth embodiment, which has been described earlier, forms a deterioration judgment about the NOx sensor 1 in accordance with a comparison between the inflection point output Na and the inflection point output learned value Nb. Therefore, the fourth embodiment can form a deterioration judgment in consideration of the influence of individual sensor differences that is superimposed on the NOx sensor cell output.

NOx sensor deterioration is either unrecoverable permanent deterioration or recoverable temporary deterioration. When the NOx sensor 1 is exposed to a lean atmosphere while its sensor element is maintained at a low temperature, the first detection electrode 42 in the NOx sensor cell 4 oxidizes. Therefore, when, for instance, heater energization delay control is exercised in consideration of the sensor element's water soak resistance failure, it is probable that electrode oxidation may progress. Recovery from deterioration caused by electrode oxidation can be achieved by performing a recovery process to promote reduction reaction in the electrode as far as the degree of oxidation is not significantly high. In view of the above circumstances, the fifth embodiment classifies NOx sensor deterioration into permanent deterioration and temporary deterioration and performs the recovery process when temporary deterioration is encountered. This makes it possible to reuse a temporarily deteriorated NOx sensor 1 by restoring it to normal.

The NOx sensor cell output N is used to judge whether the NOx sensor 1 is temporarily deteriorated or permanently deteriorated. FIG. 12 is a diagram illustrating NOx sensor cell output changes with respect to NOx concentration. In FIG. 12, line L1 indicates NOx sensor cell output changes in a normal NOx sensor, whereas line L2 indicates NOx sensor cell output changes in a NOx sensor that is deteriorated due to electrode oxidation.

As shown in the figure, the NOx sensor whose electrode is oxidized generates a greater NOx sensor cell output than the normal NOx sensor. The reason is that reduction reaction progresses at the oxidized electrode to let the NOx sensor cell generate an output. Further, the NOx sensor cell output N increases with an increase in the degree of electrode oxidation of the NOx sensor 1. Consequently, when the deviation (Nb−Na) between the inflection point output learned value Nb and the inflection point output Na is smaller than a predetermined value N3, the fifth embodiment concludes that recovery can be made from deterioration caused by oxidation of the NOx sensor 1, and then performs a recovery process.

More specifically, the recovery process is performed to promote reduction reaction at the first detection electrode 42 of the NOx sensor cell 4. The reduction reaction at the first detection electrode 42 can be promoted, for instance, by performing a process for temporarily increasing the amount of drive of the oxygen pump cell 2 to lower the concentration of oxygen near the first detection electrode 42, a process for applying a voltage to the NOx sensor cell 4, or a process for driving the heater 6 to temporarily raise the element temperature. As a result, effective recovery can be made from temporary deterioration of the NOx sensor 1.

[Details of Process Performed by Fifth Embodiment]

A process performed by the fifth embodiment will now be described in detail with reference to FIG. 13. FIG. 13 is a flowchart illustrating a routine that the ECU 8 executes to form a deterioration judgment about the NOx sensor 1 and execute a recovery process in accordance with the fifth embodiment. The routine starts at predetermined intervals together with the routine shown in FIG. 5. First of all, steps 600 to 616 of the routine shown in FIG. 13 are performed in the same manner as steps 500 to 516, which have been described earlier.

If the judgment result obtained in step 616 indicates that |Nb−Na|≧N2, the routine concludes that the amount of increase in the inflection point output Na is not smaller than the predetermined value N2, that is, the NOx sensor 1 is deteriorated, proceeds to the next step (step 618), and judges whether the absolute value |Nb−Na| of the deviation between the inflection point output learned value Nb and the inflection point output Na is not smaller than the predetermined value N3. The value N3 is predetermined, for instance, by an experiment and used as a threshold value for forming a temporary deterioration judgment about the NOx sensor 1. If the obtained judgment result indicates that |Nb−Na−≧N3, the routine finds that the amount of increase in the inflection point output Na is not smaller than the predetermined value N3, that is, unrecoverable permanent deterioration, which cannot be fully restored to normal, is encountered, proceeds to step 612, and concludes that the NOx sensor 1 is deteriorated.

If, on the other hand, the judgment result obtained in step 618 does not indicate that |Nb−Na|≧N3, the routine concludes that the amount of increase in the inflection point output Na is smaller than the predetermined value N3, that is, the degree of deterioration caused by electrode oxidation is such that recovery can be made, proceeds to the next step (step 620), and concludes that the NOx sensor 1 is temporarily deteriorated. Next, the routine proceeds to step 622 and performs a recovery process on the NOx sensor 1. More specifically, the routine performs a process in step 622 to promote reduction reaction at the first detection electrode 42 of the NOx sensor cell 4.

As described above, the fifth embodiment compares the inflection point output Na against the inflection point output learned value Nb to judge whether the NOx sensor 1 is temporarily deteriorated or permanently deteriorated. Therefore, when the NOx sensor 1 is temporarily deteriorated, the fifth embodiment can perform a recovery process to recover the original performance of the NOx sensor 1.

The fifth embodiment, which has been described above, forms a deterioration judgment about the NOx sensor 1 and performs a recovery process in accordance with a comparison between the inflection point output Na and the inflection point output learned value Nb. Alternatively, however, a deterioration judgment about the NOx sensor 1 may be formed in accordance with the first to third embodiments while at the same time the deterioration judgment and recovery process are performed in accordance with the fifth embodiment. More specifically, an alternative would be to form a deterioration judgment about the NOx sensor cell 4 during an increase in the NOx sensor cell output N, which precedes the execution of the process according to the present embodiment, that is, the appearance of an inflection point in the NOx sensor cell output N, form a deterioration judgment about the oxygen pump cell 2 during a decrease in the NOx sensor cell output N, and form a deterioration judgment about the oxygen pump cell 2 in accordance with the integrated output value Q(t) that is reached by the time the inflection point appears in the NOx sensor cell output N.

In the fifth embodiment, which has been described above, the NOx sensor 1 corresponds to the "gas sensor" according to the first aspect of the present invention; the oxygen pump cell 2 corresponds to the "oxygen concentration control means" according to the first aspect of the present invention; the NOx sensor cell 4 corresponds to the "gas concentration detection cell" according to the first aspect of the present invention; and the NOx sensor cell output corresponds to the "cell output" according to the first aspect of the present invention. The "deterioration judgment means" according to the first aspect of the present invention is implemented when the ECU 8 performs step 512.

Further, in the fifth embodiment, which has been described above, the NOx sensor 1 corresponds to the "gas sensor" according to the second aspect of the present invention; the oxygen pump cell 2 corresponds to the "excess oxygen removal means" according to the second aspect of the present invention; the NOx sensor cell 4 corresponds to the "gas concentration detection cell" according to the second aspect of the present invention; and the NOx sensor cell output corresponds to the "cell output" according to the second aspect of the present invention. The "deterioration judgment means" according to the second aspect of the present invention is implemented when the ECU 8 performs step 512.

Furthermore, in the fifth embodiment, which has been described above, the inflection point output learned value Nb corresponds to the "learned value" according to the eighth aspect of the present invention; and the inflection point output Na corresponds to the "inflection point cell output" according to the eighth aspect of the present invention. The "storage means" according to the eighth aspect of the present invention is implemented when the ECU 8 performs step 614; and the "inflection point cell output acquisition means" according to the eighth aspect of the present invention is implemented when the ECU 8 performs step 604.

Moreover, in the fifth embodiment, which has been described above, the predetermined value N1 corresponds to the "predetermined reference value" according to the ninth aspect of the present invention; the predetermined value N2 corresponds to the "predetermined reference value" according to the tenth aspect of the present invention; and the predetermined value N1 corresponds to the "predetermined reference value" according to the fourteenth aspect of the present invention.

In addition, in the fifth embodiment, which has been described above, the "temporary deterioration judgment means" according to the eleventh aspect of the present invention is implemented when the ECU 8 performs step 620.

Besides, in the fifth embodiment, which has been described above, the predetermined value N3 corresponds to the "predetermined reference value" according to the twelfth aspect of the present invention.

Yet, in the fifth embodiment, which has been described above, the "deterioration recovery process execution means" according to the thirteenth aspect of the present invention is implemented when the ECU 8 performs step 622.

Sixth Embodiment

Description of System Configuration

Figure 14:
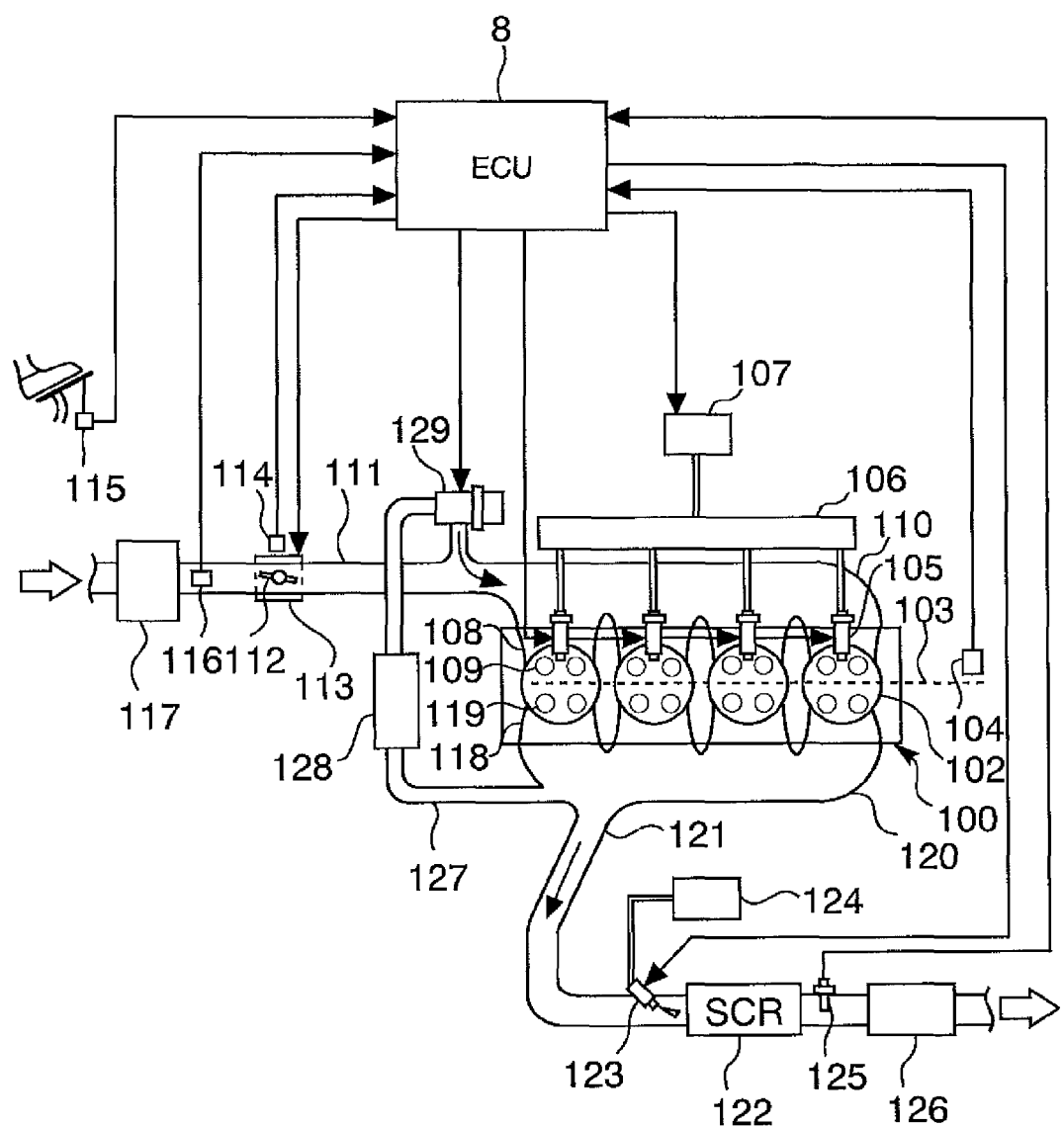
FIG. 14 is a diagram showing a typical system configuration according to a sixth embodiment of the present invention.

FIG. 14 shows a typical system configuration according to a sixth embodiment of the present invention. A system shown in FIG. 14 includes a four-cycle diesel engine (compression-ignition internal combustion engine), which is hereinafter briefly referred to as the engine 100. Alternatively, a gasoline engine (spark-ignition internal combustion engine) may be used as the engine 100. A piston of each cylinder 102 in the engine 100 is coupled to a crankshaft 103 through a crank mechanism. A crank angle sensor 104 is installed near the crankshaft 103 to detect a crank angle CA.

Each cylinder 102 in the engine 100 is provided with an injector 105 that directly injects fuel into a cylinder. Each injector 105 is connected to a shared common rail 106. The common rail 106 stores fuel that is pressurized by a supply pump 107. Each injector 105 can inject fuel into a cylinder multiple times per cycle at arbitrary timing.

An intake port 108 of the engine 100 is provided with an intake valve 109. The valve opening characteristics (valve opening timing, lift amount, and operating angle) of the intake valve 109 can be changed by a publicly known, hydraulic or mechanical variable valve train (not shown). The intake port 108 is connected to an intake path 111 through an intake manifold 110. A throttle valve 112 is installed in the middle of the intake path 111. The throttle valve 112 is an electronically controlled valve that is driven by a throttle motor 113. The throttle valve 112 is driven in accordance, for instance, with an accelerator opening AA that is detected by an accelerator opening sensor 115. A throttle opening sensor 113 is installed near the throttle valve 112 to detect a throttle opening TA. An air flow meter 116 is installed upstream of the throttle valve 112 to detect an intake air amount Ga. An air cleaner 117 is installed upstream of the air flow meter 116.

An exhaust port 118 of the engine 1 is provided with an exhaust valve 119. The valve opening characteristics (valve opening timing, lift amount, and operating angle) of the exhaust valve 119 can be changed by a publicly known, hydraulic or mechanical variable valve train (not shown). The exhaust port 118 is connected to an exhaust path 121 through an exhaust manifold 120. A selective reduction catalyst (hereinafter referred to as the "SCR (Selective Catalytic Reduction) catalyst") 122 is installed in the exhaust path 121. A urea water addition valve 123 is installed upstream of the SCR catalyst 122 to add urea water $((NH_2)_2CO+H_2O)$, which is stored in a urea water tank 124. NOx is reduced to nitrogen by ammonia that is generated from the urea water added from the urea water addition valve 123. The NOx sensor 1, which detects the concentration of NOx, is installed downstream of the SCR catalyst 122. The NOx sensor 1 will not be described in detail because it has the same configuration as the NOx sensor 1 shown in FIG. 1. An oxidation catalyst 126 is installed downstream of the NOx sensor 1 to oxidize ammonia.

The exhaust manifold 120 is connected to one end of an external EGR path 127. The other end of the external EGR path 127 is connected to the intake path 111 near the intake manifold 110. External EGR (Exhaust Gas Recirculation) can be performed by causing a portion of exhaust gas (burnt gas) to flow back to the intake path 111 through the external EGR path 127. An EGR cooler 128 is installed in the middle of the external EGR path 127 to cool external EGR gas. An EGR valve 129 is installed in the external EGR path 127 and positioned downstream of the EGR cooler 128. Increasing the opening of the EGR valve 129 increases the amount of exhaust gas that passes through the external EGR path 127 (namely, the external EGR amount or external EGR rate).

The system shown in FIG. 14 also includes an ECU (Electronic Control Unit) 8, which serves as a control device. The output end of the ECU 8 is connected, for instance, to the injector 105, supply pump 107, throttle motor 113, urea water addition valve 123, and EGR valve 129. The input end of the ECU 8 is connected to the crank angle sensor 104, throttle opening sensor 114, accelerator opening sensor 115, air flow meter 116, and NOx sensor 1. The ECU 8 includes pump cell control means 81, sensor cell control means 82, and heater control means 83. These control means are not shown in the figure because they have the same configuration as the counterparts in the gas concentration detection apparatus 10 shown in FIG. 1.

The ECU 8 calculates an engine speed NE in accordance with the crank angle CA. The ECU 8 calculates an engine load KL in accordance, for instance, with the throttle opening TA and accelerator opening AA. The ECU 8 calculates the amount of fuel injection from the injector 105 in accordance with the engine load KL. The ECU 8 also controls the operating status of the engine 100 by operating various actuators in accordance with signals from various sensors and with a predetermined program.

Features of Sixth Embodiment

If an activity judgment is formed in accordance with element impedance as described in Patent Document 6, the activity judgment time may vary with the operating status of the engine. Consequently, the sixth embodiment learns information about an inflection point at the time of inflection point location. Such learning is performed, for instance, by integrating into a map (storing in a map) the time required for inflection point location, the NOx sensor cell output prevailing when an inflection point is located, and a physical property value correlated to the element temperature prevailing at the time of inflection point location. The physical property value correlated to the element temperature can be, for instance, impedance, heater resistance, or heater power.

To learn the information about an inflection point, it is necessary to generate an inflection point in the NOx sensor cell output. For such inflection point generation, the concentration of oxygen in the NOx sensor 1 needs to be higher than a predetermined value. More specifically, the concentration of oxygen remaining in the first and second internal spaces 31, 32 needs to be increased to increase the concentration of oxygen to be absorbed by the first detection electrode 42 of the NOx sensor cell 4.

Figure 15:
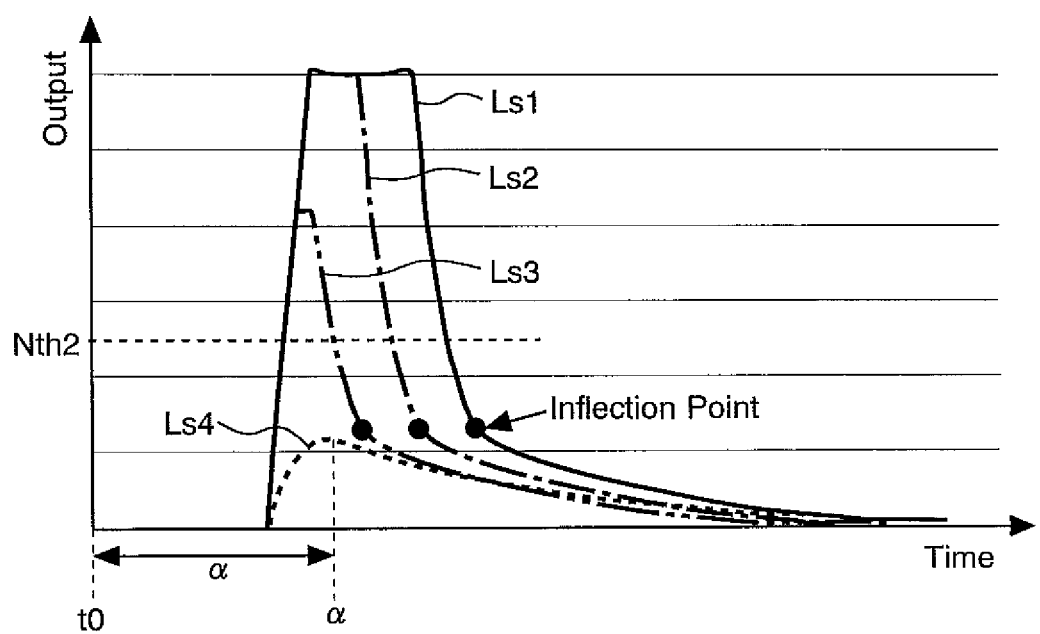
FIG. 15 is a diagram illustrating NOx sensor cell output changes with time at engine start.

When the engine starts, a certain amount of elapsed time is required between last power OFF and ignition ON (hereinafter briefly referred to as the "elapsed time"). FIG. 15 is a diagram illustrating NOx sensor cell output changes with the elapsed time at engine start. In FIG. 15, a solid line Ls1 indicates NOx sensor cell output changes in a situation where the elapsed time is sufficiently long (e.g., several hours or longer). When the elapsed time is decreased, the NOx sensor cell output is maintained at an upper limit value for a short period of time as indicated by a one-dot chain line Ls2. When the elapsed time is further decreased, the NOx sensor cell output begins to decrease before it reaches the upper limit value as indicated by a two-dot chain line Ls3. In all the above cases, the NOx sensor cell output increases above the reference value Nth2; therefore, it is possible to locate an inflection point and learn the information about the inflection point.

If, on the other hand, the elapsed time is extremely short (e.g., not longer than one hour), the NOx sensor cell output does not reach the reference value Nth2 as indicated by a broken line Ls4 even when a predetermined period of time α elapses after ignition ON. In this instance, the information about an inflection point cannot be learned because no inflection point can be located.

To learn the information about an inflection point, therefore, a certain amount of elapsed time is required to let the NOx sensor cell output increase above the reference value Nth2. In other words, it is necessary to increase the concentration of oxygen in the NOx sensor 1 to the extent that the NOx sensor cell output increases above the reference value Nth2.

[Details of Process Performed by Sixth Embodiment]

Figure 16:
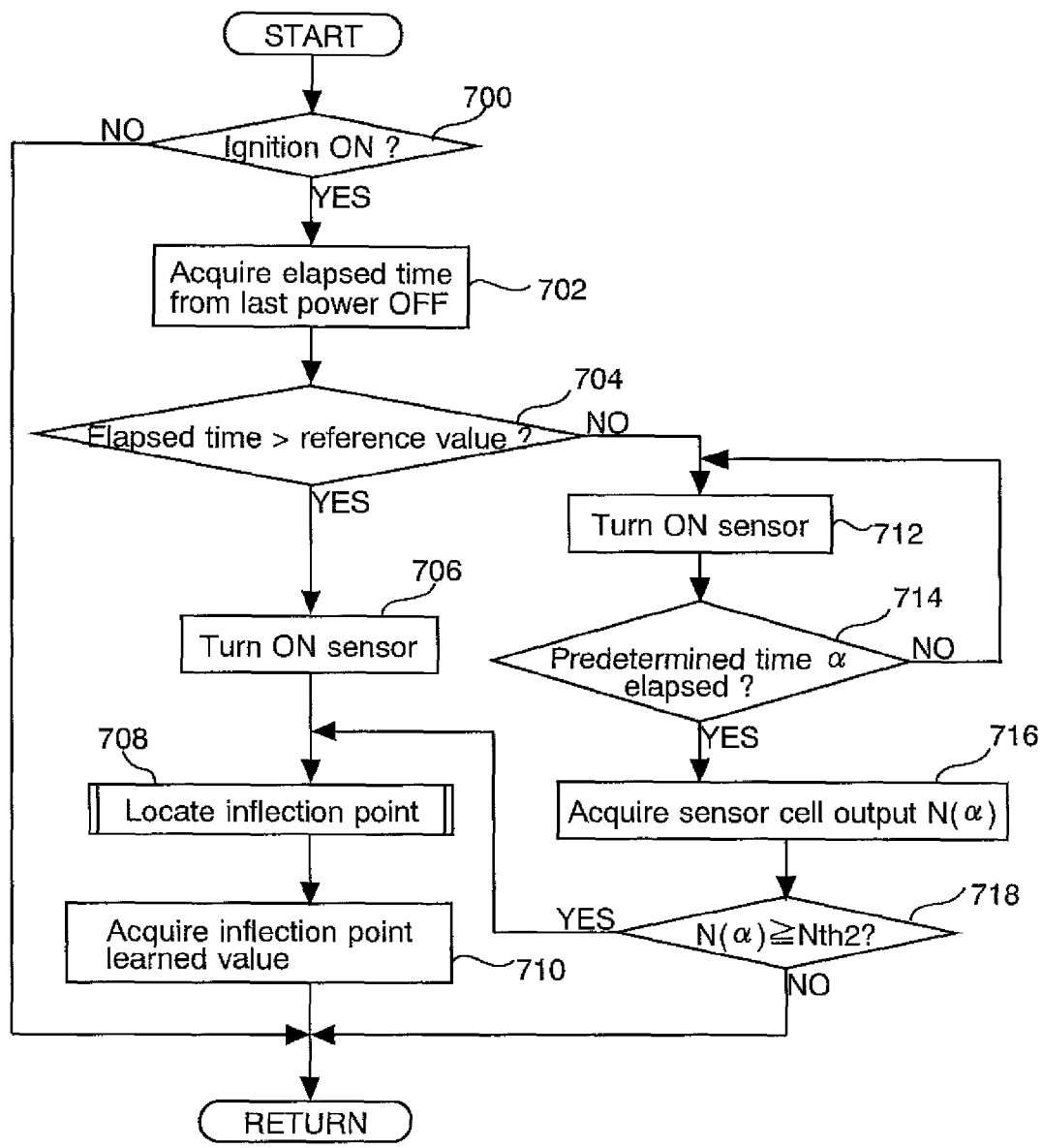
FIG. 16 is a flowchart illustrating a routine that the ECU 8 executes in accordance with a sixth embodiment of the present invention.
Figure 17:
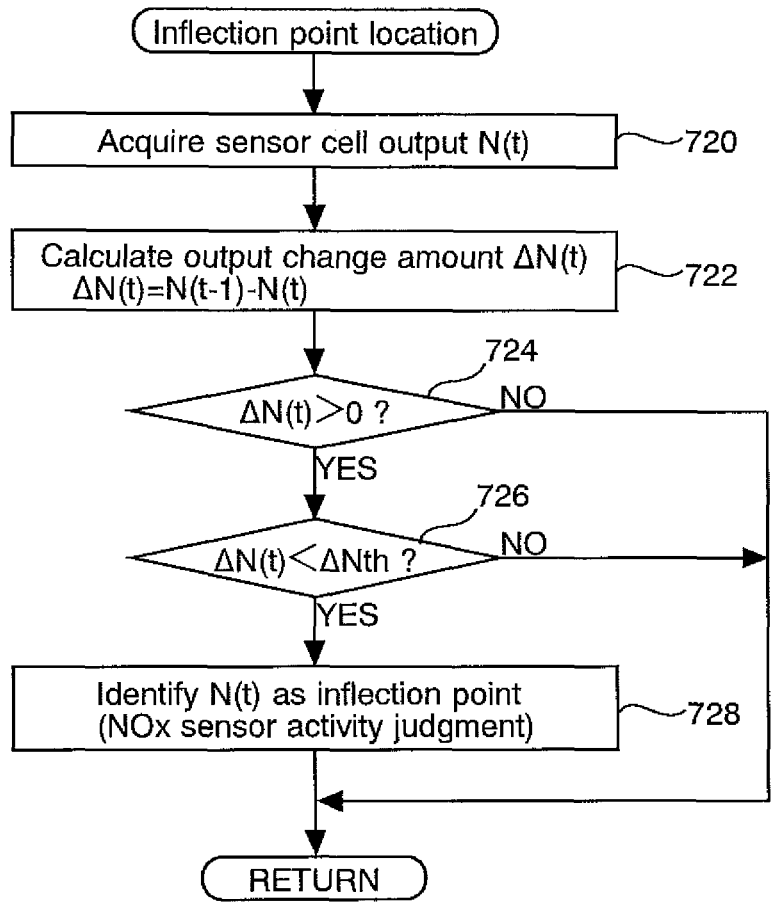
FIG. 17 is a flowchart illustrating an inflection point location routine that is executed in step 708 of FIG. 16.

FIG. 16 is a flowchart illustrating a routine that the ECU 8 executes in accordance with the sixth embodiment. FIG. 17 is a flowchart illustrating an inflection point location routine that is executed in step 708 of FIG. 16. The routine shown in FIG. 16 starts at predetermined intervals.

First of all, the routine shown in FIG. 16 performs step 700 to judge whether the ignition is ON. If the judgment result obtained in step 700 does not indicate that the ignition is ON, the routine terminates. If, on the other hand, the judgment result obtained in step 700 indicates that the ignition is ON, the routine performs step 702 to acquire the elapsed time between last power OFF and ignition ON. In step 702, for example, the routine reads the elapsed time calculated by another routine.

Next, the routine performs step 704 to judge whether the elapsed time acquired in step 702 is longer than a reference value. This reference value is used as a threshold value for judging whether the oxygen concentration has sufficiently increased since last power OFF. If the judgment result obtained in step 704 indicates that the elapsed time is not shorter than the reference value, the routine performs step 706 to turn ON the NOx sensor 1. In step 706, the ECU 8 causes the pump cell control means 81 to supply power to the oxygen pump cell 2, the sensor cell control means 82 to supply power to the NOx sensor cell 4, and the heater control means 83 to supply power to the heater electrode 61.

Subsequently, the routine proceeds to step 708 and locates an inflection point in the NOx sensor cell output. In step 708, the routine shown in FIG. 17 starts.

First of all, the routine shown in FIG. 17 performs step 720 to acquire the NOx sensor cell output N(t). The routine then performs step 722 to calculate the change amount ΔN(t) from Equation (5) below by using the NOx sensor cell output N(t) acquired in step 720.

$$\Delta N(t) = \Delta N(t-1) - \Delta N(t) \quad (5)$$

Subsequently, the routine performs step 724 to judge whether the change amount ΔN(t) calculated in step 722 is greater than zero (0) (that is, whether the change amount ΔN(t) is a positive value). More specifically, step 724 is performed to judge whether the current NOx sensor cell output N(t) is smaller than the last NOx sensor cell output N(t−1), that is, whether the NOx sensor cell output is decreased.

If the judgment result obtained in step 724 indicates that the change amount ΔN(t) is greater than zero (0), the routine concludes that the current NOx sensor cell output N(t) is smaller than the last NOx sensor cell output N(t−1), that is, the NOx sensor output is decreased. In this instance, the routine proceeds to step 726 and judges whether the change amount ΔN(t) is smaller than the reference value ΔNth. If the judgment result obtained in step 726 indicates that the change amount ΔN(t) is smaller than the reference value ΔNth, the routine performs step 728 to identify the NOx sensor cell output N(t) as an inflection point. Step 728 is performed to form an activity judgment about the NOx sensor 1. In the example shown in FIG. 3, the change amount ΔN(t14) is smaller than the reference value ΔNth; therefore, the NOx sensor cell output N(t14) at time t14 is identified as an inflection point. Subsequently, the routine shown in FIG. 17 terminates, allowing the routine shown in FIG. 16 to perform step 710.

In step 710 of the routine shown in FIG. 16, the information about the inflection point is acquired as a learned value. More specifically, in step 710, the NOx sensor cell output N(t) at the time of inflection point location, the time interval between sensor turn-ON and inflection point location, and a physical property value correlated to the element temperature prevailing at the time of inflection point location are stored as a three-dimensional map. Upon completion of step 710, the routine shown in FIG. 16 terminates.

If, on the other hand, the judgment result obtained in step 704 indicates that the elapsed time is shorter than the reference value, the routine performs step 712 to turn ON the NOx sensor 1 as is the case with step 706. The routine then proceeds to step 714 and judges whether the predetermined period of time a has elapsed after power ON in step 712. The predetermined period of time a permits the NOx sensor cell output to exceed the later-described reference value Nth2 (see FIG. 15) as far as a sufficient amount of oxygen exists in the NOx sensor 1. If the judgment result obtained in step 714 does not indicate that the predetermined period of time a has elapsed, the routine returns to step 712. If, on the other hand, the judgment result obtained in step 714 indicates that the predetermined period of time a has elapsed, the routine proceeds to step 716 and acquires the NOx sensor cell output N(a). The routine then performs step 718 to judge whether the NOx sensor cell output N(a) acquired in step 716 is not smaller than the reference value Nth2. The reference value Nth2 is used as a threshold value for judging whether an inflection point can be located in the NOx sensor cell output.

If the judgment result obtained in step 718 does not indicate that the NOx sensor cell output N(a) has reached the reference value Nth2 as indicated by the broken line Ls4 in FIG. 15, the routine concludes that an inflection point cannot be located, and that the information about an inflection point cannot be learned. In this instance, the routine shown in FIG. 16 terminates without locating an inflection point. If, on the other hand, the judgment result obtained in step 718 indicates that the NOx sensor cell output N(a) is not smaller than the reference value Nth2 as indicated by the two-dot chain line Ls3 in FIG. 15, the routine concludes that an inflection point can be located. In this instance, the routine proceeds to step 708.

As described above, the sixth embodiment allows the NOx sensor cell 4 to detect the NOx concentration after discharging the remaining oxygen with the oxygen pump cell 2. Therefore, when the concentration of oxygen in the NOx sensor 1 is high as at engine start, the NOx sensor cell output changes shown in FIG. 2 are obtained. The inflection point appearing in the NOx sensor cell output indicates that the NOx sensor cell 4 can detect the NOx concentration without being affected by the remaining oxygen. In marked contrast to a common sensor activity (full activity) judgment, the sixth embodiment concludes, when the inflection point appears, that the NOx sensor 1 is active. It means that the sixth embodiment forms an accurate activity judgment about the NOx sensor 1 in accordance with the inflection point, which appears in the NOx sensor cell output irrespective of individual sensor differences, and not in accordance, for instance, with element impedance, which varies from one sensor unit to another. This makes it possible not only to accomplish early activation of the NOx sensor 1 to the utmost extent, but also to fulfill the demand for emission reduction by using an accurate NOx sensor cell output for various control operations.

Further, the sixth embodiment stores the information about an inflection point as a learned value after locating the inflection point in the NOx sensor cell output. For example, the sixth embodiment stores the NOx sensor cell output prevailing at the time of inflection point location, the time interval between sensor turn-ON and inflection point location, and a physical property value correlated to the element temperature prevailing at the time of inflection point location as a three-dimensional map. Therefore, such a learned value can be used to reduce activity judgment variations caused by the difference in the engine operating status. Particularly, it is possible to reduce activity judgment variations caused by the difference in engine startup conditions (the elapsed time from last power OFF). In addition, learning is performed at engine start to ensure sufficient learning frequency.

The sixth embodiment, which has been described above, uses a learned value to reduce activity judgment variations caused by the difference in the engine operating status. However, the learned value may alternatively be used to form a deterioration judgment about the NOx sensor 1. More specifically, the sixth embodiment, which has been described above, makes it possible to accurately learn an inflection point (active site). Therefore, the accuracy of NOx sensor deterioration judgment can be effectively increased by comparing a NOx sensor cell output value obtained after such learning against a predetermined value for deterioration judgment purposes.

Further, the sixth embodiment, which has been described above, locates an inflection point in accordance, for instance, with a comparison between the NOx sensor cell output change amount ΔN(t) and reference value ΔNth, as is the case with the routine shown in FIG. 17. Alternatively, however, the inflection point may be located by methods according to the following modifications of the sixth embodiment.

(First Modification)

Figure 18:
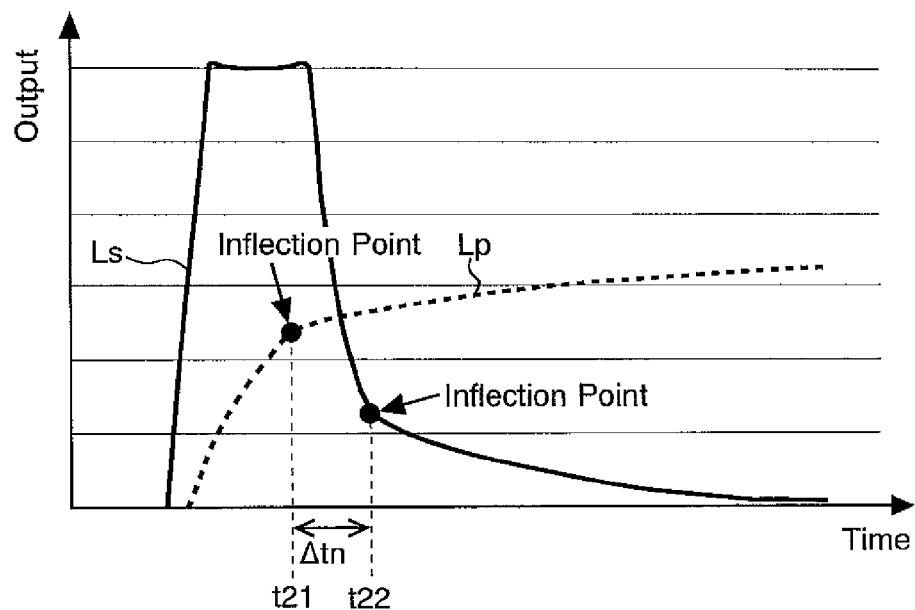
FIG. 18 is a diagram illustrating the correlation between the oxygen pump cell output and NOx sensor cell output.

The oxygen pump cell 2 and the NOx sensor cell 4 have the same configuration and both output the value of a current that prevails when oxygen ions $O^{2-}$ flow in the cells. Therefore, there is a correlation between the oxygen pump cell output and the NOx sensor cell output. A first modification of the sixth embodiment uses such a correlation to locate an inflection point in the NOx sensor cell output. FIG. 18 is a diagram illustrating the correlation between the oxygen pump cell output and NOx sensor cell output. In FIG. 18, a broken line Lp indicates oxygen pump cell output changes, whereas a solid line Ls indicates NOx sensor cell output changes.

When the NOx sensor 1 turns ON, an inflection point appears not only in the NOx sensor cell output but also in the oxygen pump cell output as shown in FIG. 18. The inflection point in the oxygen pump cell output appears when the oxygen remaining in the first internal space 31 is discharged. The inventor of the present invention has found that there is a correlation between time t21, at which an inflection point appears in the oxygen pump cell output, and time t22, at which an inflection point appears in the NOx sensor cell output.

The difference Δtn between time t21 and time t22 can be predetermined, for instance, by an experiment and stored in the ECU 8. Therefore, when the time at which an inflection point appears in the oxygen pump cell output can be determined by a later-described method, the time at which an inflection point appears in the NOx sensor cell output can be estimated by adding the predetermined difference Δtn to the determined time of inflection point appearance in the oxygen pump cell output.

Figure 19:
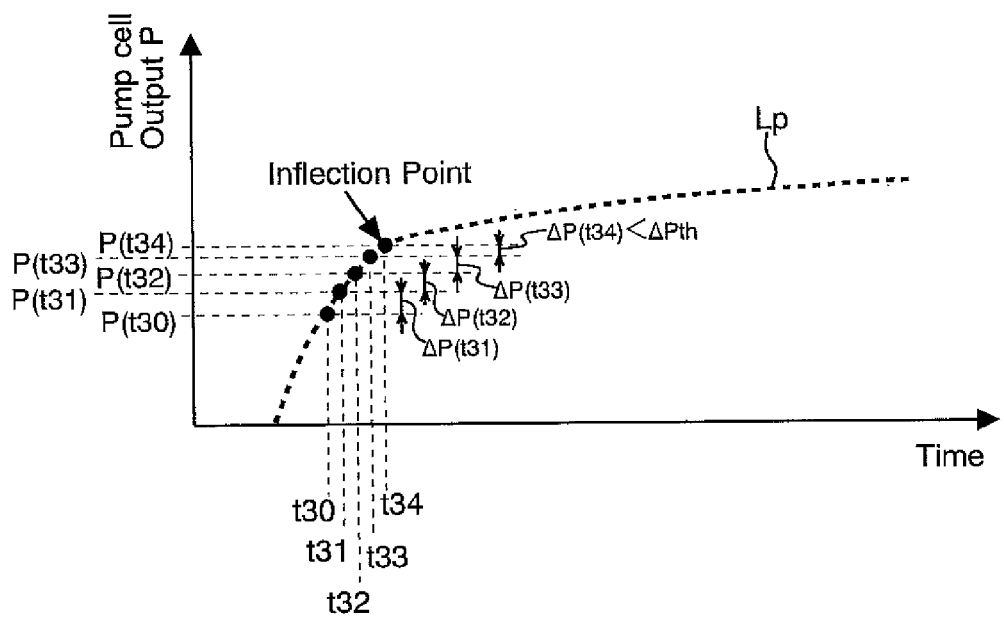
FIG. 19 is a diagram illustrating a method of locating an inflection point in the oxygen pump cell output in accordance with a first modification of the sixth embodiment of the present invention.

A method of locating an inflection point in the oxygen pump cell output will now be described with reference to FIG. 19. FIG. 19 is a diagram illustrating a method of locating an inflection point in the oxygen pump cell output in accordance with the first modification of the sixth embodiment. The method of locating an inflection point in the NOx sensor cell output, which has been described in conjunction with the sixth embodiment, can be partially applied to the method of locating an inflection point in the oxygen pump cell output.

First of all, the first modification of the sixth embodiment not only acquires the oxygen pump cell output P at predetermined intervals, but also calculates the oxygen pump cell output change amount ΔP upon each oxygen pump cell output acquisition. The amount of change ΔP(t) at time t can be calculated from Equation (6) below. When the calculated change amount ΔP(t) is smaller than a predetermined reference value ΔPth, the oxygen pump cell output P(t) prevailing at time t is identified as an inflection point. In Equation (6) below, the output P(t−1) at time t−1 is subtracted from the output P(t) at time t so that the change amount ΔP(t) is a positive value.

$$\Delta P(t)=P(t)-P(t-1) \tag{6}$$

In the example shown in FIG. 19, the oxygen pump cell output P increases between time t30 and time t34. Therefore, the change amounts ΔP(t31) to ΔP(t34) calculated from Equation (6) above at time t31, time t32, time t33, and time t34 are all positive values. The change amounts ΔP(t31) to ΔP(t33) are not smaller than the predetermined reference value ΔPth. However, the change amount ΔP(t34) is smaller than the reference value ΔPth. Therefore, the oxygen pump cell output P(t34) prevailing at time t34 is identified as an inflection point. Consequently, it can be estimated that an inflection point appears in the NOx sensor cell output N at time t34+Δtn, which is determined by adding Δtn to time t34.

Figure 20:
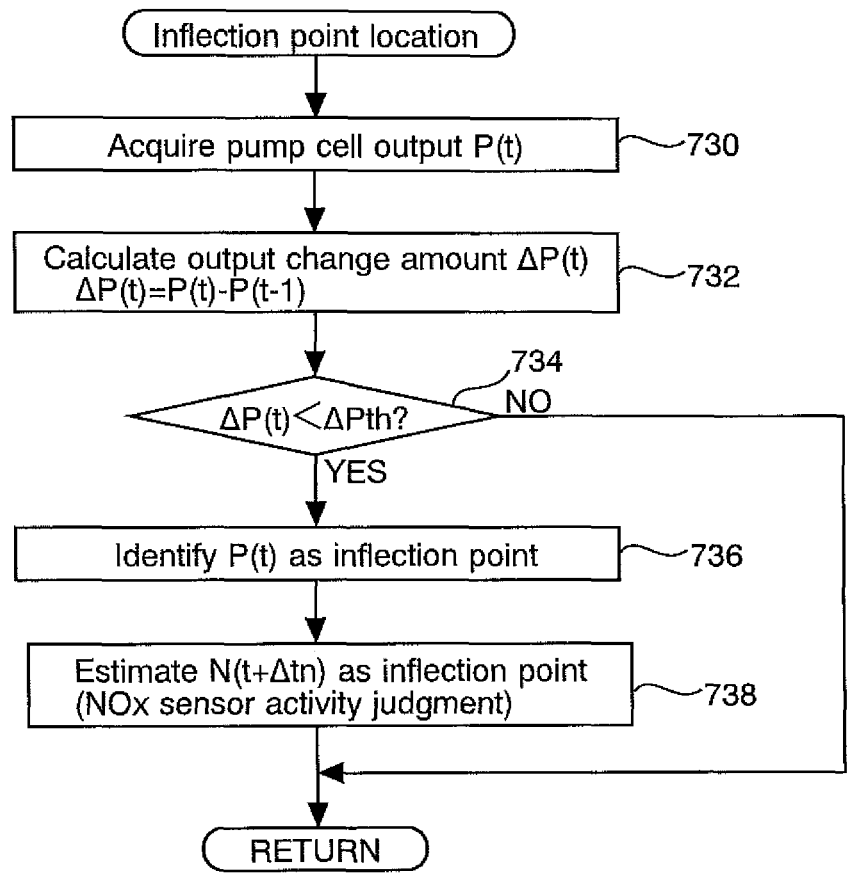
FIG. 20 is a flowchart illustrating an inflection point location routine according to the first modification of the sixth embodiment of the present invention.

FIG. 20 is a flowchart illustrating an inflection point location routine according to the first modification of the sixth embodiment. The routine shown in FIG. 20 starts in step 708 of the routine shown in FIG. 16. First of all, the routine shown in FIG. 20 performs step 730 to acquire the oxygen pump cell output P(t). The routine then performs step 732 to calculate the change amount ΔP(t) from Equation (6) above by using the oxygen pump cell output P(t) acquired in step 730.

Next, the routine performs step 734 to judge whether the change amount ΔP(t) calculated in step 732 is smaller than the reference value ΔPth. If the judgment result obtained in step 734 indicates that the change amount ΔP(t) is not smaller than the reference value ΔPth, the routine shown in FIG. 20 terminates because it concludes that an inflection point has not appeared in the oxygen pump cell output P.

If, on the other hand, the judgment result obtained in step 734 indicates that the change amount ΔP(t) is smaller than the reference value ΔPth, the routine shown in FIG. 20 performs step 736 to identify the oxygen pump cell output P(t) at time t as an inflection point. The routine then performs step 738 to estimate the inflection point in the NOx sensor cell output in consideration of the correlation between the oxygen pump cell output P and NOx sensor cell output N by using the inflection point located in step 736.

Here, the time difference Δtn between time t21, at which an inflection point appears in the oxygen pump cell output, and time t22, at which an inflection point appears in the NOx sensor cell output, is predetermined as shown in FIG. 18, and stored in the ECU 8. It is estimated in step 738 that an inflection point appears in the NOx sensor cell output at time t+Δtn, which is determined by adding the time difference Δtn to the time t at which an inflection point appears in the oxygen pump cell output. At time t+Δtn, an activity judgment about the NOx sensor 1 is formed. The routine terminates upon completion of NOx sensor cell activity judgment.

The first modification of the sixth embodiment determines the time at which an inflection point appears in the oxygen pump cell output P, considers the correlation between the oxygen pump cell output P and the NOx sensor cell output N, and estimates the time at which an inflection point appears in the NOx sensor cell output N. This makes it possible to accurately estimate the time at which the NOx sensor cell 4 begins to detect the NOx concentration with high accuracy.

(Second Modification)

Figure 21:
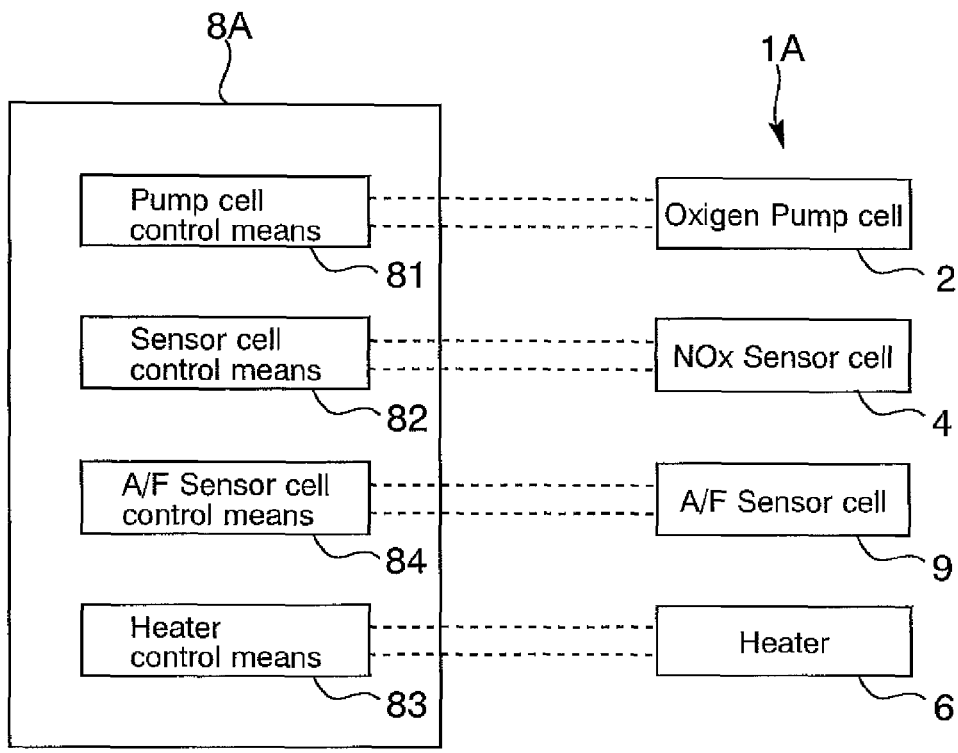
FIG. 21 is a block diagram illustrating essential parts of the gas concentration detection apparatus according to a second modification of the sixth embodiment of the present invention.

The first modification of the sixth embodiment considers the correlation between the oxygen pump cell output P and the NOx sensor cell output N, and estimates the time at which an inflection point appears in the NOx sensor cell output N. FIG. 21 is a block diagram illustrating essential parts of the gas concentration detection apparatus according to a second modification of the sixth embodiment of the present invention. The gas concentration detection apparatus shown in FIG. 21 includes a NOx sensor 1A. The NOx sensor 1A is obtained by incorporating an air-fuel ratio sensor cell 9 into the NOx sensor 1 shown in FIG. 1. The air-fuel ratio sensor cell 9 includes a solid electrolyte body (not shown) and outputs the value of a current that prevails when oxygen ions $O^{2-}$ flow in the cell to which the predetermined voltage is applied. The output of the air-fuel ratio sensor cell 9 is detected by air-fuel ratio sensor cell control means 84 in an ECU 8A. The other portion of the gas concentration detection apparatus will not be described in drawings or in words because it has the same configuration as the gas concentration detection apparatus 10 shown in FIG. 1.

The air-fuel ratio sensor cell 9 and the NOx sensor cell 4 both output the value of a current that prevails when oxygen ions $O^{2-}$ flow in the cells. Therefore, there is a correlation between the output of the air-fuel ratio sensor cell and the output of the NOx sensor cell. The second modification of the sixth embodiment uses such a correlation to locate an inflection point in the NOx sensor cell output.

Figure 22:
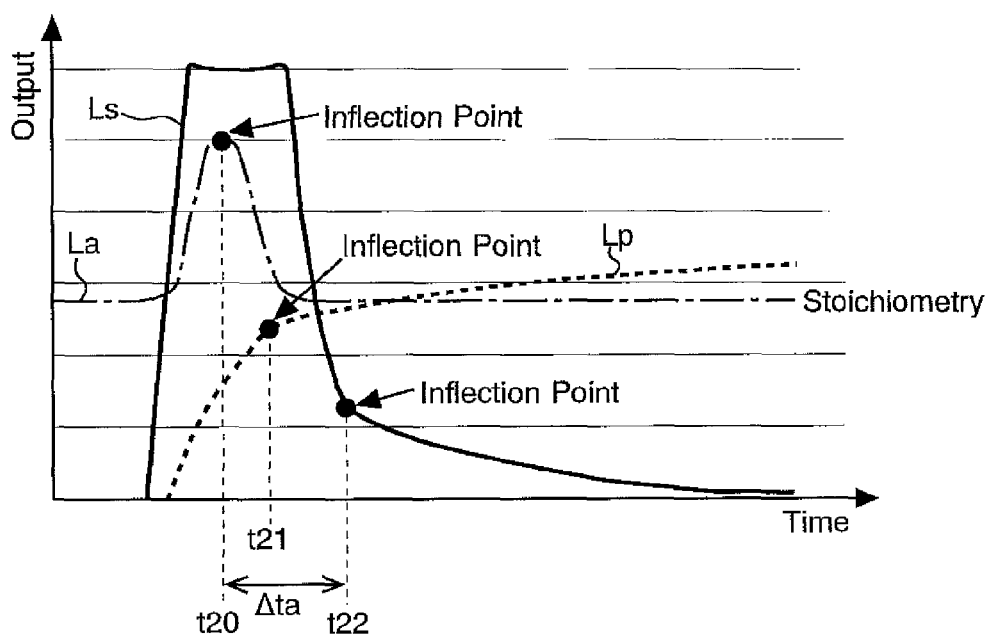
FIG. 22 is a diagram illustrating the correlation between an air-fuel ratio sensor cell output and NOx sensor cell output.

FIG. 22 is a diagram illustrating the correlation between an air-fuel ratio sensor cell output and NOx sensor cell output. In FIG. 22, a one-dot chain line La indicates air-fuel ratio sensor cell output changes, whereas a solid line Ls indicates NOx sensor cell output changes. A broken line Lp in FIG. 22 indicates oxygen pump cell output changes for reference purposes.

As shown in FIG. 22, an inflection point appears not only in the NOx sensor cell output but also in the air-fuel ratio sensor cell output. The inflection point may be defined, for instance, as an air-fuel ratio sensor cell output that is generated when the amount of change in the air-fuel ratio sensor cell output changes from positive to negative. There is a correlation between time t20, at which an inflection point appears in the air-fuel ratio sensor cell output, and time t22, at which an inflection point appears in the NOx sensor cell output. The difference Δta between time t20 and time t22 can be predetermined, for instance, by an experiment and stored in the ECU 8A. Therefore, when the inflection point in the air-fuel ratio sensor cell output can be located, the time at which an inflection point appears in the NOx sensor cell output can be estimated. Consequently, the second modification makes it possible to accurately estimate the time at which the NOx sensor cell 4 begins to detect the actual NOx concentration with high accuracy, as is the case with the first modification, which has been described earlier.

The sixth embodiment, which has been described above, uses the engine control ECU 8 to control the NOx sensor 1. Alternatively, however, a NOx sensor control ECU may be employed in addition to the engine control ECU 8.

In the sixth embodiment and its modifications, the NOx sensor cell 4 corresponds to the "gas concentration detection cell" according to the first aspect of the present invention; the heater electrode 61 corresponds to the "heater" according to the seventeenth aspect of the present invention; the heater control means 83 corresponds to the "heater control means" according to the seventeenth aspect of the present invention; the oxygen pump cell 2 corresponds to the "oxygen pump cell" according to the seventeenth or eighteenth aspect of the present invention; and the pump cell control means 81 corresponds to the "oxygen pump cell control means" according to the eighteenth aspect of the present invention.

Further, in the sixth embodiment and its modifications, the "oxygen concentration control means" according to the first aspect of the present invention is implemented when the ECU 8 performs steps 702 and 704; and the "inflection point location means" according to the fifteenth aspect of the present invention is implemented when the ECU 8 performs step 708, 728, or 738; and the "inflection point learned value storage means" according to the fifteenth aspect of the present invention is implemented when the ECU 8 performs step 710.

Seventh Embodiment

A seventh embodiment of the present invention will now be described with reference to FIGS. 23 and 24. A system according to the seventh embodiment is implemented when the hardware configuration shown in FIGS. 1 and 14 is employed to let the ECU 8 execute routines shown in FIGS. 16 and 24.

Features of Seventh Embodiment

The sixth embodiment, which has been described earlier, learns the information about an inflection point at engine start. Meanwhile, NOx exists downstream of the SCR catalyst 122 at engine start because the activity of the SCR catalyst 122 is low. FIG. 23 is a diagram illustrating NOx concentration changes occurring downstream of the SCR catalyst 122 at engine start and NOx sensor cell output changes. In FIG. 23, a thick solid line Ls indicates NOx sensor cell output changes, whereas a thin solid line L indicates NOx concentration measurements taken downstream of the SCR catalyst 122. These measurements are taken with a publicly known analyzer.

Figure 23:
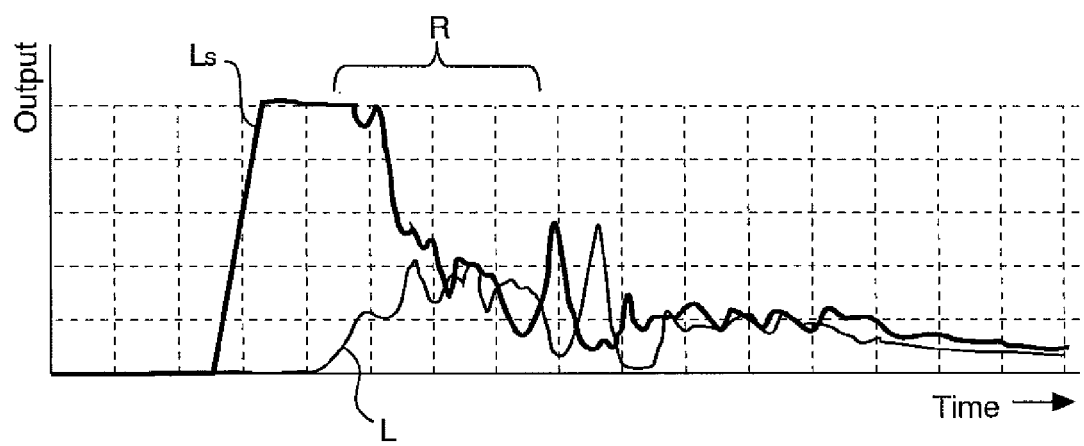
FIG. 23 is a diagram illustrating NOx concentration changes occurring downstream of an SCR catalyst 122 at engine start and NOx sensor cell output changes.

When the NOx concentration prevailing downstream of the SCR catalyst 122 changes, the NOx sensor cell output changes as shown in FIG. 23. Within the region R shown in FIG. 23, an inflection point normally appears in the NOx sensor cell output. However, the inflection point in the NOx sensor cell output may not accurately be located due to NOx sensor cell output changes caused by NOx concentration changes.

In view of the above circumstances, the seventh embodiment estimates the NOx concentration by a publicly known method and corrects the NOx sensor cell output in accordance with the estimated NOx concentration value. More specifically, the seventh embodiment corrects the NOx sensor cell output by estimating the NOx concentration, for instance, from the EGR amount or fuel injection amount and subtracting the estimated value from an actual NOx sensor cell output. The seventh embodiment then locates an inflection point in the corrected NOx sensor cell output.

[Details of Process Performed by Seventh Embodiment]

The seventh embodiment also starts the routine shown in FIG. 16 in the first place. Then, in step 708 of the routine shown in FIG. 16, the seventh embodiment starts a routine shown in FIG. 24 instead of the routine shown in FIG. 17. FIG. 24 is a flowchart illustrating an inflection point location routine that is executed in step 708 of FIG. 16 in accordance with the seventh embodiment.

Figure 24:
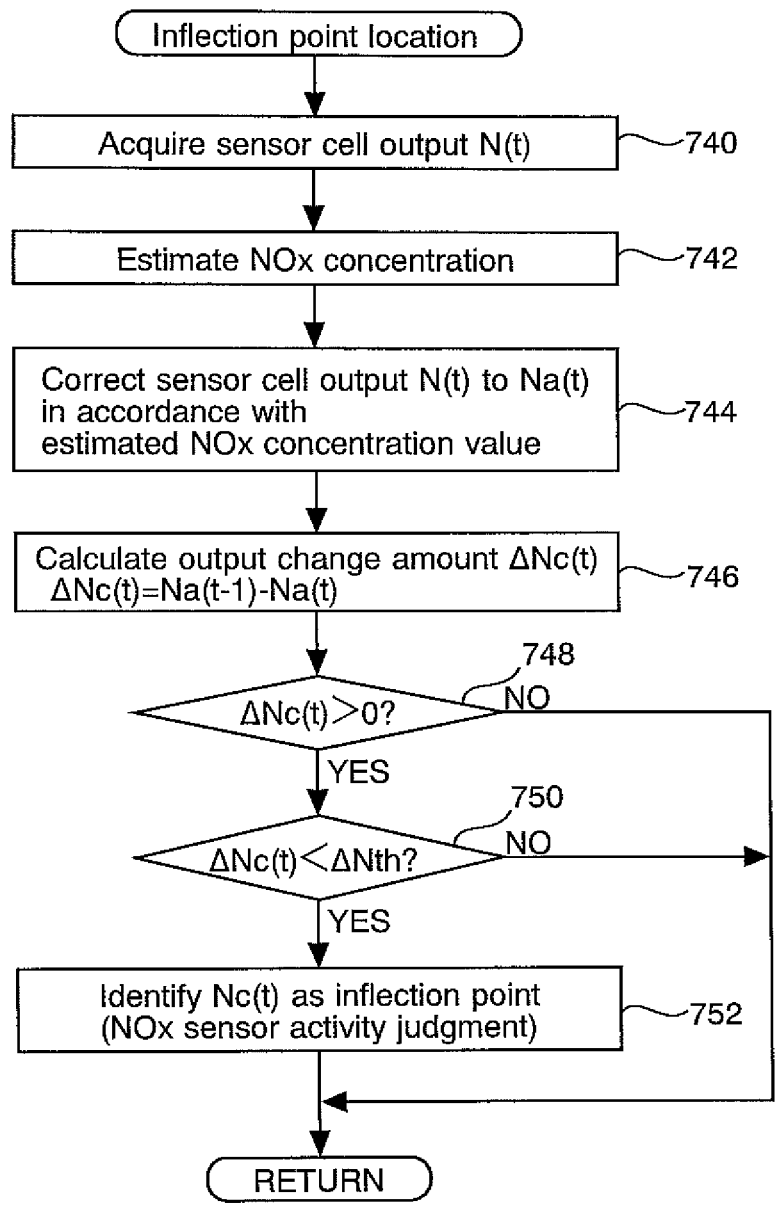
FIG. 24 is a flowchart illustrating an inflection point location routine that is executed in step 708 of FIG. 16 in accordance with a seventh embodiment of the present invention.

First of all, the routine shown in FIG. 24 performs step 740 to acquire the NOx sensor cell output N(t) as is the case with the routine shown in FIG. 17. The routine then performs step 742 to estimate the NOx concentration prevailing downstream of the SCR catalyst 122 by a publicly known method. In step 742, an estimated value of the NOx concentration is obtained in accordance, for instance, with the EGR amount or fuel injection amount.

Subsequently, the routine performs step 744 to correct the NOx sensor cell output N(t) acquired in step 740 to Nc(t) in accordance with the estimated NOx concentration value obtained in step 742. In step 744, the correction is made to obtain the NOx sensor cell output Nc(t), for instance, by subtracting the estimated NOx concentration value from the NOx sensor cell output N(t). Next, the routine performs step 746 to calculate a change amount $\Delta Nc(t)$ from Equation (7) below by using the NOx sensor cell output Nc(t) corrected in step 744.

$$\Delta Nc(t) = Nc(t-1) - Nc(t) \tag{7}$$

Next, the routine performs step 748 to judge whether the change amount $\Delta Nc(t)$ calculated in step 746 is greater than zero (0) (that is, whether the change amount $\Delta Nc(t)$ is a positive value). More specifically, step 748 is performed to judge whether the current NOx sensor cell output Nc(t) is smaller than the last NOx sensor cell output Nc(t−1), that is, whether the NOx sensor cell output Nc(t) is decreased.

If the judgment result obtained in step 748 indicates that the change amount $\Delta Nc(t)$ is greater than zero (0), the routine concludes that the current NOx sensor cell output Nc(t) is smaller than the last NOx sensor cell output Nc(t−1), that is, the NOx sensor cell output Nc(t) is decreased. In this instance, the routine proceeds to step 750 and judges whether the change amount $\Delta Nc(t)$ is smaller than the reference value $\Delta Nth$.

If the judgment result obtained in step 750 indicates that the change amount $\Delta Nc(t)$ is smaller than the reference value $\Delta Nth$, the routine performs step 752 to identify the NOx sensor cell output Nc(t) as an inflection point. Step 752 is performed to form an activity judgment about the NOx sensor 1. Subsequently, the routine shown in FIG. 24 terminates, allowing the routine shown in FIG. 16 to proceed to step 710 and learn the information about the inflection point.

As described above, the seventh embodiment obtains the estimated NOx concentration value at engine start, corrects the NOx sensor cell output N in accordance with the estimated NOx concentration value, and locates an inflection point in the corrected NOx sensor cell output Nc. This makes it possible to accurately locate an inflection point at engine start without being affected by changes in the concentration of NOx emitted from the engine 100 and learn the information about the inflection point with high accuracy. Consequently, the resulting learned value can be used to reduce activity judgment variations caused by the difference in the engine operating status.

The seventh embodiment, which has been described above, uses the learned value to reduce activity judgment variations caused by the difference in the engine operating status. However, the learned value may be used to form a deterioration judgment about the NOx sensor 1. More specifically, the seventh embodiment, which has been described above, makes it possible to accurately learn an inflection point (active site). Therefore, the accuracy of NOx sensor deterioration judgment can be effectively increased by comparing a NOx sensor cell output value obtained after such learning against a predetermined value for deterioration judgment purposes.

In the seventh embodiment, the "NOx concentration estimation means" according to the sixteenth aspect of the present invention is implemented when the ECU 8 performs step 742; the "correction means" according to the sixteenth aspect of the present invention is implemented when the ECU 8 performs step 744; and the "inflection point location means" according to the sixteenth aspect of the present invention is implemented when the ECU 8 performs step 752.

Eighth Embodiment

An eighth embodiment of the present invention will now be described with reference to FIG. 25.

A system according to the eighth embodiment is implemented when the hardware configuration shown in FIGS. 1 and 14 is employed to let the ECU 8 execute a later-described routine shown in FIG. 25.

Features of Eighth Embodiment

The seventh and eighth embodiments learn the information about an inflection point at engine start. The eighth embodiment will be described with reference to a case where the inflection point information is learned when a fuel cut (F/C) is performed. To locate an inflection point in the NOx sensor cell output, it is necessary to increase the concentration of oxygen in the NOx sensor 1 as described earlier.

Consequently, the power supply from the heater control means 83 to the heater electrode 61 is shut off in order to increase the concentration of oxygen in the NOx sensor 1 during a fuel cut. The element temperature then lowers to decrease the oxygen pumping capacity of the oxygen pump cell 2. This increases the concentration of oxygen in the NOx sensor 1, that is, the concentration of oxygen in the first and second internal spaces 31, 32 and the concentration of oxygen absorbed by the first detection electrode 42 in the NOx sensor cell 4.

The concentration of oxygen in the NOx sensor 1 is governed not only by the responsiveness of the NOx sensor 1 but also by the intake air amount Ga of the engine 100. Therefore, an integrated air amount Qa, which is an integrated value of the intake air amount Ga, is compared against a reference value Qth to judge whether the concentration of oxygen in the NOx sensor 1 is increased to a desired level. In other words, whether an inflection point can be located is determined in accordance with the integrated air amount Qa. More specifically, an inflection point in the NOx sensor cell output is located when the integrated air amount Qa is greater than the reference value Qth.

The inflection point location method and inflection point information learning method according to the sixth embodiment can be applied to the eighth embodiment. It should be noted in this connection that NOx generation does not take place during a fuel cut because no in-cylinder explosion occurs. Therefore, it is not necessary to correct the NOx sensor cell output as described in conjunction with the seventh embodiment.

[Details of Process Performed by Eighth Embodiment]

Figure 25:
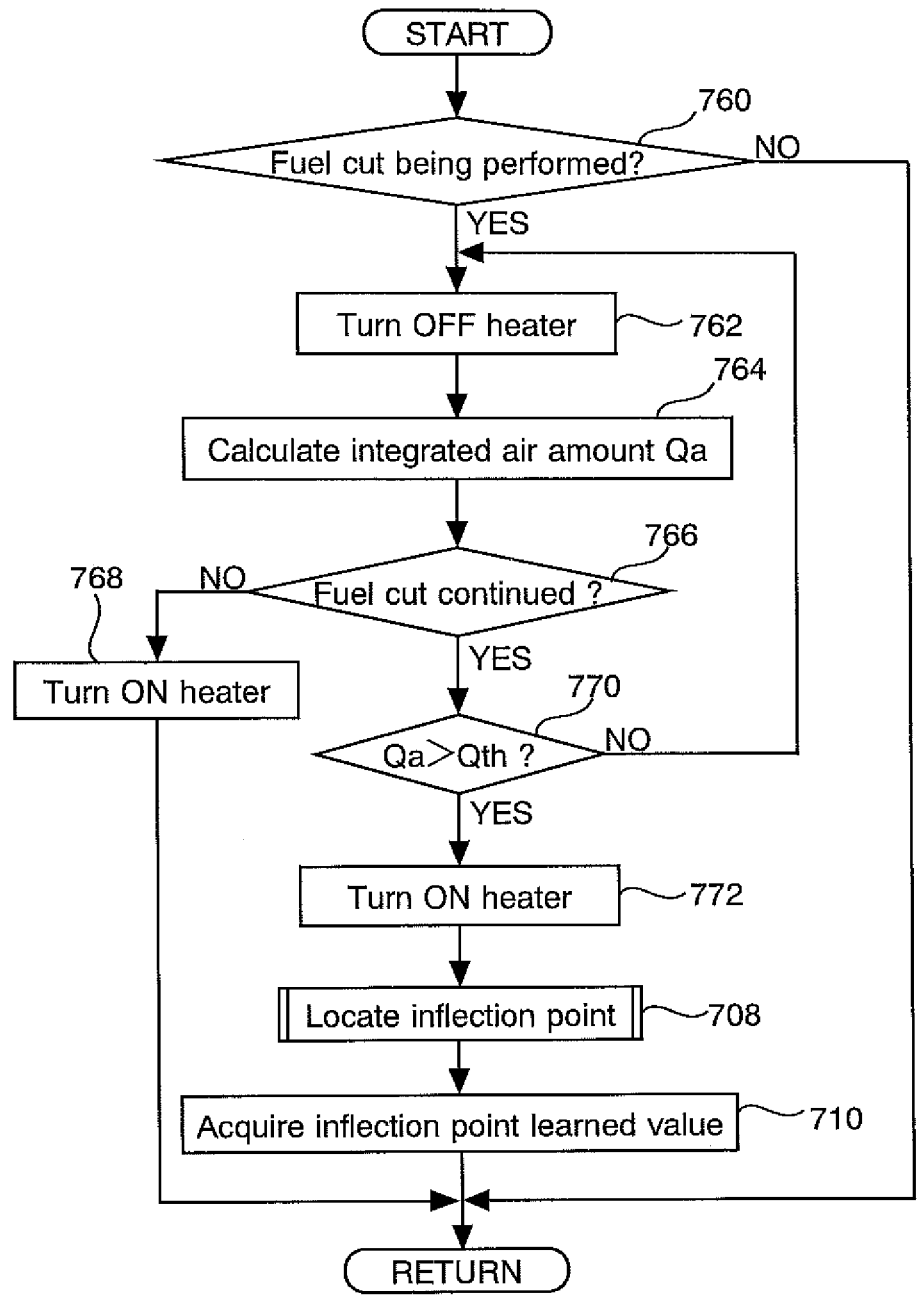
FIG. 25 is a flowchart illustrating a routine that the ECU 8 executes in accordance with an eighth embodiment of the present invention.

FIG. 25 is a flowchart illustrating a routine that the ECU 8 executes in accordance with the eighth embodiment. First of all, the routine shown in FIG. 25 performs step 760 to judge whether a fuel cut is being performed. A fuel cut is performed so that the fuel injection amount is reduced to zero when the accelerator opening AA is placed in a fully-closed state during a vehicle run. If the judgment result obtained in step 760 does not indicate that a fuel cut is being performed, the routine terminates.

If, on the other hand, the judgment result obtained in step 760 indicates that a fuel cut is being performed, the routine performs step 762 to shut off the power supply to the heater electrode 61. Performing step 762 reduces the oxygen pumping capacity of the oxygen pump cell 2 and gradually increases the concentration of oxygen in the NOx sensor 1.

Next, the routine performs step 764 to calculate the integrated air amount Qa. In step 764, the integrated air amount Qa is obtained by determining an integrated intake air amount Ga that is reached after the power supply to the heater electrode 61 was shut off.

Subsequently, the routine performs step 766 to judge whether a fuel cut is being continuously performed. If the judgment result obtained in step 766 does not indicate that a fuel cut is being continuously performed, that is, when, for instance, the accelerator is depressed by a vehicle driver or a fuel cut recovery rotation speed is reached by the engine speed NE, the routine performs step 768 to supply power to the heater electrode 61. Upon completion of step 768, the routine terminates so that the NOx sensor cell output is used for the other control operations.

If, on the other hand, the judgment result obtained in step 766 indicates that a fuel cut is being continuously performed, the routine performs step 770 to judge whether the integrated air amount Qa calculated in step 764 is greater than the reference value Qth. The reference value Qth is used as a threshold value for judging whether the concentration of oxygen in the NOx sensor 1 is increased to a desired level. If the judgment result obtained in step 770 indicates that the integrated air amount Qa is smaller than the reference value Qth, the routine concludes that the concentration of oxygen in the NOx sensor 1 is not increased to the desired level. In other words, the routine concludes that an inflection point in the NOx sensor cell output cannot be located, and that the information about an inflection point cannot be learned. In this instance, the routine returns to step 762.

If, on the other hand, the judgment result obtained in step 770 indicates that the integrated air amount Qa is greater than the reference value Qth, the routine concludes that the concentration of oxygen in the NOx sensor 1 is increased to the desired level. In this instance, the routine performs step 772 to supply power from the heater control means 83 to the heater electrode 61. The routine then proceeds to step 708 and executes the routine shown in FIG. 17 to locate an inflection point. Subsequently, the routine performs step 710 to acquire an inflection point learned value as is the case with the routine shown in FIG. 16. Upon completion of step 710, the routine terminates.

As described above, the eighth embodiment increases the concentration of oxygen in the NOx sensor 1 by shutting off the power supply to the heater electrode 61 during a fuel cut. When the integrated air amount Qa is greater than the reference value Qth, the eighth embodiment concludes that the concentration of oxygen in the NOx sensor 1 is increased to the desired level, and then locates an inflection point in the NOx sensor cell output. This makes it possible to locate an inflection point and learn the information about the inflection point even during a fuel cut. Therefore, the resulting learned value can be used to reduce activity judgment variations caused by the difference in the engine operating status. In addition, learning is performed during a fuel cut to ensure sufficient learning frequency.

The eighth embodiment, which has been described above, uses the above-described learned value to reduce activity judgment variations caused by the difference in the engine operating status. However, the learned value may alternatively be used to form a deterioration judgment about the NOx sensor 1. More specifically, the eighth embodiment, which has been described above, makes it possible to accurately learn an inflection point (active site). Therefore, the accuracy of NOx sensor deterioration judgment can be effectively increased by comparing a NOx sensor cell output value obtained after such learning against a predetermined value for deterioration judgment purposes.

Modifications of the eighth embodiment will now be described. The eighth embodiment, which has been described above, shuts off the power supply to the heater electrode 61 in order to increase the concentration of oxygen in the NOx sensor 1. Alternatively, however, the concentration of oxygen in the NOx sensor 1 may be increased by methods according to the following modifications, which differ from the eighth embodiment.

(First Modification)

When the power supply to the heater electrode 61 is shut off during a fuel cut as described in conjunction with the eighth embodiment, which has been described above, the element temperature suddenly lowers. Then, the element temperature does not rise for the time being even when the power supply is performed for fuel cut discontinuation. Consequently, the NOx sensor cell output cannot be used for the other control operations. As a result, the exhaust emission characteristics may deteriorate before the element temperature rises.

Figure 26:
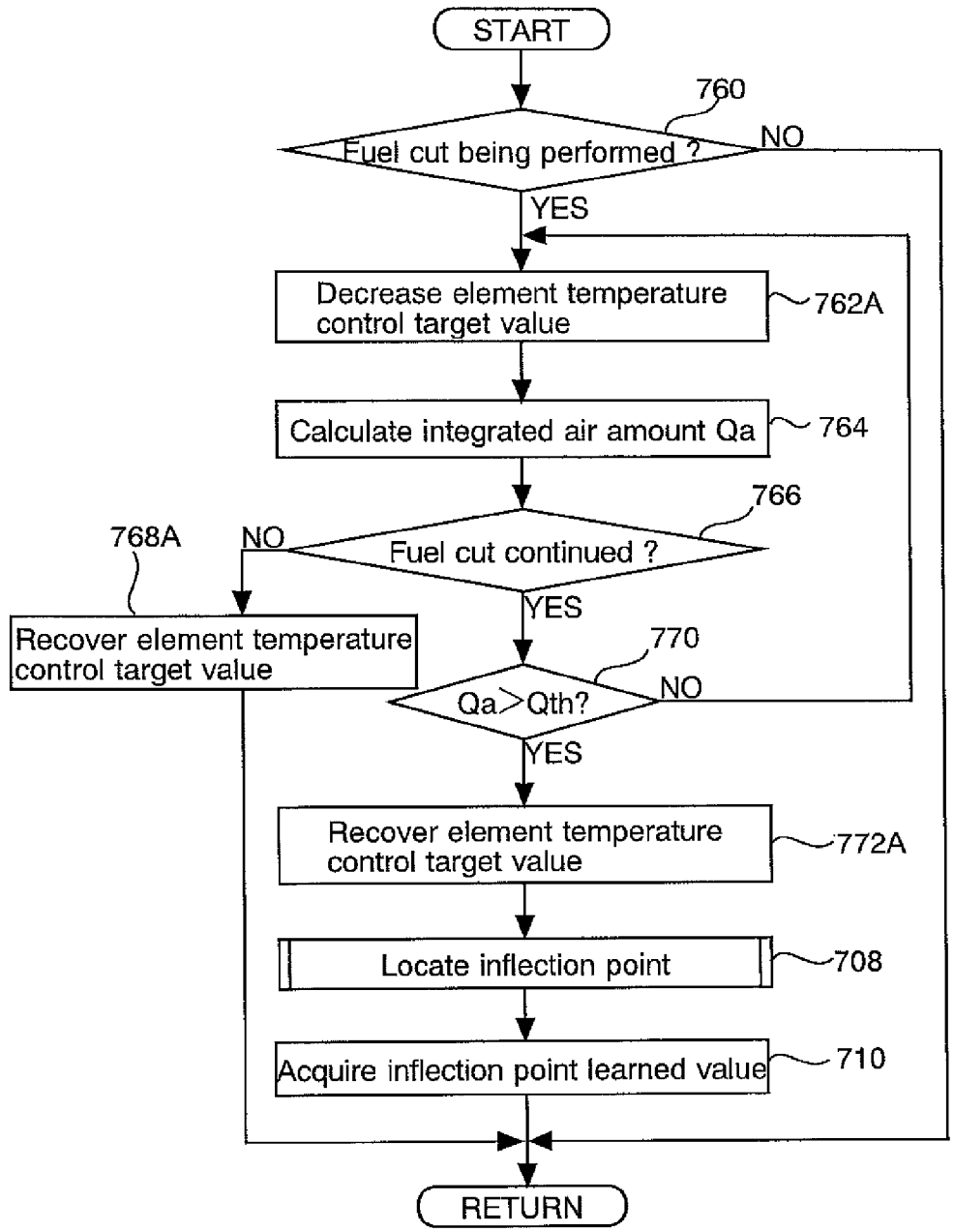
FIG. 26 is a flowchart illustrating a routine that the ECU 8 executes in accordance with a first modification of the eighth embodiment of the present invention.

According to a first modification of the eighth embodiment, an element temperature control target value is decreased during a fuel cut, as shown in FIG. 26, in order to increase the concentration of oxygen in the NOx sensor 1. FIG. 26 is a flowchart illustrating a routine that the ECU 8 executes in accordance with the first modification of the eighth embodiment. The routine shown in FIG. 26 differs from the routine shown in FIG. 25 in that the former performs steps 762A, 768A, and 772A instead of steps 762, 768, and 772. These differences will be described below.

If the judgment result obtained in step 760 indicates that a fuel cut is being performed, the routine shown in FIG. 26 performs step 762A to decrease a control target value of the element temperature. More specifically, the routine decreases the control target value for the heater control means 83. This ensures that the period of power supply to the heater electrode 61 is shorter than normal. Consequently, the element temperature lowers to reduce the oxygen discharge capacity of the oxygen pump cell 2. As a result, it is possible to increase the concentration of oxygen in the NOx sensor 1, that is, the concentration of oxygen in the first and second internal spaces 31, 32 and the concentration of oxygen absorbed by the first detection electrode 42.

The element temperature decrease caused by the above-described control target value decrease is smaller than when the power supply is shut off in accordance with the eighth embodiment. Therefore, when the control target value is restored to normal (step 768A) in a situation where a fuel cut is going to be discontinued, the element temperature can be raised earlier as compared to the eighth embodiment. Consequently, the deterioration of exhaust emission characteristics can be suppressed before an element temperature rise as compared to the eighth embodiment.

Further, if the judgment result obtained in step 770 indicates that the integrated air amount Qa is greater than the reference value Qth, step 772A is performed to recover the control target value of the element temperature. Step 708 is then performed to locate an inflection point. Next, step 710 is performed to acquire an inflection point learned value.

(Second Modification)

Figure 27:
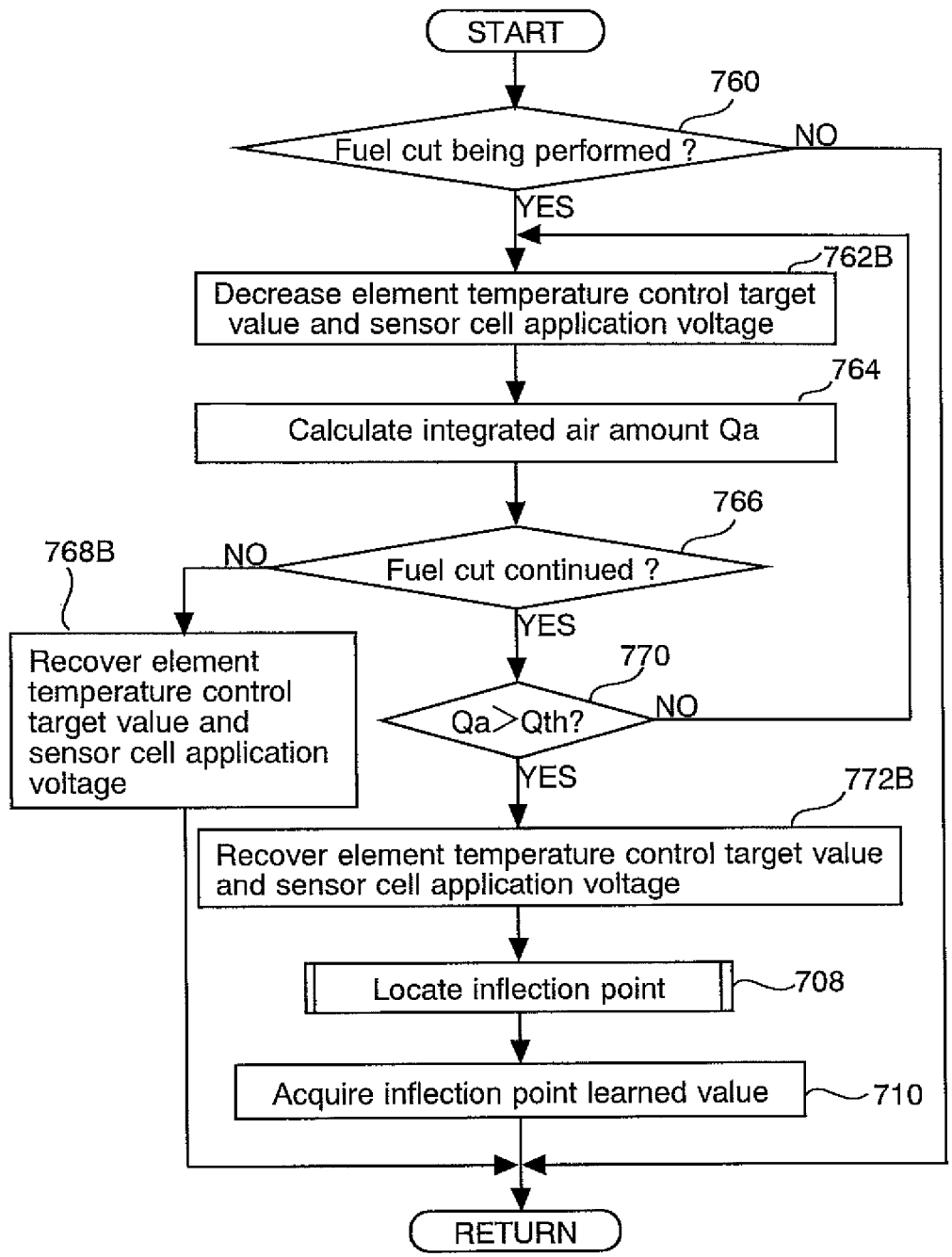
FIG. 27 is a flowchart illustrating a routine that the ECU 8 executes in accordance with a second modification of the eighth embodiment of the present invention.

To increase the concentration of oxygen in the NOx sensor 1 during a fuel cut, a second modification of the eighth embodiment not only decreases the control target value of the element temperature but also lowers the voltage applied to the NOx sensor cell 4, as shown in FIG. 27. FIG. 27 is a flowchart illustrating a routine that the ECU 8 executes in accordance with the second modification of the eighth embodiment. The routine shown in FIG. 27 differs from the routine shown in FIG. 25 in that the former performs steps 762B, 768B, and 772B instead of steps 762, 768, and 772. These differences will be described below.

If the judgment result obtained in step 760 indicates that a fuel cut is being performed, the routine shown in FIG. 27 performs step 762B to decrease the control target value of the element temperature and lower the voltage to be applied to the NOx sensor cell 4. A decrease in the voltage applied to the NOx sensor cell 4 reduces the oxygen discharge capacity of the NOx sensor cell 4. Therefore, the second modification provides a higher oxygen concentration around the first detection electrode 42 in the second internal space 32 than the first modification, which has been described earlier. This makes it possible to further increase the concentration of oxygen to be absorbed by the first detection electrode 42. Thus, the second modification provides a higher oxygen concentration in the NOx sensor 1 than the first modification. Consequently, the second modification makes it possible to accurately locate an inflection point.

Further, if the judgment result obtained in step 766 does not indicate that a fuel cut is being continuously performed, or if the judgment result obtained in step 770 indicates that the integrated air amount Qa is greater than the reference value Qth, the routine shown in FIG. 27 performs steps 768B and 7728 to recover the control target value of the element temperature and the voltage applied to the NOx sensor cell 4.

(Third Modification)

Figure 28:
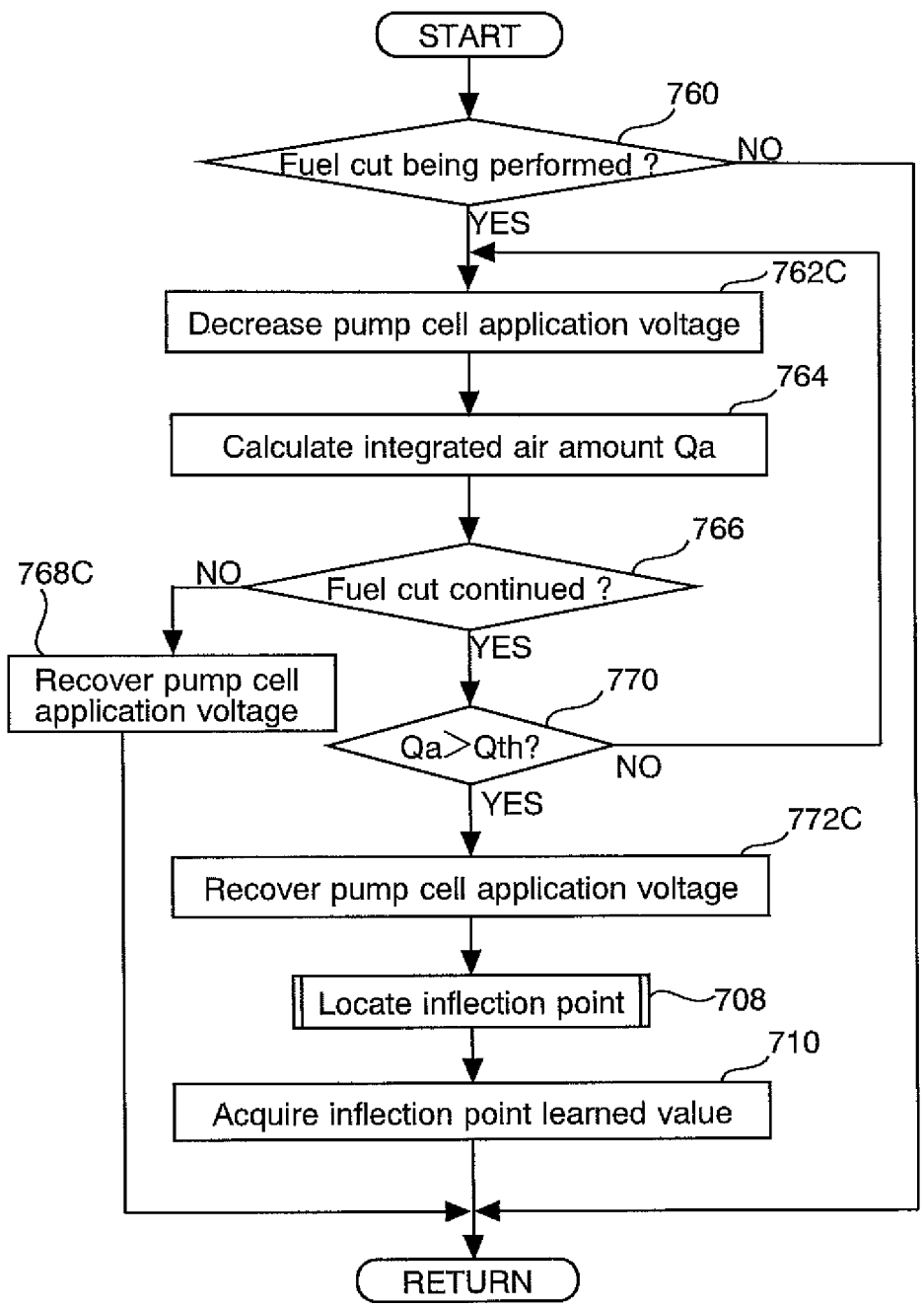
FIG. 28 is a flowchart illustrating a routine that the ECU 8 executes in accordance with a third modification of the eighth embodiment of the present invention.

A third modification of the eighth embodiment will now be described with reference to a method of increasing the concentration of oxygen in the NOx sensor 1 without decreasing the element temperature of the NOx sensor 1. More specifically, the third modification applies a lower voltage to the oxygen pump cell 2 than normal during a fuel cut. FIG. 28 is a flowchart illustrating a routine that the ECU 8 executes in accordance with the third modification of the eighth embodiment. The routine shown in FIG. 28 differs from the routine shown in FIG. 25 in that the former performs steps 762C, 768C, and 772C instead of steps 762, 768, and 772. These differences will be described below.

If the judgment result obtained in step 760 indicates that a fuel cut is being performed, the routine shown in FIG. 28 performs step 762C to apply a lower voltage to the oxygen pump cell 2 than normal. Thus, the oxygen discharge capacity of the oxygen pump cell 2 decreases. This makes it possible to increase the concentration of oxygen in the NOx sensor 1, that is, the concentration of oxygen in the first and second internal spaces 31, 32 and the concentration of oxygen to be absorbed by the first detection electrode 42. The third modification does not lower the element temperature. Therefore, it is possible to promptly use the NOx sensor cell output for the other control operations as far as the voltage applied to the oxygen pump cell 2 is recovered in a situation where a fuel cut is going to be discontinued (step 768C). Consequently, the third modification makes it possible to further suppress the deterioration of exhaust emission characteristics as compared to the first and second modifications.

Further, if the judgment result obtained in step 770 indicates that the integrated air amount Qa is greater than the reference value Qth, the routine shown in FIG. 28 performs step 772C to recover the voltage applied to the oxygen pump cell 2. Subsequently, the routine performs step 708 to locate an inflection point and then performs step 710 to acquire an inflection point learned value.

(Fourth Modification)

Figure 29:
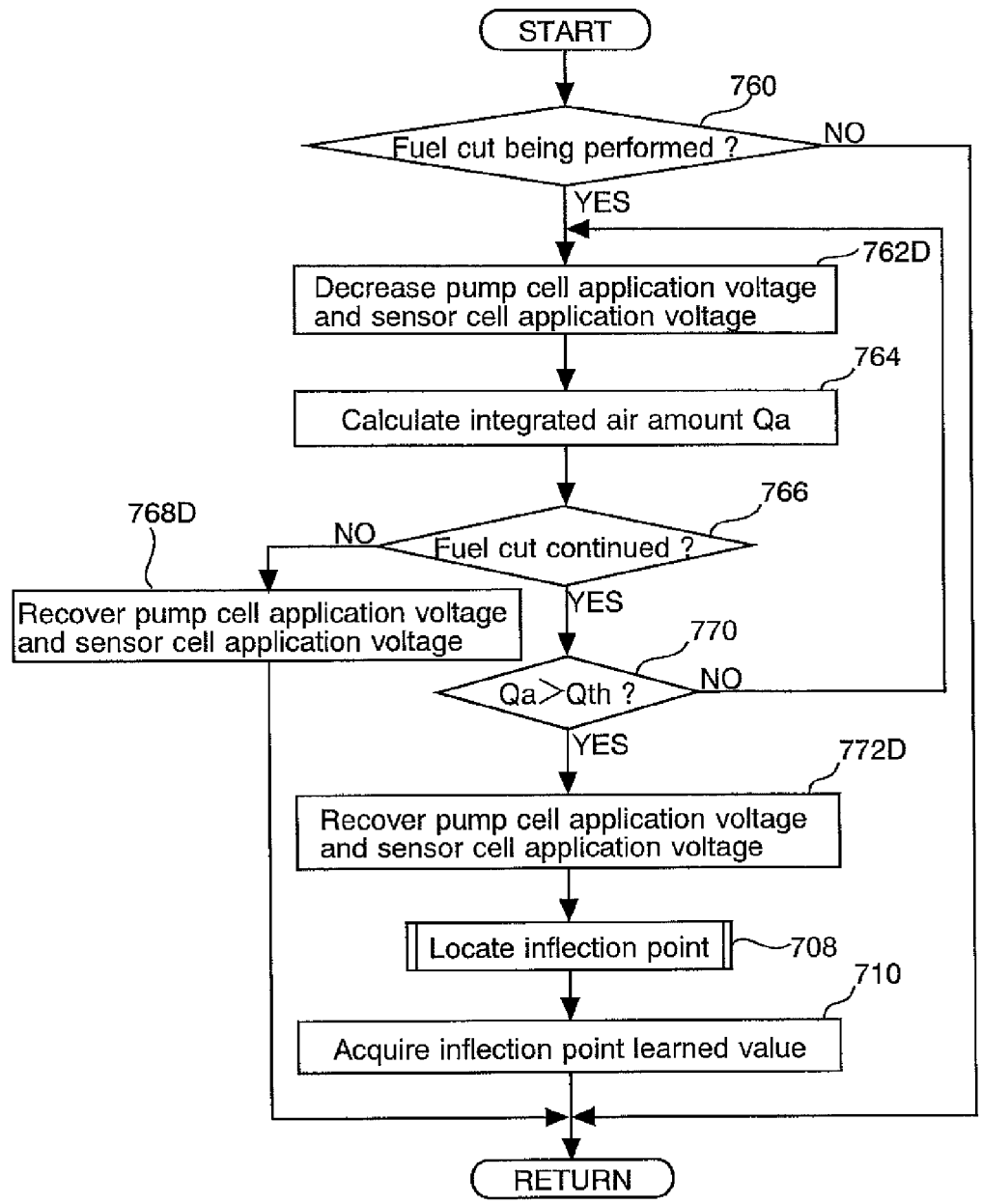
FIG. 29 is a flowchart illustrating a routine that the ECU 8 executes in accordance with a fourth modification of the eighth embodiment of the present invention.

To increase the concentration of oxygen in the NOx sensor 1, a fourth modification of the eighth embodiment not only applies a lower voltage to the oxygen pump cell 2 than normal, but also reduces the voltage applied to the NOx sensor cell 4, as shown in FIG. 29. FIG. 29 is a flowchart illustrating a routine that the ECU 8 executes in accordance with the fourth modification of the third embodiment. The routine shown in FIG. 29 differs from the routine shown in FIG. 25 in that the former performs steps 762D, 768D, and 772D instead of steps 762, 768, and 772. These differences will be described below.

If the judgment result obtained in step 760 indicates that a fuel cut is being performed, the routine shown in FIG. 29 performs step 762D to apply a lower voltage to the oxygen pump cell 2 than normal and apply a lower voltage to the NOx sensor cell 4 than normal. Thus, the fourth modification provides a higher oxygen concentration around the first detection electrode 42 in the second internal space 32 than the third modification, which has been described earlier. This makes it possible to further increase the concentration of oxygen to be absorbed by the first detection electrode 42. Thus, the fourth modification provides a higher oxygen concentration in the NOx sensor 1 than the third modification. Consequently, the fourth modification makes it possible to accurately locate an inflection point.

Further, if the judgment result obtained in step 766 does not indicate that a fuel cut is being continuously performed, or if the judgment result obtained in step 770 indicates that the integrated air amount Qa is greater than the reference value Qth, the routine shown in FIG. 29 performs steps 768D and 772D to recover the voltage applied to the oxygen pump cell 2 and the voltage applied to the NOx sensor cell 4.

In the eighth embodiment and its modifications, the "oxygen concentration control means" according to the first aspect of the present invention is implemented when the ECU 8 performs step 762, 762A, 762B, 762C, or 762D; the "oxygen concentration increase means" according to the fifteenth aspect of the present invention is implemented when the ECU 8 performs step 762, 762A, 762B, 762C, or 762D; the "heater control means" according to the seventeenth aspect of the present invention is implemented when the ECU 8 performs step 762, 762A, or 762B; the "oxygen pump cell control means" according to the eighteenth aspect of the present invention is implemented when the ECU 8 performs step 762C or 762D; the "inflection point location means" according to the fifteenth aspect of the present invention is implemented when the ECU 8 performs step 708; and the "Inflection point learned value storage means" according to the fifteenth and twentieth aspects of the present invention is implemented when the ECU 8 performs step 710.

Ninth Embodiment

A ninth embodiment of the present invention will now be described with reference to FIGS. 30 and 31. A system according to the ninth embodiment is implemented when the hardware configuration shown in FIGS. 1 and 14 is employed to let the ECU 8 execute a later-described routine shown in FIG. 31.

Features of Ninth Embodiment

The sixth and seventh embodiments learn the information about an inflection point at engine start. The eighth embodiment learns the information about an inflection point during a fuel cut. The ninth embodiment will be described with reference to a case where the inflection point information is learned in an idle state.

In an idle state, the activity of the SCR catalyst 122 is higher than at engine start. Therefore, the NOx concentration prevailing downstream of the SCR catalyst 122 in an idle state is lower than at engine start. However, when the NOx concentration prevailing downstream of the SCR catalyst 122 changes in an idle state, the NOx sensor cell output changes accordingly as well. Consequently, inflection point location may not accurately be achieved.

As such being the case, it is conceivable that an estimated value of the NOx concentration may be used to correct the NOx sensor cell output as is the case with the seventh embodiment, which has been described earlier. However, the amount of NOx discharge is small in an idle state as mentioned earlier. As indicated in FIG. 30, the NOx concentration prevailing in an idle state can be decreased by increasing the amount of urea water added from the urea water addition valve 123. FIG. 30 is a diagram illustrating the relationship between the amount of urea water addition and the NOx concentration prevailing downstream of the SCR catalyst 122.

Figure 30:
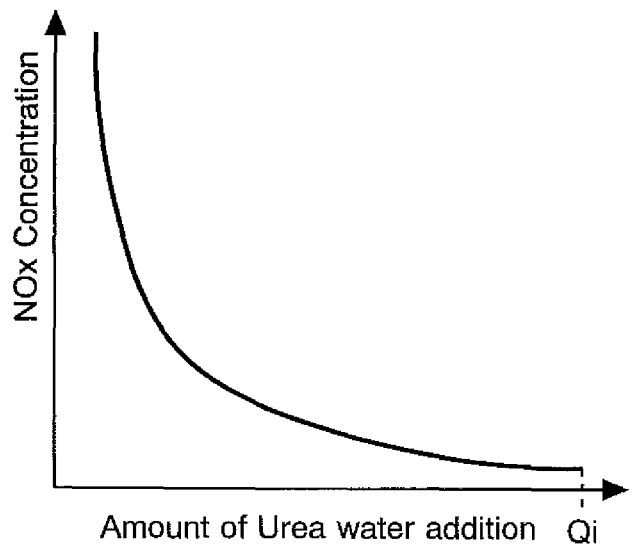
FIG. 30 is a diagram illustrating the relationship between the amount of urea water addition and the NOx concentration prevailing downstream of the SCR catalyst 122.
Figure 31:
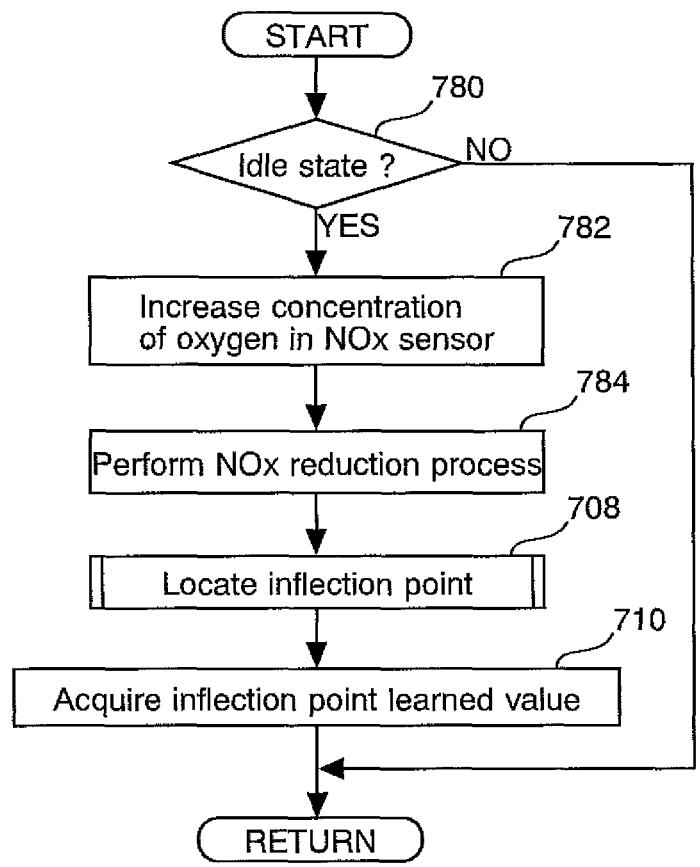
FIG. 31 is a flowchart illustrating a routine that the ECU 8 executes in accordance with a ninth embodiment of the present invention.

In view of the above circumstances, the ninth embodiment decreases the NOx concentration in an idle state by increasing the amount of urea water addition as indicated, for instance, by Qi in FIG. 30. Subsequently, the ninth embodiment locates an inflection point in the NOx sensor cell output and learns the information about the inflection point.
[Details of Process Performed by Ninth Embodiment]
FIG. 31 is a flowchart illustrating a routine that the ECU 8 executes in accordance with the ninth embodiment. First of all, the routine shown in FIG. 31 performs step 780 to judge whether the engine 100 is in an idle state. If the judgment result obtained in step 780 does not indicate that the engine 100 is in an idle state, the routine terminates.

If, on the other hand, the judgment result obtained in step 780 indicates that the engine 100 is in an idle state, the routine performs step 782 to increase the concentration of oxygen in the NOx sensor 1. In step 782, the concentration of oxygen in the first and second internal spaces 31, 32 of the NOx sensor 1 and the concentration of oxygen to be absorbed by the first detection electrode 42 can be increased, for instance, by exercising heater energization control, controlling the element temperature control target value, or controlling the pump cell application voltage as described in conjunction with the eighth embodiment and its modifications.

The routine then proceeds to step 784 and performs a NOx reduction process. Step 784 is performed, for instance, to increase the urea water addition amount and the EGR amount. Next, the routine proceeds to step 708. In step 708, the routine shown in FIG. 17 locates an inflection point in the NOx sensor cell output. Subsequently, the routine shown in FIG. 31 performs step 710 to acquire the information about the inflection point as a learned value in the same manner as the routine shown in FIG. 16.

As described above, the ninth embodiment performs the NOx reduction process in an idle state and then locates an inflection point in the NOx sensor cell output. This makes it possible, even in an idle state, to accurately locate an inflection point and learn the information about the inflection point with high accuracy without being affected by changes in the concentration of NOx emitted from the engine 100. Consequently, activity judgment variations caused by the difference in the engine operating status can be reduced. In addition, learning is performed in an idle state to ensure sufficient learning frequency.

The ninth embodiment, which has been described above, uses a learned value to reduce activity judgment variations caused by the difference in the engine operating status. However, the learned value may alternatively be used to form a deterioration judgment about the NOx sensor 1. More specifically, the ninth embodiment, which has been described above, makes it possible to accurately learn an inflection point (active site). Therefore, the accuracy of NOx sensor deterioration judgment can be effectively increased by comparing a NOx sensor cell output value obtained after such learning against a predetermined value for deterioration judgment purposes.

In the ninth embodiment, the "oxygen concentration control means" according to the first aspect of the present invention is implemented when the ECU 8 performs step 782; the "NOx concentration control means" according to the nineteenth aspect of the present invention is implemented when the ECU 8 performs step 784; the "inflection point location means" according to the fifteenth aspect of the present invention is implemented when the ECU 8 performs step 708; and the "inflection point learned value storage means" according to the fifteenth aspect of the present invention is implemented when the ECU 8 performs step 710.

The invention claimed is:
1. A gas concentration detection apparatus comprising:
a gas sensor that includes a gas concentration detection cell and an oxygen pump cell, wherein the oxygen pump cell changes a concentration of oxygen in a measurement target gas and removes excess oxygen from the measurement target gas, and the gas concentration detection cell detects a concentration of a specific gas component in the gas whose oxygen concentration is changed by the oxygen pump cell; and an electronic control unit having control logic configured to cause the electronic control unit to:

form a deterioration judgment about the gas sensor in accordance with a cell output from the gas concentration detection cell; and form a deterioration judgment about the gas sensor during a warm-up of the gas sensor and execution of the oxygen pump cell in accordance with the cell output obtained before an inflection point appears in the cell output of the gas concentration detection cell, wherein the inflection point is a point at which oxygen in an internal space of the gas sensor is substantially removed by the oxygen pump cell.

2. The gas concentration detection apparatus according to claim 1, wherein the electronic control unit acquires a correlation value of the rate at which the cell output increases during a cell output increase process (hereinafter referred to as the increase rate correlation value), and forms a deterioration judgment about the gas concentration detection cell in accordance with a comparison between the increase rate correlation value and a predetermined reference value.

3. The gas concentration detection apparatus according to claim 2, wherein the electronic control unit acquires an increase rate of the cell output; and forms a deterioration judgment about the gas concentration detection cell when the increase rate is lower than a predetermined reference value.

4. The gas concentration detection apparatus according to claim 1, wherein the oxygen pump cell discharges excess oxygen in the measurement target gas upon voltage application to the oxygen pump cell; and the electronic control unit acquires a correlation value of the rate at which the cell output decreases during a cell output decrease process (hereinafter referred to as the decrease rate correlation value), and forms a deterioration judgment about the oxygen pump cell in accordance with a comparison between the decrease rate correlation value and a predetermined reference value.

5. The gas concentration detection apparatus according to claim 4, wherein the electronic control unit acquires a decrease rate of the cell output; and forms a deterioration judgment about the oxygen pump cell when the decrease rate is lower than a predetermined reference value.

6. The gas concentration detection apparatus according to claim 4, wherein the electronic control unit acquires an integrated value of the cell output that is reached during the interval between the instant at which the gas sensor begins to warm up and the instant at which an inflection point appears; and forms a deterioration judgment about the oxygen pump cell when the integrated value is greater than a predetermined reference value.

7. The gas concentration detection apparatus according to claim 1, wherein the electronic control unit:

acquires a cell output at the inflection point (hereinafter referred to as the inflection point cell output); and stores a learned value concerning the inflection point cell output;

form a deterioration judgment about the gas sensor in accordance with a comparison between the inflection point cell output and the learned value.

8. The gas concentration detection apparatus according to claim 7, wherein, when the cell output is smaller than the learned value and the deviation between the learned value and the cell output is greater than a predetermined reference value, the electronic control unit concludes that the gas sensor is deteriorated.

9. The gas concentration detection apparatus according to claim 7, wherein, when the cell output is greater than the learned value and the absolute value of the deviation between the learned value and the cell output is greater than a predetermined reference value, the electronic control unit concludes that the gas sensor is deteriorated.

10. The gas concentration detection apparatus according to claim 7, wherein the electronic control unit forms a recoverable temporary deterioration judgment about the gas sensor in accordance with a comparison between the cell output and the learned value.

11. The gas concentration detection apparatus according to claim 10, wherein, when the absolute value of the deviation between the learned value and the cell output is smaller than a predetermined reference value, the electronic control unit concludes that the gas sensor is temporarily deteriorated.

12. The gas concentration detection apparatus according to claim 10, wherein the electronic control unit performs a deterioration recovery process on the gas sensor when the gas sensor is judged to be temporarily deteriorated.

13. The gas concentration detection apparatus according to claim 7, wherein the electronic control unit stores the cell output as an updated learned value when the cell output is smaller than the learned value and the deviation between the learned value and the cell output is smaller than a predetermined reference value.

14. A gas concentration detection apparatus comprising:

a gas sensor that includes a gas concentration detection cell and an oxygen pump cell that changes a concentration of oxygen in a measurement target gas, wherein the oxygen pump cell increases the concentration of oxygen in the measurement target gas, and the gas concentration detection cell detects a concentration of a specific gas component in the gas whose oxygen concentration is changed by the oxygen pump cell; and an electronic control unit having control logic configured to cause the electronic control unit to:

form a deterioration judgment about the gas sensor in accordance with a cell output from the gas concentration detection cell;

while the oxygen concentration is decreased after being increased from a predetermined value by the oxygen pump cell, locate an inflection point appearing in the cell output as an active site of the gas sensor, wherein the inflection point is a point at which the oxygen in an internal space of the gas sensor is substantially removed by the oxygen pump cell;

store an inflection point learned value that is the information about the inflection point located by the inflection point location means; and form a deterioration judgment about the gas sensor in accordance with the inflection point learned value stored by the electronic control unit.

15. The gas concentration detection apparatus according to claim 14, wherein the electronic control unit:

estimates a NOx concentration in the measurement target gas; and corrects the cell output by using the NOx concentration estimated by the electronic control unit; and while the oxygen concentration is decreased after being increased from a predetermined value by the oxygen pump cell, identifies an inflection point in the cell output corrected by the electronic control unit as an active site of the gas sensor.

16. The gas concentration detection apparatus according to claim 14, wherein the oxygen pump cell discharges excess oxygen in the measurement target gas and the electronic control unit controls the power supply to a heater for warming up the oxygen pump cell, and supplies a smaller amount of power to the heater than normal during an internal combustion engine fuel cut.

17. The gas concentration detection apparatus according to claim 14, wherein oxygen pump cell discharges excess oxygen in the measurement target gas upon voltage application and the electronic control unit controls the power supply to the oxygen pump cell, and supplies a smaller amount of power to the oxygen pump cell than normal during an internal combustion engine fuel cut.

18. The gas concentration detection apparatus according to claim 14, wherein the electronic control unit:
   controls the concentration of NOx in the measurement target gas; and
   locates the inflection point while the electronic control unit is executed.

19. The gas concentration detection apparatus according to claim 14, wherein the electronic control unit stores, as a map, the cell output prevailing when the inflection point is located, a physical property value correlated to an element temperature, and the time required for locating the inflection point.

* * * * *